United States Patent
Rabuka et al.

(10) Patent No.: US 11,857,637 B2
(45) Date of Patent: Jan. 2, 2024

(54) ANTI-CD25 ANTIBODY-MAYTANSINE CONJUGATES AND METHODS OF USE THEREOF

(71) Applicant: R.P. Scherer Technologies, LLC, Carson City, NV (US)

(72) Inventors: David Rabuka, Kensington, CA (US); Penelope M. Drake, Castro Valley, CA (US)

(73) Assignee: R.P. Scherer Technologies, LLC, Carson City, NV (US)

(*) Notice: Subject to any disclaimer, the term of this patent is extended or adjusted under 35 U.S.C. 154(b) by 0 days.

(21) Appl. No.: 17/519,183

(22) Filed: Nov. 4, 2021

(65) Prior Publication Data

US 2022/0143205 A1     May 12, 2022

Related U.S. Application Data

(63) Continuation of application No. PCT/US2019/054753, filed on Oct. 4, 2019.

(51) Int. Cl.
| | | |
|---|---|---|
| A61K 47/68 | (2017.01) | |
| C07K 16/28 | (2006.01) | |
| A61K 47/65 | (2017.01) | |

(52) U.S. Cl.
CPC ...... *A61K 47/6807* (2017.08); *C07K 16/2866* (2013.01); *A61K 47/65* (2017.08)

(58) Field of Classification Search
CPC ............ A61K 47/6803; A61K 47/6849; A61K 47/6867; A61K 47/6889; C07K 16/2866
See application file for complete search history.

(56) References Cited

U.S. PATENT DOCUMENTS

| | | |
|---|---|---|
| 7,985,783 B2 | 7/2011 | Carrico et al. |
| 8,097,701 B2 | 1/2012 | Carrico et al. |
| 8,349,910 B2 | 1/2013 | Carrico et al. |
| 8,729,232 B2 | 5/2014 | Rush et al. |
| 8,846,866 B2 | 9/2014 | Carrico et al. |
| 9,238,878 B2 | 1/2016 | Rabuka et al. |
| 9,310,374 B2 | 4/2016 | Kudirka et al. |
| 9,447,390 B2 | 9/2016 | Carrico et al. |
| 9,493,413 B2 | 11/2016 | Rabuka et al. |
| 9,540,438 B2 | 1/2017 | Barfield et al. |
| 9,833,515 B2 | 12/2017 | Kudirka et al. |
| 9,879,249 B2 | 1/2018 | Rabuka et al. |
| 10,124,070 B2 | 11/2018 | Rabuka et al. |
| 10,150,806 B2 | 12/2018 | Carrico et al. |
| 10,314,919 B2 | 6/2019 | Kudirka et al. |
| 10,464,894 B2 | 11/2019 | Rabuka et al. |
| 10,604,483 B2 | 3/2020 | Rabuka et al. |
| 10,745,464 B2 | 8/2020 | Carrico et al. |
| 10,888,623 B2 | 1/2021 | Kudirka et al. |
| 11,097,013 B2 | 8/2021 | Rabuka et al. |
| 2014/0322123 A1 | 10/2014 | Hafizovic et al. |
| 2016/0324937 A1 | 11/2016 | Vitalis et al. |
| 2017/0306300 A1 | 10/2017 | Kim et al. |
| 2018/0104351 A1 | 4/2018 | Kudirka et al. |
| 2019/0201541 A1 | 7/2019 | Maclaren |
| 2020/0010561 A1 | 1/2020 | Kim et al. |
| 2020/0246480 A1 | 8/2020 | Rabuka et al. |
| 2020/0317610 A1 | 10/2020 | Rabuka et al. |
| 2021/0024614 A1 | 1/2021 | Carrico et al. |
| 2021/0162054 A1 | 6/2021 | Kudirka et al. |

FOREIGN PATENT DOCUMENTS

| | | | |
|---|---|---|---|
| WO | WO-2005030252 A1 * | 4/2005 | ............... A61P 11/00 |
| WO | 2017083306 | 5/2017 | |

OTHER PUBLICATIONS

Kreitman et al (Journal of Clinical Oncology, 2000, vol. 18, pp. 1622-1636) (Year: 2000).*
Powell et al, Journal of Immunology, 2007, vol. 179, pp. 4919-4928 (Year: 2007).*
Esteva et al (Am Soc Clin Oncol Educ Book, 2015, pp. e117-e1125) (Year: 2015).*
Depper et al (Journal of Immunology, 1983, vol. 131, pp. 690-696). (Year: 1983).*
Nakase et al (PLoS One, 2015, vol. 10, 19 pages). (Year: 2015).*
Binder et al (Cancer Research, 2007, vol. 67, pp. 3518-3523). (Year: 2007).*
Perez et al (Drug Discovery Today, 2014, vol. 19, pp. 869-881) (Year: 2014).*
M.J. Flynn et al., "ADCT-301, a Pyrrolobenzodiazepine (PBD) Dimer-Containing Antibody-Drug Conjugate (ADC) Targeting CD25-Expressing Hematological Maligmanices", Molecular Cancer Therapeutics, vol. 15, No. 11, Nov. 1, 2016 (Nov. 1, 2016), pp. 2709-2721.
Michael J Flynn et al., "The Emerging Role of Anti-cd25 Directed Therapies as Both Immune Modulators and Targeted Agents in Cancer", British Journal of Haematology, John Wiley, Hoboken, USA, vol. 179, No. 1, May 30, 2017 (May 30, 2017), pp. 20-35.
Penelope M. Drake et al., "Aldehyde Tag Coupled with HIPS Chemistry Enables the Production ADCs Conjugated Site-Specifically to Different Antibody Regions with Distinct in Vivo Efficacy and PK Outcomes", Bioconjugate Chemistry, vol. 25, No. 7, Jul. 16, 2014 (Jul. 16, 2014), pp. 1331-1341.

\* cited by examiner

*Primary Examiner* — Karen A. Canella
(74) *Attorney, Agent, or Firm* — Rudy Ng; Mandar Joshi; Bozicevic, Field & Francis LLP

(57) ABSTRACT

The present disclosure provides anti-CD25 antibody-maytansine conjugate structures. The disclosure also encompasses methods of production of such conjugates, as well as methods of using the same.

22 Claims, 16 Drawing Sheets
Specification includes a Sequence Listing.

A.

B.

C.

Light chain conserved region:

```
         140        150        160        170        180       189
RTVAAPSVFI FPPSDEQLKS GTASVVCLLN NFYPREAKVQ WKVDNALQSG NSQESVTEQD
         200        210        220        230  236
SKDSTYSLSS TLTLSKADYE KHKVYACEVT HQGLSSPVTK SFNRGEC
```

Heavy chain conserved region:

```
         130        140        150        160        170        180
ASTKGPSVFP LAPSSKSTSG GTAALGCLVK DYFPEPVTVS WNSGALTSGV HTFPAVLQSS
         190        200        210        220        230        240
GLYSLSSVVT VPSSSLGTQT YICNVNHKPS NTKVDKKVEP KSCDKTHTCP PCPAPELLGG
         250        260        270        280        290        300
PSVFLFPPKP KDTLMISRTP EVTCVVVDVS HEDPEVKFNW YVDGVEVHNA KTKPREEQYN
         310        320        330        340        350        360
STYRVVSVLT VLHQDWLNGK EYKCKVSNKA LPAPIEKTIS KAKGQPREPQ VYTLPPSREE
         370        380        390        400        410        420
MTKNQVSLTC LVKGFYPSDI AVEWESNGQP ENNYKTTPPV LDSDGSFFLY SKLTVDKSRW
         430        440        450
QQGNVFSCSV MHEALHNHYT QKSLSLSPGK
```

FIG. 12A

```
Homo sapiens IgG1 constant region; GenBank P01857.1
Homo sapiens IgG2 constant region; GenBank P01859.2
Homo sapiens IgG3 constant region; GenBank P01860.2
Homo sapiens IgG4 constant region; GenBank AAB59394.1
Homo sapiens IgA constant region; GenBank AAT74070

178
IgG1   --ASTKGPSVFPLAPSSKSTSGGTAALGCLVKDYFP-EPVTVSWNSGALTSGVHTFPAVL
IgG3   --ASTKGPSVFPLAPCSRSTSGGTAALGCLVKDYFP-EPVTVSWNSGALTSGVHTFPAVL
IgG2   --ASTKGPSVFPLAPCSRSTSESTAALGCLVKDYFP-EPVTVSWNSGALTSGVHTFPAVL
IgG4   --STKGPSVFPLAPCSRSTSESTAALGCLVKDYFP-EPVTVSWNSGALTSGVHTFPAVL
IgA    --ASPTSPKVFPLSLCS-TQPDGNVVIACLVQGFFPQEPLSVTWSESGQGVTARNFPPSQ
         *  *  ***** *   ::   :   * ***  * ** *** *   * *     *

220
IgG1   QSSG-LYSLSSVVTVPS-SSLGTQTYICNVNHKPSNTKVDKKVE----------------
IgG3   QSSG-LYSLSSVVTVPS-SSLGTQTYTCNVNHKPSNTKVDKRVELKTPLGDTTHTCPRCP
IgG2   QSSG-LYSLSSVVTVPS-SNFGTQTYTCNVDHKPSNTKVDKTVER---------------
IgG4   QSSG-LYSLSSVVTVPS-SSLGTKTYTCNVDHKPSNTKVDKRVES---------------
IgA    DASGDLYTTSSQLTLPATQCLAGKSVTCHVKHY-TNPSQDVTVPCP--------------
         :  **   ** ** ::   :      * *  ::   *

FIG. 12B
```

```
IgG1  ------------------------------PKSCDKTHTCPPCPAPELLGGPSVFLFPP      249
IgG3  EPKSCDTPPCPRCPEPKSCDTPPPCPRCPEPKSCDTPPPCPRCPAPELLGGPSVFLFPP
IgG2  ------------------------------KCCVE---CPPCPAPPVAG-PSVFLFPP
IgG4  ------------------------------KYGPPCPSCPAPEFLGGPSVFLFPP
IgA   ------------------------------VPSTPPTPSPSTPPTPSPSCCHPRLSLHR
                                         *:*     .      ..

IgG1  KPKDTLMISRTPEVTCVVVDVSHEDPEVKFNWYVDGVEVHNAKTKPREEQYNSTYRVVSV     309
IgG3  KPKDTLMISRTPEVTCVVVDVSHEDPEVQFKWYVDGVEVHNAKTKPREEQYNSTFRVVSV
IgG2  KPKDTLMISRTPEVTCVVVDVSHEDPEVQFNWYVDGVEVHNAKTKPREEQFNSTFRVVSV
IgG4  KPKDTLMISRTPEVTCVVVDVSQEDPEVQFNWYVDGVEVHNAKTKPREEQFNSTYRVVSV
IgA   PALEDLLLGSEANLTCTLTGLR-DASGVTFTWTPS---SGKSAVQGPPDRDLCGCYSVSSV
       *  *::.  . :::.:**     *  *.:*      . ..   :    * **
```

FIG. 12B (Cont'd)

```
                                                                                              368
IgG1  LTVLHQDWLNGKEYKCKVSNKALPAPIEKTISKAKGQPREPQVYTLPPSRDELTKNQVS-
IgG3  LTVLHQDWLNGKEYKCKVSNKALPAPIEKTISKTKGQPREPQVYTLPPSREEMTKNQVS-
IgG2  LTVVHQDWLNGKEYKCKVSNKGLPAPIEKTISKTKGQPREPQVYTLPPSREEMTKNQVS-
IgG4  LTVLHQDWLNGKEYKCKVSNKGLPSSIEKTISKAKGQPREPQVYTLPPSQEEMTKNQVS-
IgA   LSGCAEPWNHGKTFTCTAAYPESKTPLTATLSKS-GNTFRPEVHLLPPSEELALNELVT
       *:  :   *    **          :    *   *:: :  *** *:: ***   *::

423
IgG1  LTCLVKGFYPSDIAVEWESNGQ---PENNYKTTPPVLDSDG---SFFLYSKLTVDKSRWQQ
IgG3  LTCLVKGFYPSDIAVEWESSGQ---PENNYNTTPPMLDSDG---SFFLYSKLTVDKSRWQQ
IgG2  LTCLVKGFYPSDISVEWESNGQ---PENNYKTTPPMLDSDG---SFFLYSKLTVDKSRWQQ
IgG4  LTCLVKGFYPSDIAVEWESNGQ---PENNYKTTPPVLDSDG---SFFLYSRLTVDKSRWQE
IgA   LTCLARGFSPKDVLVRWLQGSQELPREKYLTWASRQEPSQGTTTFAVTSILRVAAEDWKK
      ****  **.*:  :**.* *.:   *   *: :      *   :****  * **** ::

451
IgG1  GNVFSCSVMHEALHNHYTQKSLSLSPGK--------------
IgG3  GNIFSCSVMHEALHNRFTQKSLSLSPGK--------------
IgG2  GNVFSCSVMHEALHNHYTQKSLSLSPGK--------------
IgG4  GNVFSCSVMHEALHNHYTQKSLSLSLGK--------------
IgA   GDTFSCMVGHEALPLAFTQKTIDRLAGKPTHVNVSVVMAEVDGTCY
      *: ***  ****  : ***::  * **
```

FIG. 12B (Cont'd)

Seq1 = *Homo sapiens* kappa light chain constant region; GenBank CAA75031.1
Seq2 = *Homo sapiens* kappa light chain constant region; GenBank BAC0168.1
Seq3 = *Homo sapiens* lambda light chain constant region; GenBank CAA75033
Seq4 = *Mus musculus* light chain constant region; GenBank AAB09710.1
Seq5 = *Rattus norvegicus* light chain constant region; GenBank AAD10133

```
                                                              189
Seq1  RTVAAPSVFIFPPSDEQLKSGTASVVCLLNNFYPREAKVQWKVDNALQSGNSQESVTEQD
Seq2  RTVAAPSVFIFPPSDEQLKSGTASVVCLLNNFYPREAKVQWKVDNALQSGNSQESVTEQD
Seq4  RADAAPTVSIFPPSSEQLTSGGASVVCFLNNFYPKDINVKWKIDGSERQNGVLNSWTDQD
Seq5  RADAAPTVSIFPPSMEQLTSGGATVVCFVNNFYPRDISVKWKIDGSEQRDGVLDSVTDQD
Seq3  QPKAAPSVTLFPPSSEELQANKATLVCLISDFYPGAVTVAWKADSSPVKAGVETTTPSKQ
      . ***.* .***:  * * .*::** :***: :.**..*  **.*.. .     *..

236
Seq1  SKDSTYSLSSTLTLSKADYEKHKVYACEVTHQGLSSPVTKSFNRGEC
Seq2  SKDSTYSLSSTLTLSKADYEKHKLYACEVTHQGLSSPVTKSFNRGEC
Seq4  SKDSTYSMSSTLTLTKDEYERHNSYTCEATHKTSTSPIVKSFNRGEC
Seq5  SKDSTYSMSSTLSLTKVEYERHNLYTCEVVHKTSSSPVVKSFNRNEC
Seq3  S-NNKYAASSYLSLTPEQWKSHKSYSCQVTHEG--STVEKTVAPTECS
      *  . ..:** :*:* :   :**.*:*:.* .    :**.. .*
```

FIG. 12C

ANTI-CD25 ANTIBODY-MAYTANSINE CONJUGATES AND METHODS OF USE THEREOF

CROSS-REFERENCE TO RELATED APPLICATIONS

This application is a continuation of International Application No. PCT/US2019/054753, filed Oct. 4, 2019, the disclosure of which is incorporated herein by reference in its entirety.

REFERENCE TO ELECTRONIC SEQUENCE LISTING

A Sequence Listing is provided herewith as a text file, "RDWD-033CON_SEQ_LIST_ST25" created on Oct. 19, 2022 and having a size of 59 KB. The contents of the text file are incorporated by reference herein in their entirety.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

Interleukin-2 (IL-2) and its receptor (IL-2R) play an important role as signaling molecules in cellular immune responses. This ligand-receptor interaction has been considered a target in the clinical treatment of acute allograft rejection, graft-versus-host disease, T-cell-mediated autoimmune disease, and certain hematologic malignancies. The IL-2R is composed of the α, β, and $\gamma_c$ subunits. Upon activation, they assemble to form the intermediate-affinity IL-2R ($\beta\gamma_c$) or the high-affinity IL-2R ($\beta\gamma_c$), in which the IL-2 interaction with the α chain initiates the sequential recruitment of the β and $\gamma_c$ subunits. T cells express the α chain (CD25) upon activation. CD25 is expressed on Hodgkin lymphoma (HL) cells and various T and B cell non-Hodgkin lymphoma (NHL) cells. CD25 is expressed on nearly 100% of adult T-cell leukemia lymphoma cells and hairy cell leukemia cells. CD25 is also up-regulated in refractory Acute Myeloid Leukemia (AML). In addition, CD25 is expressed on regulatory T cells.

SUMMARY

The present disclosure provides anti-CD25 antibody-maytansine conjugate structures. The disclosure also encompasses methods of production of such conjugates, as well as methods of using the same.

Aspects of the present disclosure include a conjugate having at least one modified amino acid residue with a side chain of formula (I):

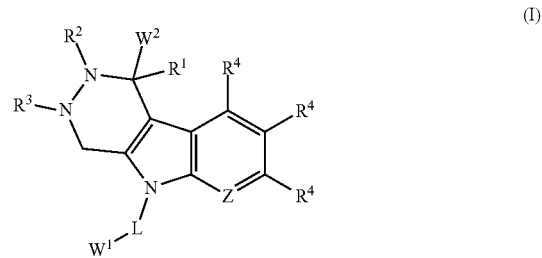

(I)

wherein

Z is $CR^4$ or N;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; L is a linker comprising $-(T^1-V^1)_a-(T^2-V^2)_b-(T^3-V^3)_c-(T^4-V^4)_d$-, wherein a, b, c and d are each independently 0 or 1, where the sum of a, b, c and d is 1 to 4;

$T^1$, $T^2$, $T^3$ and $T^4$ are each independently selected from $(C_1-C_{12})$alkyl, substituted $(C_1-C_{12})$alkyl, $(EDA)_w$, $(PEG)_n$, $(AA)_p$, $-(CR^{13}OH)_h-$, piperidin-4-amino (4AP), an acetal group, a hydrazine, a disulfide, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;

$V^1$, $V^2$, $V^3$ and $V^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

each $R^{13}$ is independently selected from hydrogen, an alkyl, a substituted alkyl, an aryl, and a substituted aryl;

each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl;

$W^1$ is a maytansinoid; and $W^2$ is an anti-CD25 antibody.

In some instances, the conjugate includes the following, where:

$T^1$ is selected from a (C$_1$-C$_{12}$)alkyl and a substituted (C$_1$-C$_{12}$)alkyl;

$T^2$, $T^3$ and $T^4$ are each independently selected from (EDA)$_w$, (PEG)$_n$, (C$_1$-C$_{12}$)alkyl, substituted (C$_1$-C$_{12}$) alkyl, (AA)$_p$, —(CR$^{13}$OH)$_h$—, 4-amino-piperidine (4AP), an acetal group, a hydrazine, and an ester; and $V^1$, $V^2$, $V^3$ and $V^4$ are each independently selected from the group consisting of a covalent bond, —CO—, —NR$^{15}$, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$—, and —P(O)OH—;

wherein:
(PEG)$_n$ is

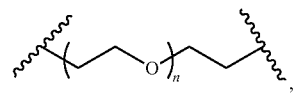

where n is an integer from 1 to 30;

EDA is an ethylene diamine moiety having the following structure:

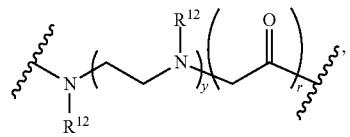

where y is an integer from 1 to 6 and r is 0 or 1;

4-amino-piperidine (4AP) is

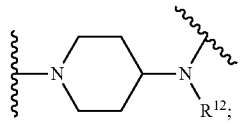

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In some instances, the conjugate includes the following, where: $T^1$, $T^2$, $T^3$ and $T^4$, and $V^1$, $V^2$, $V^3$ and $V^4$ are selected from the following table:

| $T^1$ | $V^1$ | $T^2$ | $V^2$ | $T^3$ | $V^3$ | $T^4$ | $V^4$ |
|---|---|---|---|---|---|---|---|
| (C$_1$-C$_{12}$)alkyl | —CONR$^{15}$— | (PEG)$_n$ | —CO— | — | — | — | — |
| (C$_1$-C$_{12}$)alkyl | —CO— | (AA)$_p$ | —NR$^{15}$— | (PEG)$_n$ | —CO— | — | — |
| (C$_1$-C$_{12}$)alkyl | —CO— | (AA)$_p$ | — | — | — | — | — |
| (C$_1$-C$_{12}$)alkyl | —CONR$^{15}$— | (PEG)$_n$ | —NR$^{15}$— | — | — | — | — |
| (C$_1$-C$_{12}$)alkyl | —CO— | (AA)$_p$ | —NR$^{15}$— | (PEG)$_n$ | —NR$^{15}$— | — | — |
| (C$_1$-C$_{12}$)alkyl | —CO— | (EDA)$_w$ | —CO— | — | — | — | — |
| (C$_1$-C$_{12}$)alkyl | —CONR$^{15}$— | (C$_1$-C$_{12}$)alkyl | —NR$^{15}$— | — | — | — | — |
| (C$_1$-C$_{12}$)alkyl | —CONR$^{15}$— | (PEG)$_n$ | —CO— | (EDA)$_w$ | — | — | — |
| (C$_1$-C$_{12}$)alkyl | —CO— | (EDA)$_w$ | — | — | — | — | — |
| (C$_1$-C$_{12}$)alkyl | —CO— | (EDA)$_w$ | —CO— | (CR$^{13}$OH)$_h$ | —CONR$^{15}$— | (C$_1$-C$_{12}$)alkyl | —CO— |
| (C$_1$-C$_{12}$)alkyl | —CO— | (AA)$_p$ | —NR$^{15}$— | (C$_1$-C$_{12}$)alkyl | —CO— | — | — |
| (C$_1$-C$_{12}$)alkyl | —CONR$^{15}$— | (PEG)$_n$ | —CO— | (AA)$_p$ | — | — | — |
| (C$_1$-C$_{12}$)alkyl | —CO— | (EDA)$_w$ | —CO— | (CR$^{13}$OH)$_h$ | —CO— | (AA)$_p$ | — |
| (C$_1$-C$_{12}$)alkyl | —CO— | (AA)$_p$ | —NR$^{15}$— | (C$_1$-C$_{12}$)alkyl | —CO— | (AA)$_p$ | — |
| (C$_1$-C$_{12}$)alkyl | —CO— | (AA)$_p$ | —NR$^{15}$— | (PEG)$_n$ | —CO— | (AA)$_p$ | — |
| (C$_1$-C$_{12}$)alkyl | —CO— | (AA)$_p$ | —NR$^{15}$— | (PEG)$_n$ | —SO$_2$— | (AA)$_p$ | — |
| (C$_1$-C$_{12}$)alkyl | —CO— | (EDA)$_w$ | —CO— | (CR$^{13}$OH)$_h$ | —CONR$^{15}$— | (PEG)$_n$ | —CO— |
| (C$_1$-C$_{12}$)alkyl | —CO— | (CR$^{13}$OH)$_h$ | —CO— | — | — | — | — |
| (C$_1$-C$_{12}$)alkyl | —CONR$^{15}$— | substituted (C$_1$-C$_{12}$)alkyl | —NR$^{15}$— | (PEG)$_n$ | —CO— | — | — |
| (C$_1$-C$_{12}$)alkyl | —SO$_2$— | (C$_1$-C$_{12}$)alkyl | —CO— | — | — | — | — |
| (C$_1$-C$_{12}$)alkyl | —CONR$^{15}$— | (C$_1$-C$_{12}$)alkyl | — | (CR$^{13}$OH)$_h$ | —CONR$^{15}$— | — | — |
| (C$_1$-C$_{12}$)alkyl | —CO— | (AA)$_p$ | —NR$^{15}$— | (PEG)$_n$ | —CO— | (AA)$_p$ | —NR$^{15}$— |
| (C$_1$-C$_{12}$)alkyl | —CO— | (AA)$_p$ | —NR$^{15}$— | (PEG)$_n$ | —P(O)OH— | (AA)$_p$ | — |
| (C$_1$-C$_{12}$)alkyl | —CO— | (EDA)$_w$ | — | (AA)$_p$ | — | — | — |
| (C$_1$-C$_{12}$)alkyl | —CONR$^{15}$— | (C$_1$-C$_{12}$)alkyl | —NR$^{15}$— | — | —CO— | — | — |
| (C$_1$-C$_{12}$)alkyl | —CONR$^{15}$— | (C$_1$-C$_{12}$)alkyl | —NR$^{15}$— | — | —CO— | (C$_1$-C$_{12}$)alkyl | —NR$^{15}$— |

-continued
| T$^1$ | V$^1$ | T$^2$ | V$^2$ | T$^3$ | V$^3$ | T$^4$ | V$^4$ |
|---|---|---|---|---|---|---|---|
| (C$_1$-C$_{12}$)alkyl | —CO— | 4AP | —CO | (C$_1$-C$_{12}$)alkyl | —CO— | (AA)$_p$ | — |
| (C$_1$-C$_{12}$)alkyl | —CO— | 4AP | —CO | (C$_1$-C$_{12}$)alkyl | —CO— | — | — |
In some instances, the conjugate includes the following, where: the linker, L, is selected from one of the following structures:
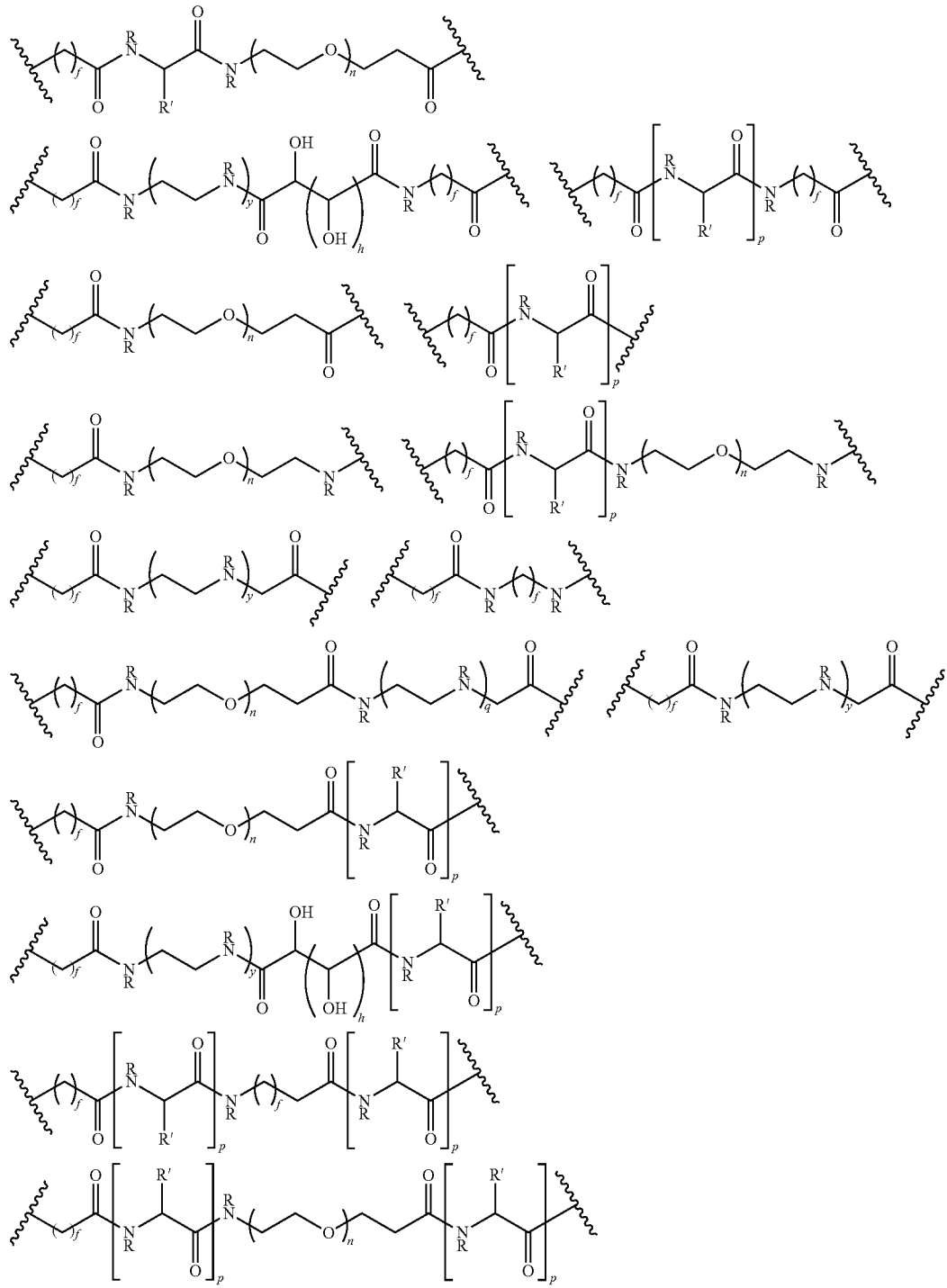

-continued
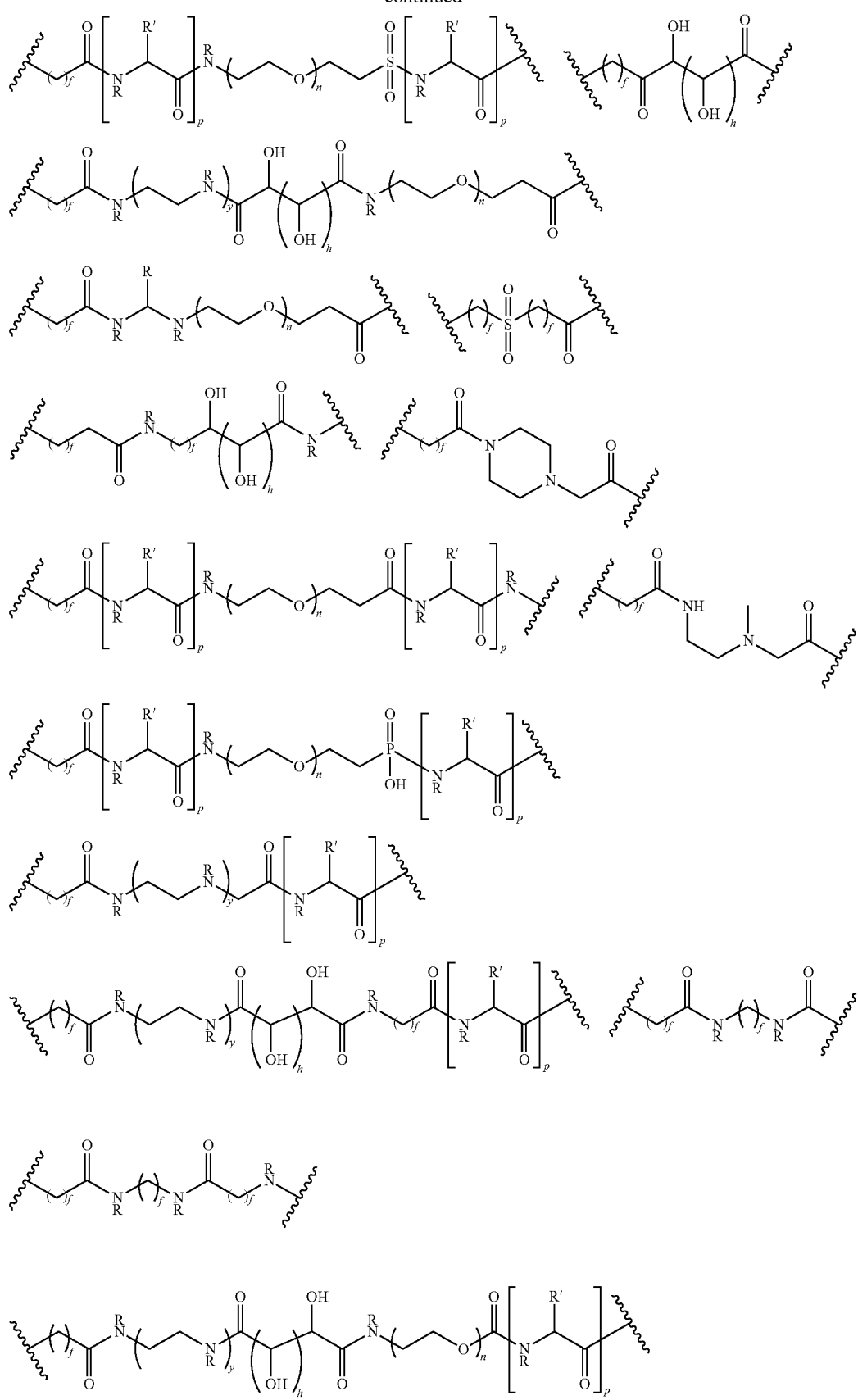

-continued
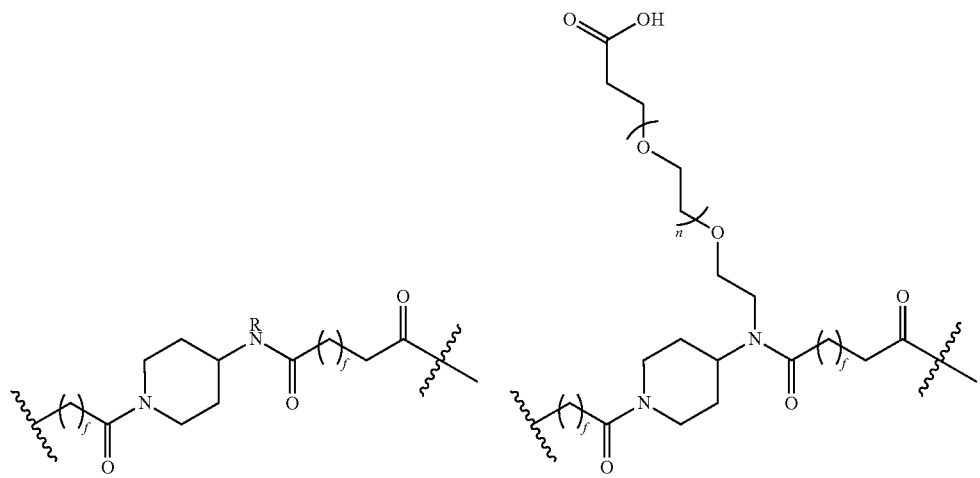
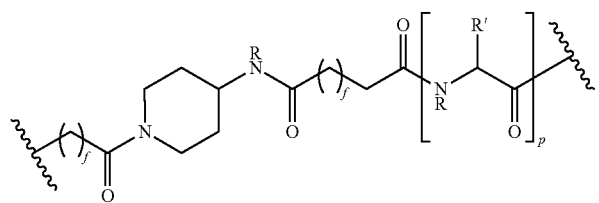
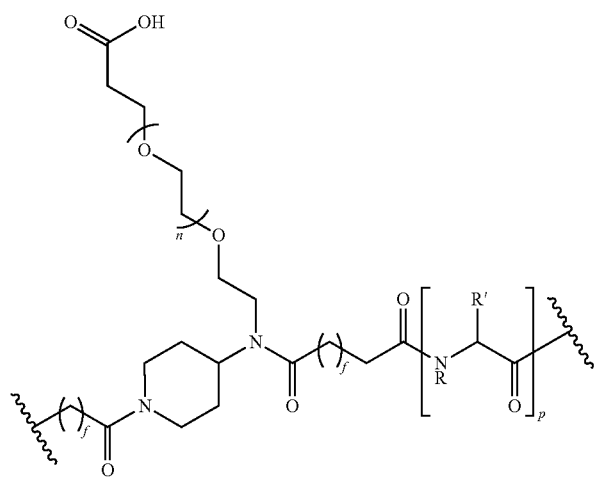

wherein
  each f is independently 0 or an integer from 1 to 12;
  each y is independently 0 or an integer from 1 to 20;
  each n is independently 0 or an integer from 1 to 30;
  each p is independently 0 or an integer from 1 to 20;
  each h is independently 0 or an integer from 1 to 12;
  each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
  each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In some instances, the maytansinoid is of the formula:

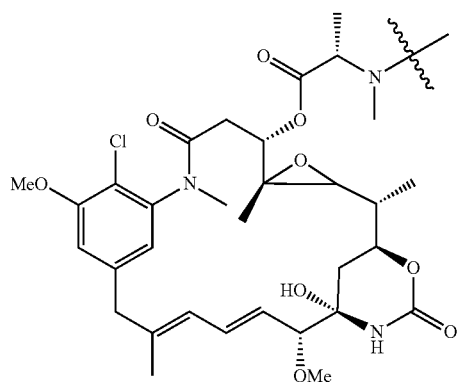

where ⌇ indicates the point of attachment between the maytansinoid and L.

In some instances, the conjugate includes the following, where: $T^1$ is $(C_1$-$C_{12})$alkyl, $V^1$ is —CO—, $T^2$ is 4AP, $V^2$ is —CO—, $T^3$ is $(C_1$-$C_{12})$alkyl, $V^3$ is —CO—, $T^4$ is absent and $V^4$ is absent.

In some instances, the linker, L, comprises the following structure:

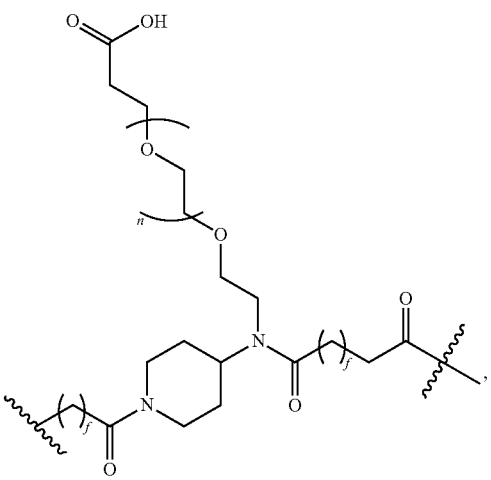

wherein
  each f is independently an integer from 1 to 12; and
  n is an integer from 1 to 30.

In some instances, the anti-CD25 antibody is an IgG1 antibody.

In some instances, the anti-CD25 antibody is an IgG1 kappa antibody.

In some instances, the anti-CD25 antibody competes with interleukin-2 (IL-2) for binding to CD25.

In some instances, the anti-CD25 antibody binds an epitope within amino acids 101-137, an epitope within amino acids 106-132, an epitope within amino acids 111-127, an epitope comprising amino acids 116-122, or an epitope consisting of amino acids 116-122, of a CD25 amino acid sequence depicted in Table 3.

In some instances, the anti-CD25 antibody competes for binding to CD25 with an antibody comprising the six complementarity determining regions (CDRs) of daclizumab.

In some instances, the anti-CD25 antibody comprises the six CDRs of daclizumab.

In some instances, the anti-CD25 antibody comprises a sequence of the formula (II):

$$X^1(FGly')X^2Z^{20}X^3Z^{30} \quad (II)$$

wherein
  FGly' is the modified amino acid residue of formula (I);
  $Z^{20}$ is either a proline or alanine residue;
  $Z^{30}$ is a basic amino acid or an aliphatic amino acid;
  $X^1$ may be present or absent and, when present, can be any amino acid, with the proviso that when the sequence is at the N-terminus of the conjugate, $X^1$ is present; and
  $X^2$ and $X^3$ are each independently any amino acid.

In some instances, the sequence is L(FGly')TPSR (SEQ ID NO: 144).

In some instances, the conjugate includes the following, where:
  $Z^{30}$ is selected from R, K, H, A, G, L, V, I, and P;
  $X^1$ is selected from L, M, S, and V; and
  $X^2$ and $X^3$ are each independently selected from S, T, A, V, G, and C.

In some instances, the modified amino acid residue is positioned at a C-terminus of a heavy chain constant region of the anti-CD25 antibody.

In some instances, the heavy chain constant region comprises a sequence of the formula (II):

$$X^1(FGly')X^2Z^{20}X^3Z^{30} \quad (II)$$

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence is C-terminal to the amino acid sequence SLSLSPG (SEQ ID NO: 145).

In some instances, the heavy chain constant region comprises the sequence SPGSL(FGly')TPSRGS (SEQ ID NO: 39).

In some instances, the conjugate includes the following, where:
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In some instances, the modified amino acid residue is positioned in a light chain constant region of the anti-CD25 antibody.

In some instances, the light chain constant region comprises a sequence of the formula (II):

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence is C-terminal to the sequence KVDNAL (SEQ ID NO: 42), and/or is N-terminal to the sequence QSGNSQ (SEQ ID NO: 43).

In some instances, the light chain constant region comprises the sequence KVDNAL(FGly')TPSRQSGNSQ (SEQ ID NO: 44).

In some instances, the conjugate includes the following, where:
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In some instances, the modified amino acid residue is positioned in a heavy chain CH1 region of the anti-CD25 antibody.

In some instances, the heavy chain CH1 region comprises a sequence of the formula (II):

wherein
FGly' is the modified amino acid residue of formula (I);
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the conjugate, $X^1$ is present; and
$X^2$ and $X^3$ are each independently any amino acid, and wherein the sequence is C-terminal to the amino acid sequence SWNSGA (SEQ ID NO: 46) and/or is N-terminal to the amino acid sequence GVHTFP (SEQ ID NO: 47).

In some instances, the heavy chain CH1 region comprises the sequence SWNSGAL(FGly')TPSRGVHTFP (SEQ ID NO: 48).

In some instances, the conjugate includes the following, where:
$Z^{30}$ is selected from R, K, H, A, G, L, V, I, and P;
$X^1$ is selected from L, M, S, and V; and
$X^2$ and $X^3$ are each independently selected from S, T, A, V, G, and C.

In some instances, the modified amino acid residue is positioned in a heavy chain $CH_2$ region of the anti-CD25 antibody.

In some instances, the modified amino acid residue is positioned in a heavy chain $CH_3$ region of the anti-CD25 antibody.

Aspects of the present disclosure include a pharmaceutical composition comprising a conjugate according to the present disclosure, and a pharmaceutically-acceptable excipient.

Aspects of the present disclosure include a method comprising administering to a subject an effective amount of a conjugate according to the present disclosure.

Aspects of the present disclosure include a method of treating cancer in a subject. The method includes administering to the subject a therapeutically effective amount of a pharmaceutical composition comprising a conjugate according to the present disclosure, where the administering is effective to treat cancer in the subject.

In some instances, the cancer is a hematologic malignancy.

In some instances, the hematologic malignancy is leukemia. In some instances, the leukemia is acute myeloid leukemia (AML). In some instances, the AML is refractory AML.

In some instances, the hematologic malignancy is lymphoma. In some instances, the lymphoma is Hodgkin lymphoma (HL). In some instances, the lymphoma is Non-Hodgkin lymphoma (NHL).

Aspects of the present disclosure include a method of reducing inhibitory signals derived from T regulatory cells in a subject. The method includes administering to the subject a therapeutically effective amount of a pharmaceutical composition comprising a conjugate according to the present disclosure, where the administering is effective to reduce inhibitory signals derived from T regulatory cells in the subject.

Aspects of the present disclosure include a method of delivering a drug to a target site in a subject. The method includes administering to the subject a pharmaceutical composition comprising a conjugate according to the present disclosure, where the administering is effective to release a therapeutically effective amount of the drug from the conjugate at the target site in the subject.

Aspects of the present disclosure include an anti-CD25 antibody comprising a formylglycine (FGly) residue.

In some instances, the anti-CD25 antibody comprises the sequence:

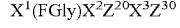

wherein
$Z^{20}$ is either a proline or alanine residue;
$Z^{30}$ is a basic amino acid or an aliphatic amino acid;
$X^1$ may be present or absent and, when present, can be any amino acid, with the proviso that when the sequence is at the N-terminus of the antibody, $X^1$ is present; and
$X^2$ and $X^3$ are each independently any amino acid.

In some instances, the sequence is L(FGly)TPSR (SEQ ID NO: 144).

In some instances, the anti-CD25 antibody includes the following, where:
- $Z^{30}$ is selected from R, K, H, A, G, L, V, I, and P;
- $X^1$ is selected from L, M, S, and V; and
- $X^2$ and $X^3$ are each independently selected from S, T, A, V, G, and C.

In some instances, the the sequence is at a C-terminus of a heavy chain constant region of the anti-CD25 antibody.

In some instances, the heavy chain constant region comprises the sequence:

$$X^1(FGly)X^2Z^{20}X^3Z^{30}$$

wherein
- $Z^{20}$ is either a proline or alanine residue;
- $Z^{30}$ is a basic amino acid or an aliphatic amino acid;
- $X^1$ may be present or absent and, when present, can be any amino acid, with the proviso that when the sequence is at the N-terminus of the conjugate, $X^1$ is present; and
- $X^2$ and $X^3$ are each independently any amino acid,
- wherein the sequence is C-terminal to the amino acid sequence SLSLSPG (SEQ ID NO: 145).

In some instances, the heavy chain constant region comprises the sequence SPGSL(FGly)TPSRGS (SEQ ID NO: 149).

In some instances, the anti-CD25 antibody includes the following, where:
- $Z^{30}$ is selected from R, K, H, A, G, L, V, I, and P;
- $X^1$ is selected from L, M, S, and V; and
- $X^2$ and $X^3$ are each independently selected from S, T, A, V, G, and C.

In some instances, the FGly residue is positioned in a light chain constant region of the anti-CD25 antibody.

In some instances, the light chain constant region comprises the sequence:

$$X^1(FGly)X^2Z^{20}X^3Z^{30} \quad (II)$$

wherein
- $Z^{20}$ is either a proline or alanine residue;
- $Z^{30}$ is a basic amino acid or an aliphatic amino acid;
- $X^1$ may be present or absent and, when present, can be any amino acid, with the proviso that when the sequence is at the N-terminus of the conjugate, $X^1$ is present; and
- $X^2$ and $X^3$ are each independently any amino acid, and
- wherein the sequence is C-terminal to the sequence KVDNAL (SEQ ID NO:42), and/or is N-terminal to the sequence QSGNSQ (SEQ ID NO: 43).

In some instances, the light chain constant region comprises the sequence KVDNAL(FGly)TPSRQSGNSQ (SEQ ID NO: 151).

In some instances, the anti-CD25 antibody includes the following, where:
- $Z^{30}$ is selected from R, K, H, A, G, L, V, I, and P;
- $X^1$ is selected from L, M, S, and V; and
- $X^2$ and $X^3$ are each independently selected from S, T, A, V, G, and C.

In some instances, the FGly residue is positioned in a heavy chain CH1 region of the anti-CD25 antibody.

In some instances, the heavy chain CH1 region comprises the sequence:

$$X^1(FGly)X^2Z^{20}X^3Z^{30}$$

wherein
- $Z^{20}$ is either a proline or alanine residue;
- $Z^{30}$ is a basic amino acid or an aliphatic amino acid;
- $X^1$ may be present or absent and, when present, can be any amino acid, with the proviso that when the sequence is at the N-terminus of the conjugate, $X^1$ is present; and
- $X^2$ and $X^3$ are each independently any amino acid, and
- wherein the sequence is C-terminal to the amino acid sequence SWNSGA (SEQ ID NO: 46) and/or is N-terminal to the amino acid sequence GVHTFP (SEQ ID NO: 47).

In some instances, the heavy chain CH1 region comprises the sequence SWNSGAL(FGly)TPSRGVHTFP (SEQ ID NO: 48).

In some instances, the anti-CD25 antibody includes the following, where:
- $Z^{30}$ is selected from R, K, H, A, G, L, V, I, and P;
- $X^1$ is selected from L, M, S, and V; and
- $X^2$ and $X^3$ are each independently selected from S, T, A, V, G, and C.

In some instances, the FGly residue is positioned in a heavy chain $CH_2$ region of the anti-CD25 antibody.

In some instances, the FGly residue is positioned in a heavy chain $CH_3$ region of the anti-CD25 antibody.

Aspects of the present disclosure include a cell comprising the anti-CD25 antibody according to the present disclosure.

Aspects of the present disclosure include a nucleic acid encoding the anti-CD25 antibody according to the present disclosure. Aspects of the present disclosure also include an expression vector comprising the nucleic acid. Aspects of the present disclosure also include a host cell comprising the nucleic acid or the expression vector.

BRIEF DESCRIPTION OF THE DRAWINGS

FIG. 1, panel B, shows antibodies carrying aldehyde moieties (2 per antibody) reacted with a Hydrazino-iso-Pictet-Spengler (HIPS) linker and payload to generate a site-specifically conjugated ADC. FIG. 1, panel C, shows HIPS chemistry, which proceeds through an intermediate hydrazonium ion followed by intramolecular alkylation with a nucleophilic indole to generate a stable C=C bond.

FIG. 12A depicts a site map showing possible modification sites for generation of an aldehyde tagged Ig polypeptide. The upper sequence is the amino acid sequence of the conserved region of an IgG1 light chain polypeptide (SEQ ID NO:162) and shows possible modification sites in an Ig light chain; the lower sequence is the amino acid sequence of the conserved region of an Ig heavy chain polypeptide (SEQ ID NO:163; GenBank Accession No. AAG00909) and shows possible modification sites in an Ig heavy chain. The heavy and light chain numbering is based on the full-length heavy and light chains.

FIG. 12B depicts an alignment of immunoglobulin heavy chain constant regions for IgG1 (SEQ ID NO:164), IgG2 (SEQ ID NO:165), IgG3 (SEQ ID NO:166), IgG4 (SEQ ID NO:167), and IgA (SEQ ID NO:168), showing modification sites at which aldehyde tags can be provided in an immunoglobulin heavy chain. The heavy and light chain numbering is based on the full-heavy and light chains.

FIG. 12C depicts an alignment of immunoglobulin light chain constant regions (SEQ ID NOs:162 and 170-173), showing modification sites at which aldehyde tags can be provided in an immunoglobulin light chain.

DEFINITIONS

Figure 1:
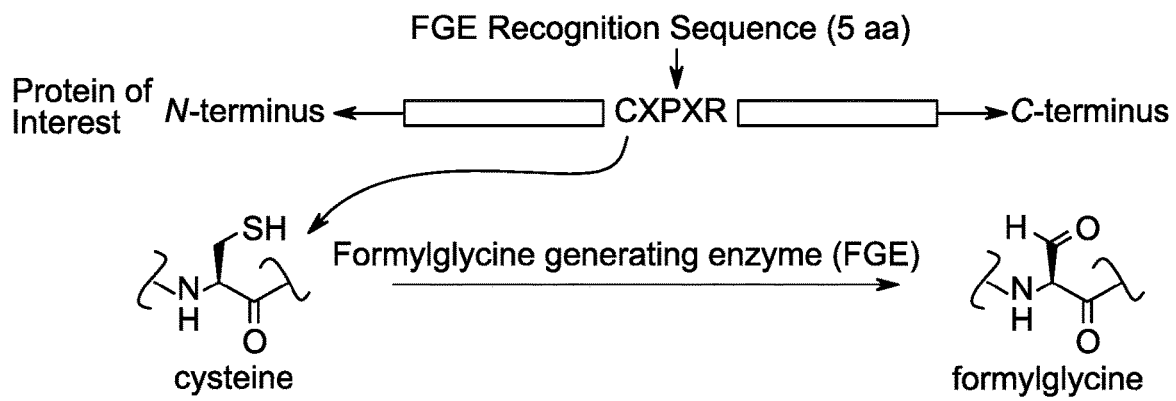
FIG. 1, panel A, shows a formylglycine-generating enzyme (FGE) recognition sequence inserted at the desired location along the antibody backbone using standard molecular biology techniques. Upon expression, FGE, which is endogenous to eukaryotic cells, catalyzes the conversion of the Cys within the consensus sequence to a formylglycine residue (FGly).
Figure 1:
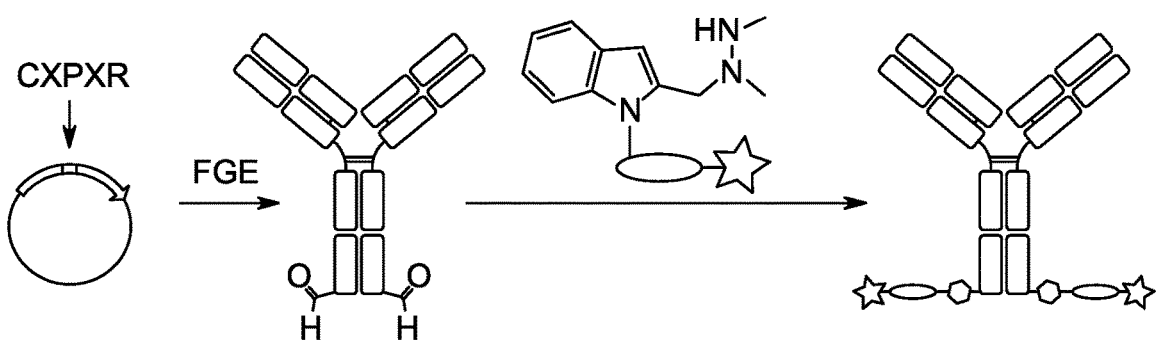
Figure 1:
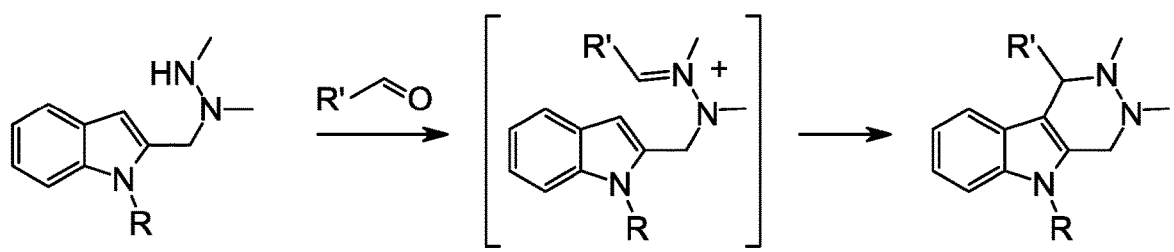

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

Throughout the present disclosure, the numbering of the residues in an immunoglobulin heavy chain and in an immunoglobulin light chain is that as in Kabat et al., Sequences of Proteins of Immunological Interest, 5th Ed. Public Health Service, National Institutes of Health, Bethesda, Md. (1991), expressly incorporated herein by reference.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a μ or an ε heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins begin immediately after (C-terminal to) the light chain variable (VL) region, and is about 100 amino acids to 120 amino acids in length.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell, e.g., a mammalian host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (FGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides anti-CD25 antibody-maytansine conjugate structures. The disclosure also encompasses methods of production of such conjugates, as well as methods of using the same. Embodiments of each are described in more detail in the sections below.

Antibody-Drug Conjugates

The present disclosure provides conjugates, e.g., antibody-drug conjugates. By "conjugate" is meant a first moiety (e.g., an antibody) is stably associated with a second moiety (e.g., a drug). For example, a maytansine conjugate includes a maytansine (e.g., a maytansine active agent moiety) stably associated with another moiety (e.g., the antibody). By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. In certain embodiments, the moiety conjugated to the polypeptide can be any of a variety of moieties of interest such as, but not limited to, a detectable label, a drug, a water-soluble polymer, or a moiety for immobilization of the polypeptide to a membrane or a surface. In certain embodiments, the conjugate is a maytansine conjugate, where a polypeptide is conjugated to a maytansine or a maytansine active agent moiety. "Maytansine", "maytansine moiety", "maytansine active agent moiety" and "maytansinoid" refer to a maytansine and analogs and derivatives thereof, and pharmaceutically active maytansine moieties and/or portions thereof. A maytansine conjugated to the polypeptide can be any of a variety of maytansinoid moieties such as, but not limited to, maytansine and analogs and derivatives thereof as described herein.

The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

In certain embodiments, a conjugate of the present disclosure includes a maytansine conjugated to an amino acid reside of a polypeptide at the α-carbon of an amino acid residue. Stated another way, a maytansine conjugate includes a polypeptide where the side chain of one or more amino acid residues in the polypeptide have been modified to be attached to a maytansine (e.g., attached to a maytansine through a linker as described herein). For example, a maytansine conjugate includes a polypeptide where the α-carbon of one or more amino acid residues in the polypeptide has been modified to be attached to a maytansine (e.g., attached to a maytansine through a linker as described herein).

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues of the polypeptide that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

As described herein, a polypeptide may be conjugated to one or more moieties. In certain embodiments, the moiety of interest is a chemical entity, such as a drug or a detectable label. For example, a drug (e.g., maytansine) may be conjugated to the polypeptide, or in other embodiments, a detectable label may be conjugated to the polypeptide. Thus, for instance, embodiments of the present disclosure include, but are not limited to, the following: a conjugate of a polypeptide and a drug; a conjugate of a polypeptide and a detectable label; a conjugate of two or more drugs and a polypeptide; a conjugate of two or more detectable labels and a polypeptide; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest (e.g., a drug, such as maytansine) together through the coupling moiety. In some cases, the coupling moiety includes a hydrazinyl-indolyl or a hydrazinyl-pyrrolo-pyridinyl compound, or a derivative of a hydrazinyl-indolyl or a hydrazinyl-pyrrolo-pyridinyl compound. For instance, a general scheme for coupling a moiety of interest (e.g., a maytansine) to a polypeptide through a hydrazinyl-indolyl or a hydrazinyl-pyrrolo-pyridinyl coupling moiety is shown in the general reaction scheme below. Hydrazinyl-indolyl and hydrazinyl-pyrrolo-pyridinyl coupling moiety are also referred to herein as a hydrazino-iso-Pictet-Spengler (HIPS) coupling moiety and an aza-hydrazino-iso-Pictet-Spengler (azaHIPS) coupling moiety, respectively.

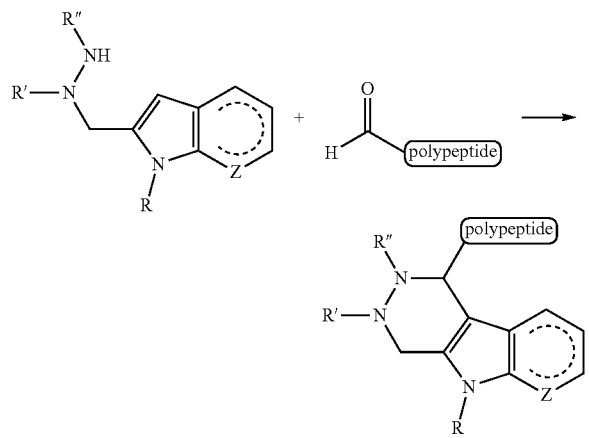

In the reaction scheme above, R is the moiety of interest (e.g., maytansine) that is conjugated to the polypeptide. As shown in the reaction scheme above, a polypeptide that includes a 2-formylglycine residue (fGly) is reacted with a drug (e.g., maytansine) that has been modified to include a coupling moiety (e.g., a hydrazinyl-indolyl or a hydrazinyl-pyrrolo-pyridinyl coupling moiety) to produce a polypeptide conjugate attached to the coupling moiety, thus attaching the maytansine to the polypeptide through the coupling moiety.

As described herein, the moiety can be any of a variety of moieties such as, but not limited to, chemical entity, such as a detectable label, or a drug (e.g., a maytansinoid). R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Z may be $CR^{11}$, $NR^{12}$, N, O or S, where $R^{11}$ and $R^{12}$ are each independently selected from any of the substituents described for R' and R" above.

Other hydrazinyl-indolyl or hydrazinyl-pyrrolo-pyridinyl coupling moieties are also possible, as shown in the conjugates and compounds described herein. For example, the hydrazinyl-indolyl or hydrazinyl-pyrrolo-pyridinyl coupling moieties may be modified to be attached (e.g., covalently attached) to a linker. As such, embodiments of the present disclosure include a hydrazinyl-indolyl or hydrazinyl-pyrrolo-pyridinyl coupling moiety attached to a drug (e.g., maytansine) through a linker. Various embodiments of the linker that may couple the hydrazinyl-indolyl or hydrazinyl-pyrrolo-pyridinyl coupling moiety to the drug (e.g., maytansine) are described in detail herein.

In certain embodiments, the polypeptide may be conjugated to a moiety of interest, where the polypeptide is modified before conjugation to the moiety of interest. Modification of the polypeptide may produce a modified polypeptide that contains one or more reactive groups suitable for conjugation to the moiety of interest. In some cases, the polypeptide may be modified at one or more amino acid residues to provide one or more reactive groups suitable for conjugation to the moiety of interest (e.g., a moiety that includes a coupling moiety, such as a hydrazinyl-indolyl or a hydrazinyl-pyrrolo-pyridinyl coupling moiety as described above). For example, the polypeptide may be modified to include a reactive aldehyde group (e.g., a reactive aldehyde). A reactive aldehyde may be included in an "aldehyde tag" or "ald-tag", which as used herein refers to an amino acid sequence derived from a sulfatase motif (e.g., L(C/S)TPSR) (SEQ ID NO: 154) that has been converted by action of a formylglycine generating enzyme (FGE) to contain a 2-formylglycine residue (referred to herein as "FGly"). The FGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to FGly by action of an FGE, e.g., L(FGly)TPSR) (SEQ ID NO: 144). A converted sulfatase motif may be derived from an amino acid sequence that includes an "unconverted" sulfatase motif (i.e., a sulfatase motif in which the cysteine or serine residue has not been converted to FGly by an FGE, but is capable of being converted, e.g., an unconverted sulfatase motif with the sequence: L(C/S)TPSR) (SEQ ID NO: 154). By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly). Additional aspects of aldehyde tags and uses thereof in site-specific protein modification are described in U.S. Pat. Nos. 7,985,783 and 8,729,232, the disclosures of each of which are incorporated herein by reference.

In some cases, the modified polypeptide containing the FGly residue may be conjugated to the moiety of interest by reaction of the FGly with a compound (e.g., a compound containing a hydrazinyl-indolyl or a hydrazinyl-pyrrolo-pyridinyl coupling moiety, as described above). For example, an FGly-containing polypeptide may be contacted with a reactive partner-containing drug under conditions suitable to provide for conjugation of the drug to the polypeptide. In some instances, the reactive partner-containing drug may include a hydrazinyl-indolyl or a hydrazinyl-pyrrolo-pyridinyl coupling moiety as described above. For example, a maytansine may be modified to include a hydrazinyl-indolyl or a hydrazinyl-pyrrolo-pyridinyl coupling moiety. In some cases, the maytansine is attached to a hydrazinyl-indolyl or a hydrazinyl-pyrrolo-pyridinyl, such as covalently attached to a a hydrazinyl-indolyl or a hydrazinyl-pyrrolo-pyridinyl through a linker, as described in detail herein.

In certain embodiments, a conjugate of the present disclosure includes a polypeptide (e.g., an antibody, such as an anti-CD25 antibody) having at least one modified amino acid residue. The modified amino acid residue of the polypeptide may be coupled to a drug (e.g., maytansine) containing a hydrazinyl-indolyl or a hydrazinyl-pyrrolo-pyridinyl coupling moiety as described above. In certain embodiments, the modified amino acid residue of the polypeptide (e.g., anti-CD25 antibody) may be derived from a cysteine or serine residue that has been converted to an FGly residue as described above. In certain embodiments, the FGly residue is conjugated to a drug containing a hydrazinyl-indolyl or a hydrazinyl-pyrrolo-pyridinyl coupling moiety as described above to provide a conjugate of the present disclosure where the drug is conjugated to the polypeptide through the hydrazinyl-indolyl or hydrazinyl-pyrrolopyridinyl coupling moiety. As used herein, the term FGly' refers to the modified amino acid residue of the polypeptide (e.g., anti-CD25 antibody) that is coupled to the moiety of interest (e.g., a drug, such as a maytansine).

In certain embodiments, the conjugate includes at least one modified amino acid residue of the formula (I) described herein. For instance, the conjugate may include at least one modified amino acid residue with a side chain of the formula (I):

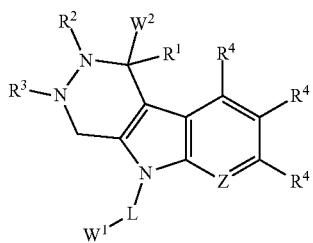

(I)

wherein
Z is $CR^4$ or N;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
L is a linker comprising $-(T^1-V^1)_a-(T^2-V^2)_b-(T^3-V^3)_c-(T^4-V^4)_d-$, wherein a, b, c and d are each independently 0 or 1, where the sum of a, b, c and d is 1 to 4;
$T^1$, $T^2$, $T^3$ and $T^4$ are each independently selected from $(C_1-C_{12})$alkyl, substituted $(C_1-C_{12})$alkyl, $(EDA)_w$, $(PEG)_n$, $(AA)_p$, $-(CR^{13}OH)_h-$, piperidin-4-amino (4AP), an acetal group, a hydrazine, a disulfide, and an ester, wherein EDA is an ethylene diamine moiety, PEG is a polyethylene glycol or a modified polyethylene glycol, and AA is an amino acid residue, wherein w is an integer from 1 to 20, n is an integer from 1 to 30, p is an integer from 1 to 20, and h is an integer from 1 to 12;
$V^1$, $V^2$, $V^3$ and $V^4$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein q is an integer from 1 to 6;
each $R^{13}$ is independently selected from hydrogen, an alkyl, a substituted alkyl, an aryl, and a substituted aryl;
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl; $W^1$ is a maytansinoid; and
$W^2$ is an anti-CD25 antibody.

In certain embodiments, Z is $CR^4$ or N. In certain embodiments, Z is $CR^4$. In certain embodiments, Z is N.

In certain embodiments, $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^1$ is methyl. In certain embodiments, $R^1$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is alkynyl or substituted alkynyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-8}$ cycloalkyl or $C_{3-5}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^1$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is methyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is methyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are optionally cyclically linked to form a 5 or 6-membered heterocyclyl. In certain embodiments, $R^2$ and $R^3$ are cyclically linked to form a 5 or 6-membered heterocyclyl. In certain embodiments, $R^2$ and $R^3$ are cyclically linked to form a 5-membered heterocyclyl. In certain embodiments, $R^2$ and $R^3$ are cyclically linked to form a 6-membered heterocyclyl.

In certain embodiments, each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^4$ are described in more detail as follows. In certain embodiments, $R^4$ is hydrogen. In certain embodiments, each $R^4$ is hydrogen. In certain embodiments, $R^4$ is halogen, such as F, Cl, Br or I. In certain embodiments, $R^4$ is F. In certain embodiments, $R^4$ is Cl. In certain embodiments, $R^4$ is Br. In certain embodiments, $R^4$ is I. In certain embodiments, $R^4$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^4$ is methyl. In certain embodiments, $R^4$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^4$ is alkynyl or substituted alkynyl. In certain embodiments, $R^4$ is alkoxy or substituted alkoxy. In certain embodiments, $R^4$ is amino or substituted amino. In certain embodiments, $R^4$ is carboxyl or carboxyl ester. In certain embodiments, $R^4$ is acyl or acyloxy. In certain embodiments, $R^4$ is acyl amino or amino acyl. In certain embodiments, $R^4$ is alkylamide or substituted alkylamide. In certain embodiments, $R^4$ is sulfonyl. In certain embodiments, $R^4$ is thioalkoxy or substituted thioalkoxy. In certain embodiments, $R^4$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^4$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^4$ is cycloalkyl or substituted cycloalkyl, such as $C_{3-8}$ cycloalkyl or $C_{3-8}$ substituted cycloalkyl, such as a $C_{3-6}$ cycloalkyl or $C_3$-6 substituted cycloalkyl, or a $C_{3-5}$ cycloalkyl or $C_{3-8}$ substituted cycloalkyl. In certain embodiments, $R^4$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $W^1$ is a maytansinoid. Further description of the maytansinoid is found in the disclosure herein.

In certain embodiments, $W^2$ is an anti-CD25 antibody. Further description of anti-CD25 antibodies that find use in the subject conjugates is found in the disclosure herein.

In certain embodiments, the compounds of formula (I) include a linker, L. The linker may be utilized to bind a coupling moiety to one or more moieties of interest and/or one or more polypeptides. In some embodiments, the linker binds a coupling moiety to either a polypeptide or a chemical entity. The linker may be bound (e.g., covalently bonded) to the coupling moiety (e.g., as described herein) at any convenient position. For example, the linker may attach a hydrazinyl-indolyl or a hydrazinyl-pyrrolo-pyridinyl coupling moiety to a drug (e.g., a maytansine). The hydrazinyl-indolyl or hydrazinyl-pyrrolo-pyridinyl coupling moiety may be used to conjugate the linker (and thus the drug, e.g., maytansine) to a polypeptide, such as an anti-CD25 antibody. For example, the coupling moiety may be used to conjugate the linker (and thus the drug, e.g., maytansine) to a modified amino acid residue of the polypeptide, such as an FGly reside of an anti-CD25 antibody.

In certain embodiments, L attaches the coupling moiety to $W^1$, and thus the coupling moiety is indirectly bonded to $W^1$ through the linker L. As described above, $W^1$ is a maytansinoid, and thus L attaches the coupling moiety to a maytansinoid, e.g., the coupling moiety is indirectly bonded to the maytansinoid through the linker, L.

Any convenient linkers may be utilized in the subject conjugates and compounds. In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, L is a linker described by the formula $-(L^1)_a-(L^2)_b-(L^3)_c-(L^4)_d-$, wherein $L^1$, $L^2$, $L^3$ and $L^4$ are each independently a linker unit, and a, b, c and d are each independently 0 or 1, wherein the sum of a, b, c and d is 1 to 4.

In certain embodiments, the sum of a, b, c and d is 1. In certain embodiments, the sum of a, b, c and d is 2. In certain embodiments, the sum of a, b, c and d is 3. In certain embodiments, the sum of a, b, c and d is 4. In certain embodiments, a, b, c and d are each 1. In certain embodiments, a, b and c are each 1 and d is 0. In certain embodiments, a and b are each 1 and c and d are each 0. In certain embodiments, a is 1 and b, c and d are each 0.

In certain embodiments, $L^1$ is attached to the hydrazinyl-indolyl or the hydrazinyl-pyrrolo-pyridinyl coupling moiety (e.g., as shown in formula (I) above). In certain embodiments, $L^2$, if present, is attached to $W^1$. In certain embodiments, $L^3$, if present, is attached to $W^1$. In certain embodiments, $L^4$, if present, is attached to $W^1$.

Any convenient linker units may be utilized in the subject linkers. Linker units of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^1$, $L^2$, $L^3$ and $L^4$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^1$ (if present) comprises a polyethylene glycol, a modified polyethylene glycol, an amino acid residue, an alkyl group, a substituted alkyl, an aryl group, a substituted aryl group, or a diamine. In some embodiments, $L^1$ comprises a polyethylene glycol. In some embodiments, $L^1$ comprises a modified polyethylene glycol. In some embodiments, Li comprises an amino acid residue. In some embodiments, $L^1$ comprises an alkyl group or a substituted alkyl. In some embodiments, $L^1$ comprises an aryl group or a substituted aryl group. In some embodiments, $L^1$ comprises a diamine (e.g., a linking group comprising an alkylene diamine).

In some embodiments, $L^2$ (if present) comprises a polyethylene glycol, a modified polyethylene glycol, an amino acid residue, an alkyl group, a substituted alkyl, an aryl group, a substituted aryl group, or a diamine. In some embodiments, $L^2$ comprises a polyethylene glycol. In some embodiments, $L^2$ comprises a modified polyethylene glycol. In some embodiments, $L^2$ comprises an amino acid residue. In some embodiments, $L^2$ comprises an alkyl group or a substituted alkyl. In some embodiments, $L^2$ comprises an aryl group or a substituted aryl group. In some embodiments, $L^2$ comprises a diamine (e.g., a linking group comprising an alkylene diamine).

In some embodiments, $L^3$ (if present) comprises a polyethylene glycol, a modified polyethylene glycol, an amino acid residue, an alkyl group, a substituted alkyl, an aryl group, a substituted aryl group, or a diamine. In some embodiments, $L^3$ comprises a polyethylene glycol. In some embodiments, $L^3$ comprises a modified polyethylene glycol. In some embodiments, $L^3$ comprises an amino acid residue. In some embodiments, $L^3$ comprises an alkyl group or a substituted alkyl. In some embodiments, $L^3$ comprises an aryl group or a substituted aryl group. In some embodiments, $L^3$ comprises a diamine (e.g., a linking group comprising an alkylene diamine).

In some embodiments, $L^4$ (if present) comprises a polyethylene glycol, a modified polyethylene glycol, an amino acid residue, an alkyl group, a substituted alkyl, an aryl group, a substituted aryl group, or a diamine. In some embodiments, $L^4$ comprises a polyethylene glycol. In some embodiments, $L^4$ comprises a modified polyethylene glycol. In some embodiments, $L^4$ comprises an amino acid residue. In some embodiments, $L^4$ comprises an alkyl group or a substituted alkyl. In some embodiments, $L^4$ comprises an aryl group or a substituted aryl group. In some embodiments, $L^4$ comprises a diamine (e.g., a linking group comprising an alkylene diamine).

In some embodiments, L is a linker comprising $-(L^1)_a$-$(L^2)_b$-$(L^3)_c$-$(L^4)_d$-, where:
  $(L^1)_a$- is $-(T^1-V^1)_a$-;
  $(L^2)_b$- is $-(T^2-V^2)_b$-;
  $(L^3)_c$- is $-(T^3-V^3)_c$-; and
  $(L^4)_d$- is $-(T^4-V^4)_d$-,
  wherein $T^1$, $T^2$, $T^3$ and $T^4$, if present, are tether groups;
  $V^1$, $V^2$, $V^3$ and $V^4$, if present, are covalent bonds or linking functional groups; and
  a, b, c and d are each independently 0 or 1, wherein the sum of a, b, c and d is 1 to 4.

As described above, in certain embodiments, $L^1$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to $W^1$ (the maytansinoid). In certain embodiments, $L^2$, if present, is attached to $W^1$. As such, in certain embodiments, $T^2$, if present, is attached to $W^1$, or $V^2$, if present, is attached to $W^1$. In certain embodiments, $L^3$, if present, is attached to $W^1$. As such, in certain embodiments, $T^3$, if present, is attached to $W^1$, or $V^3$, if present, is attached to $W^1$. In certain embodiments, $L^4$, if present, is attached to $W^1$. As such, in certain embodiments, $T^4$, if present, is attached to $W^1$, or $V^4$, if present, is attached to $W^1$.

Regarding the tether groups, $T^1$, $T^2$, $T^3$ and $T^4$, any convenient tether groups may be utilized in the subject linkers. In some embodiments, $T^1$, $T^2$, $T^3$ and $T^4$ each comprise one or more groups independently selected from a $(C_1-C_{12})$alkyl, a substituted $(C_1-C_{12})$alkyl, an $(EDA)_w$, $(PEG)_n$, $(AA)_p$, $-(CR^{13}OH)_h-$, piperidin-4-amino (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, when the sum of a, b, c and d is 2 and one of $T^1-V^1$, $T^2-V^2$, $T^3-V^3$, or $T^4-V^4$ is $(PEG)_n$-CO, then n is not 6. For example, in some instances, the linker may have the following structure:

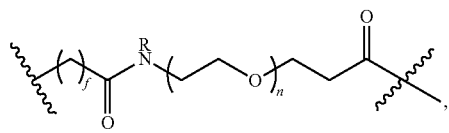

where n is not 6.

In certain embodiments, when the sum of a, b, c and d is 2 and one of $T^1-V^1$, $T^2-V^2$, $T^3-V^3$, or $T^4-V^4$ is $(C_1-C_{12})$alkyl-$NR^{15}$, then $(C_1-C_{12})$alkyl is not a $C_5$-alkyl. For example, in some instances, the linker may have the following structure:

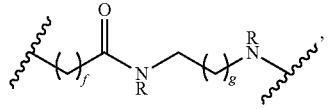

where g is not 4.

In certain embodiments, the tether group (e.g., $T^1$, $T^2$, $T^3$ and/or $T^4$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene.

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene.

In certain embodiments, the tether group (e.g., $T^1$, $T^2$, $T^3$ and/or $T^4$) includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

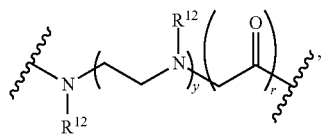

where y is an integer from 1 to 6, r is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group includes a 4-amino-piperidine (4AP) moiety (also referred to herein as piperidin-4-amino, P4A). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

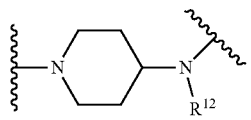

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

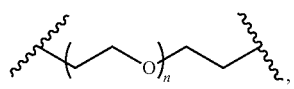

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^1$, $T^2$, $T^3$ and/or $T^4$) includes $(PEG)_n$, where $(PEG)_n$ is a polyethylene glycol or a modified polyethylene glycol linking unit. In certain embodiments, $(PEG)_n$ is described by the structure:

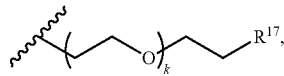

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^1$, $T^2$, $T^3$ and/or $T^4$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^1$, $T^2$, $T^3$ and/or $T^4$) includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^1$, $V^2$, $V^3$ and $V^4$, any convenient linking functional groups may be utilized in the subject linkers. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{15}$ are described in more detail as follows. In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, L is a linker comprising -(T$^1$-V$^1$)$_a$-(T$^2$-V$^2$)$_b$-(T$^3$-V$^3$)$_c$-(T$^4$-V$^4$)$_d$-, where a, b, c and d are each independently 0 or 1, where the sum of a, b, c and d is 1 to 4.

In some embodiments, in the subject linker:
T$^1$ is selected from a (C$_1$-C$_{12}$)alkyl and a substituted (C$_1$-C$_{12}$)alkyl;
T$^2$, T$^3$ and T$^4$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, 4-amino-piperidine (4AP), an acetal group, a disulfide, a hydrazine, and an ester; and
V$^1$, V$^2$, V$^3$ and V$^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

wherein:
(PEG)$_n$ is

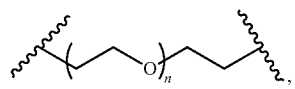

n where n is an integer from 1 to 30;
EDA is an ethylene diamine moiety having the following structure:

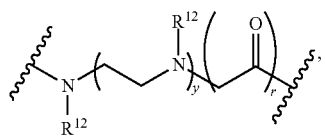

where y is an integer from 1 to 6 and r is 0 or 1;
4-amino-piperidine (4AP) is

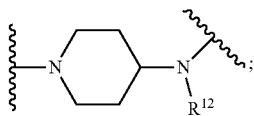

AA is an amino acid residue, where p is an integer from 1 to 20; and each $R^{15}$ and $R^{12}$ is independently selected from hydrogen, an alkyl, a substituted alkyl, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$ and $V^1$, $V^2$, $V^3$ and $V^4$ are selected from the following table, e.g., one row of the following table:

TABLE 2

| $T^1$ | $V^1$ | $T^2$ | $V^2$ | $T^3$ | $V^3$ | $T^4$ | $V^4$ |
|---|---|---|---|---|---|---|---|
| $(C_1-C_{12})$alkyl | —CONR$^{15}$— | (PEG)$_n$ | —CO— | — | — | — | — |
| $(C_1-C_{12})$alkyl | —CO— | (AA)$_p$ | —NR$^{15}$— | (PEG)$_n$ | —CO— | — | — |
| $(C_1-C_{12})$alkyl | —CO— | (AA)$_p$ | — | — | — | — | — |
| $(C_1-C_{12})$alkyl | —CONR$^{15}$— | (PEG)$_n$ | —NR$^{15}$— | — | — | — | — |
| $(C_1-C_{12})$alkyl | —CO— | (AA)$_p$ | —NR$^{15}$— | (PEG)$_n$ | —NR$^{15}$— | — | — |
| $(C_1-C_{12})$alkyl | —CO— | (EDA)$_w$ | —CO— | — | — | — | — |
| $(C_1-C_{12})$alkyl | —CONR$^{15}$— | $(C_1-C_{12})$alkyl | —NR$^{15}$— | — | — | — | — |
| $(C_1-C_{12})$alkyl | —CONR$^{15}$— | (PEG)$_n$ | —CO— | (EDA)$_w$ | — | — | — |
| $(C_1-C_{12})$alkyl | —CO— | (EDA)$_w$ | — | — | — | — | — |
| $(C_1-C_{12})$alkyl | —CO— | (EDA)$_w$ | —CO— | (CR$^{13}$OH)$_h$ | —CONR$^{15}$— | $(C_1-C_{12})$alkyl | —CO— |
| $(C_1-C_{12})$alkyl | —CO— | (AA)$_p$ | —NR$^{15}$— | $(C_1-C_{12})$alkyl | —CO— | — | — |
| $(C_1-C_{12})$alkyl | —CONR$^{15}$— | (PEG)$_n$ | —CO— | (AA)$_p$ | — | — | — |
| $(C_1-C_{12})$alkyl | —CO— | (EDA)$_w$ | —CO— | (CR$^{13}$OH)$_h$ | —CO— | (AA)$_p$ | — |
| $(C_1-C_{12})$alkyl | —CO— | (AA)$_p$ | —NR$^{15}$— | $(C_1-C_{12})$alkyl | —CO— | (AA)$_p$ | — |
| $(C_1-C_{12})$alkyl | —CO— | (AA)$_p$ | —NR$^{15}$— | (PEG)$_n$ | —CO— | (AA)$_p$ | — |
| $(C_1-C_{12})$alkyl | —CO— | (AA)$_p$ | —NR$^{15}$— | (PEG)$_n$ | —SO$_2$— | (AA)$_p$ | — |
| $(C_1-C_{12})$alkyl | —CO— | (EDA)$_w$ | —CO— | (CR$^{13}$OH)$_h$ | —CONR$^{15}$— | (PEG)$_n$ | —CO— |
| $(C_1-C_{12})$alkyl | —CO— | (CR$^{13}$OH)$_h$ | —CO— | — | — | — | — |
| $(C_1-C_{12})$alkyl | —CONR$^{15}$— | substituted $(C_1-C_{12})$alkyl | —NR$^{15}$— | (PEG)$_n$ | —CO— | — | — |
| $(C_1-C_{12})$alkyl | —SO$_2$— | $(C_1-C_{12})$alkyl | —CO— | — | — | — | — |
| $(C_1-C_{12})$alkyl | —CONR$^{15}$— | $(C_1-C_{12})$alkyl | — | (CR$^{13}$OH)$_h$ | —CONR$^{15}$— | — | — |
| $(C_1-C_{12})$alkyl | —CO— | (AA)$_p$ | —NR$^{15}$— | (PEG)$_n$ | —CO— | (AA)$_p$ | —NR$^{15}$— |
| $(C_1-C_{12})$alkyl | —CO— | (AA)$_p$ | —NR$^{15}$— | (PEG)$_n$ | —P(O)OH— | (AA)$_p$ | — |
| $(C_1-C_{12})$alkyl | —CO— | (EDA)$_w$ | — | (AA)$_p$ | — | — | — |
| $(C_1-C_{12})$alkyl | —CONR$^{15}$— | $(C_1-C_{12})$alkyl | —NR$^{15}$— | — | —CO— | — | — |
| $(C_1-C_{12})$alkyl | —CONR$^{15}$— | $(C_1-C_{12})$alkyl | —NR$^{15}$— | — | —CO— | $(C_1-C_{12})$alkyl | —NR$^{15}$— |
| $(C_1-C_{12})$alkyl | —CO— | 4AP | —CO— | $(C_1-C_{12})$alkyl | —CO— | (AA)$_p$ | — |
| $(C_1-C_{12})$alkyl | —CO— | 4AP | —CO— | $(C_1-C_{12})$alkyl | —CO— | — | — |

In certain embodiments, L is a linker comprising -(L$^1$)$_a$-(L$^2$)$_b$-(L$^3$)$_c$-(L$^4$)$_d$-, where -(Li)$_a$- is -(T$^1$-V$^1$)$_a$-; -(L$^2$)$_b$- is -(T$^2$-V$^2$)$_b$-; -(L$^3$)$_c$- is -(T$^3$-V$^3$)$_c$-; and -(L$^4$)$_d$- is -(T$^4$-V$^4$)$_d$-.

In certain embodiments, $T^1$ is $(C_1-C_{12})$alkyl, $V^1$ is —CO—, $T^2$ is (AA)$_p$, $V^2$ is —NR$^{15}$—, $T^3$ is (PEG)$_n$, $V^3$ is —CO—, $T^4$ is absent and $V^4$ is absent.

In certain embodiments, $T^1$ is $(C_1-C_{12})$alkyl, $V^1$ is —CO—, $T^2$ is (EDA)$_w$, $V^2$ is —CO—, $T^3$ is (CR$^{13}$OH)$_h$, $V^3$ is —CONR$^{15}$—, $T^4$ is $(C_1-C_{12})$alkyl and $V^4$ is —CO—.

In certain embodiments, $T^1$ is $(C_1-C_{12})$alkyl, $V^1$ is —CO—, $T^2$ is (AA)$_p$, $V^2$ is —NR$^{15}$—, $T^3$ is $(C_1-C_{12})$alkyl, $V^3$ is —CO—, $T^4$ is absent and $V^4$ is absent.

In certain embodiments, $T^1$ is $(C_1-C_{12})$alkyl, $V^1$ is —CONR$^{15}$—, $T^2$ is (PEG)$_n$, $V^2$ is —CO—, $T^3$ is absent, $V^3$ is absent, $T^4$ is absent and $V^4$ is absent.

In certain embodiments, $T^1$ is $(C_1-C_{12})$alkyl, $V^1$ is —CO—, $T^2$ is (AA)$_p$, $V^2$ is absent, $T^3$ is absent, $V^3$ is absent, $T^4$ is absent and $V^4$ is absent.

In certain embodiments, $T^1$ is $(C_1-C_{12})$alkyl, $V^1$ is —CONR$^{15}$—, $T^2$ is (PEG)$_n$, $V^2$ is —NR$^{15}$—, $T^3$ is absent, $V^3$ is absent, $T^4$ is absent and $V^4$ is absent.

In certain embodiments, $T^1$ is $(C_1-C_{12})$alkyl, $V^1$ is —CO—, $T^2$ is (AA)$_p$, $V^2$ is —NR$^{15}$—, $T^3$ is (PEG)$_n$, $V^3$ is —NR$^{15}$—, $T^4$ is absent and $V^4$ is absent.

In certain embodiments, $T^1$ is $(C_1-C_{12})$alkyl, $V^1$ is —CO—, $T^2$ is (EDA)$_w$, $V^2$ is —CO—, $T^3$ is absent, $V^3$ is absent, $T^4$ is absent and $V^4$ is absent.

In certain embodiments, $T^1$ is $(C_1-C_{12})$alkyl, $V^1$ is —CONR$^{15}$—, $T^2$ is $(C_1-C_{12})$alkyl, $V^2$ is —NR$^{15}$—, $T^3$ is absent, $V^3$ is absent, $T^4$ is absent and $V^4$ is absent.

In certain embodiments, $T^1$ is $(C_1-C_{12})$alkyl, $V^1$ is —CONR$^{15}$—, $T^2$ is (PEG)$_n$, $V^2$ is —CO—, $T^3$ is (EDA)$_w$, $V^3$ is absent, $T^4$ is absent and $V^4$ is absent.

In certain embodiments, $T^1$ is $(C_1-C_{12})$alkyl, $V^1$ is —CO—, $T^2$ is (EDA)$_w$, $V^2$ is absent, $T^3$ is absent, $V^3$ is absent, $T^4$ is absent and $V^4$ is absent.

In certain embodiments, $T^1$ is $(C_1-C_{12})$alkyl, $V^1$ is —CONR$^{15}$—, $T^2$ is (PEG)$_n$, $V^2$ is —CO—, $T^3$ is (AA)$_p$, $V^3$ is absent, $T^4$ is absent and $V^4$ is absent.

In certain embodiments, $T^1$ is $(C_1-C_{12})$alkyl, $V^1$ is —CO—, $T^2$ is (EDA)$_w$, $V^2$ is —CO—, $T^3$ is (CR$^{13}$OH)$_h$, $V^3$ is —CO—, $T^4$ is (AA)$_p$ and $V^4$ is absent.

In certain embodiments, $T^1$ is $(C_1-C_{12})$alkyl, $V^1$ is —CO—, $T^2$ is (AA)$_p$, $V^2$ is —NR$^{15}$—, $T^3$ is $(C_1-C_{12})$alkyl, $V^3$ is —CO—, $T^4$ is (AA)$_p$ and $V^4$ is absent.

In certain embodiments, $T^1$ is $(C_1-C_{12})$alkyl, $V^1$ is —CO—, $T^2$ is (AA)$_p$, $V^2$ is —NR$^{15}$—, $T^3$ is (PEG)$_n$, $V^3$ is —CO—, $T^4$ is (AA)$_p$ and $V^4$ is absent.

In certain embodiments, $T^1$ is $(C_1-C_{12})$alkyl, $V^1$ is —CO—, $T^2$ is (AA)$_p$, $V^2$ is —NR$^{11}$—, $T^3$ is (PEG)$_n$, $V^3$ is —SO$_2$—, $T^4$ is (AA)$_p$ and $V^4$ is absent.

In certain embodiments, $T^1$ is $(C_1-C_{12})$alkyl, $V^1$ is —CO—, $T^2$ is (EDA)$_w$, $V^2$ is —CO—, $T^3$ is (CR$^{13}$OH)$_h$, $V^3$ is —CONR$^{15}$—, $T^4$ is (PEG)$_n$ and $V^4$ is —CO—.

In certain embodiments, $T^1$ is $(C_1-C_{12})$alkyl, $V^1$ is —CO—, $T^2$ is (CR$^{13}$OH)$_h$, $V^2$ is —CO—, $T^3$ is absent, $V^3$ is absent, $T^4$ is absent and $V^4$ is absent.

In certain embodiments, $T^1$ is $(C_1-C_{12})$alkyl, $V^1$ is —CONR$^{15}$—, $T^2$ is substituted $(C_1-C_{12})$alkyl, $V^2$ is —NR$^{15}$—, $T^3$ is (PEG)$_n$, $V^3$ is —CO—, $T^4$ is absent and $V^4$ is absent.

In certain embodiments, $T^1$ is $(C_1\text{-}C_{12})$alkyl, $V^1$ is $-SO_2-$, $T^2$ is $(C_1\text{-}C_{12})$alkyl, $V^2$ is $-CO-$, $T^3$ is absent, $V^3$ is absent, $T^4$ is absent and $V^4$ is absent.

In certain embodiments, $T^1$ is $(C_1\text{-}C_{12})$alkyl, $V^1$ is $-CONR^{15}-$, $T^2$ is $(C_1\text{-}C_{12})$alkyl, $V^2$ is absent, $T^3$ is $(CR^{13}OH)_h$, $V^3$ is $-CONR^{15}-$, $T^4$ is absent and $V^4$ is absent.

In certain embodiments, $T^1$ is $(C_1\text{-}C_{12})$alkyl, $V^1$ is $-CO-$, $T^2$ is $(AA)_p$, $V^2$ is $-NR^{15}-$, $T^3$ is $(PEG)_n$, $V^3$ is $-CO-$, $T^4$ is $(AA)_p$ and $V^4$ is $-NR^{15}-$.

In certain embodiments, $T^1$ is $(C_1\text{-}C_{12})$alkyl, $V^1$ is $-CO-$, $T^2$ is $(AA)_p$, $V^2$ is $-NR^{15}-$, $T^3$ is $(PEG)_n$, $V^3$ is $-P(O)OH-$, $T^4$ is $(AA)_p$ and $V^4$ is absent.

In certain embodiments, $T^1$ is $(C_1\text{-}C_{12})$alkyl, $V^1$ is $-CO-$, $T^2$ is $(EDA)_w$, $V^2$ is absent, $T^3$ is $(AA)_p$, $V^3$ is absent, $T^4$ is absent and $V^4$ is absent.

In certain embodiments, $T^1$ is $(C_1\text{-}C_{12})$alkyl, $V^1$ is $-CO-$, $T^2$ is $(EDA)_w$, $V^2$ is $-CO-$, $T^3$ is $(CR^{13}OH)_h$, $V^3$ is $-CONR^{15}-$, $T^4$ is $(C_1\text{-}C_{12})$alkyl and $V^4$ is $-CO(AA)_p-$.

In certain embodiments, $T^1$ is $(C_1\text{-}C_{12})$alkyl, $V^1$ is $-CONR^{15}-$, $T^2$ is $(C_1\text{-}C_{12})$alkyl, $V^2$ is $-NR^{15}-$, $T^3$ is absent, $V^3$ is $-CO-$, $T^4$ is absent and $V^4$ is absent.

In certain embodiments, $T^1$ is $(C_1\text{-}C_{12})$alkyl, $V^1$ is $-CONR^{15}-$, $T^2$ is $(C_1\text{-}C_{12})$alkyl, $V^2$ is $-NR^{15}-$, $T^3$ is absent, $V^3$ is $-CO-$, $T^4$ is $(C_1\text{-}C_{12})$alkyl and $V^4$ is $-NR^{15}-$.

In certain embodiments, $T^1$ is $(C_1\text{-}C_{12})$alkyl, $V^1$ is $-CO-$, $T^2$ is $(EDA)_w$, $V^2$ is $-CO-$, $T^3$ is $(CR^{13}OH)_h$, $V^3$ is $-CONR^{15}-$, $T^4$ is $(PEG)_n$ and $V^4$ is $-CO(AA)_p-$.

In certain embodiments, $T^1$ is $(C_1\text{-}C_{12})$alkyl, $V^1$ is $-CO-$, $T^2$ is 4AP, $V^2$ is $-CO-$, $T^3$ is $(C_1\text{-}C_{12})$alkyl, $V^3$ is $-CO-$, $T^4$ is $(AA)_p$ and $V^4$ is absent.

In certain embodiments, $T^1$ is $(C_1\text{-}C_{12})$alkyl, $V^1$ is $-CO-$, $T^2$ is 4AP, $V^2$ is $-CO-$, $T^3$ is $(C_1\text{-}C_{12})$alkyl, $V^3$ is $-CO-$, $T^4$ is absent and $V^4$ is absent.

In certain embodiments, the linker is described by one of the following structures:

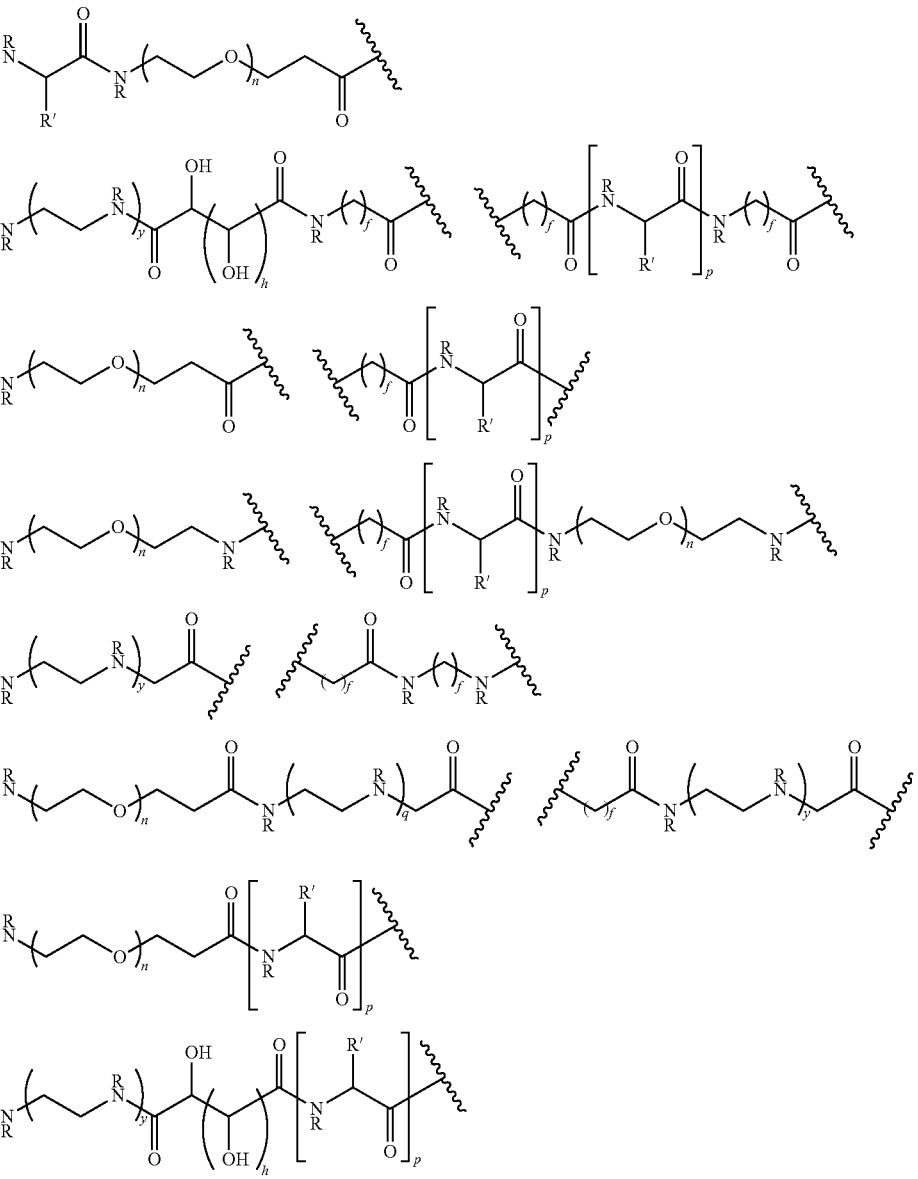

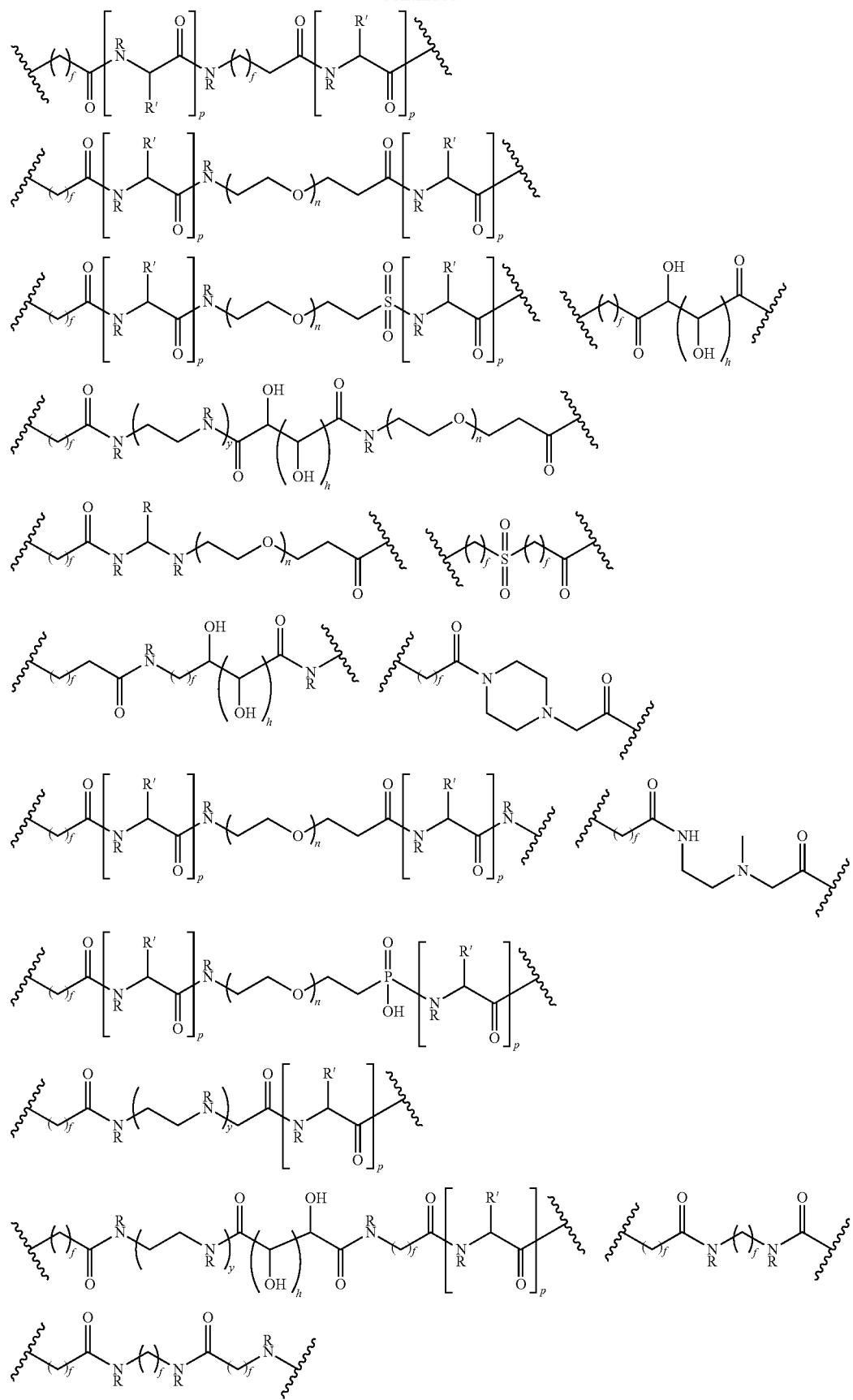

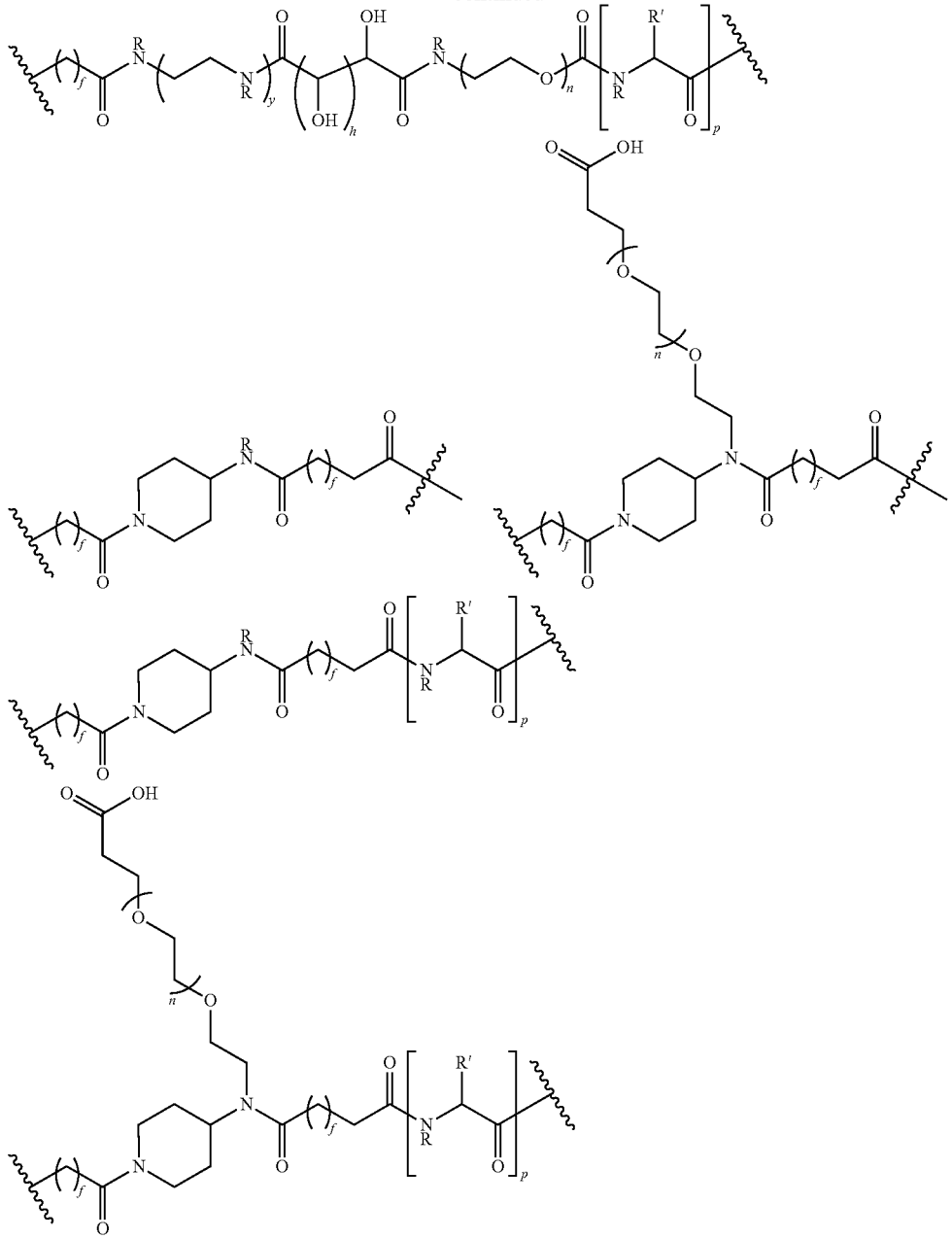

In certain embodiments of the linker structures depicted above, each f is independently 0 or an integer from 1 to 12; each y is independently 0 or an integer from 1 to 20; each n is independently 0 or an integer from 1 to 30; each p is independently 0 or an integer from 1 to 20; each h is independently 0 or an integer from 1 to 12; each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of the linker structures depicted above, each f is independently 0, 1, 2, 3, 4, 5 or 6; each y is independently 0, 1, 2, 3, 4, 5 or 6; each n is independently 0, 1, 2, 3, 4, 5 or 6; each p is independently 0, 1, 2, 3, 4, 5 or 6; and each h is independently 0, 1, 2, 3, 4, 5 or 6. In certain embodiments of the linker structures depicted above, each R is independently H, methyl or —(CH$_2$)$_m$—OH where m is 1, 2, 3 or 4 (e.g., 2).

In certain embodiments of the linker, L, $T^1$ is $(C_1\text{-}C_{12})$ alkyl, $V^1$ is —CO—, $T^2$ is 4AP, $V^2$ is —CO—, $T^3$ is $(C_1\text{-}C_{12})$alkyl, $V^3$ is —CO—, $T^4$ is absent and $V^4$ is absent. In certain embodiments, $T^1$ is ethylene, $V^1$ is —CO—, $T^2$ is 4AP, $V^2$ is —CO—, $T^3$ is ethylene, $V^3$ is —CO—, $T^4$ is absent and $V^4$ is absent. In certain embodiments, $T^1$ is ethylene, $V^1$ is —CO—, $T^2$ is 4AP, $V^2$ is —CO—, $T^3$ is ethylene, $V^3$ is —CO—, $T^4$ is absent and $V^4$ is absent, where $T^2$ (e.g., 4AP) has the following structure:

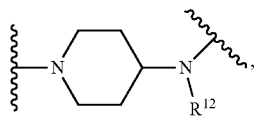

wherein
$R^{12}$ is a polyethylene glycol moiety (e.g., a polyethylene glycol or a modified polyethylene glycol).

In certain embodiments, the linker, L, includes the following structure:

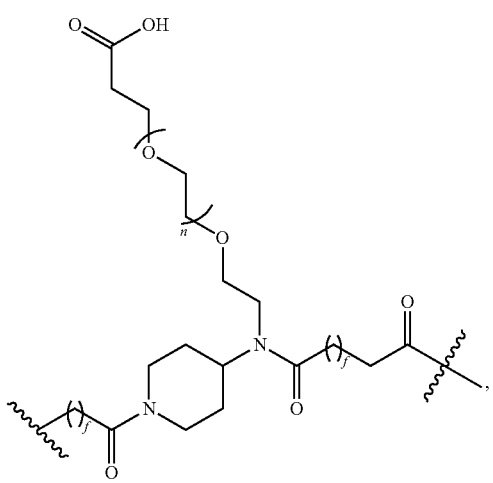

wherein
each f is independently an integer from 1 to 12; and
n is an integer from 1 to 30.

In certain embodiments, f is 1. In certain embodiments, f is 2. In certain embodiments, one f is 2 and one f is 1.

In certain embodiments, n is 1.

In certain embodiments, the left-hand side of the above linker structure is attached to the hydrazinyl-indolyl or the hydrazinyl-pyrrolo-pyridinyl coupling moiety, and the right-hand side of the above linker structure is attached to a maytansine.

Any of the chemical entities, linkers and coupling moieties set forth in the structures above may be adapted for use in the subject compounds and conjugates.

Additional disclosure related to hydrazinyl-indolyl and hydrazinyl-pyrrolo-pyridinyl compounds and methods for producing a conjugate is found in U.S. Application Publication No. 2014/0141025, filed Mar. 11, 2013, and U.S. Application Publication No. 2015/0157736, filed Nov. 26, 2014, the disclosures of each of which are incorporated herein by reference.

Anti-CD25 Antibodies

As noted above, a subject conjugate can comprise, as substituent $W^2$ an anti-CD25 antibody, where the anti-CD25 antibody has been modified to include a 2-formylglycine (FGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In some cases, a suitable anti-CD25 antibody specifically binds a CD25 polypeptide, where the epitope comprises amino acid residues within a CD25 antigen. In some embodiments, the anti-CD25 antibody binds an epitope within amino acids 101-137, an epitope within amino acids 106-132, an epitope within amino acids 111-127, an epitope comprising amino acids 116-122, or an epitope consisting of amino acids 116-122, of a CD25 amino acid sequence depicted in Table 3 below.

TABLE 3

| Human CD25 Amino Acid Sequence | |
|---|---|
| Human CD25 Amino Acid Sequence (SEQ ID NO: 1) | ELCDDDPPEIPHATFKAMAYKEGTMLNCECKRG FRRIKSGSLYMLCTGNSSHSSWDNQCQCTSSAT RNTTKQVTPQPEEQKERKTTEMQSPMQPVDQAS LPGHCREPPPWENEATERIYHFVVGQMVYYQCV QGYRALHRGPAESVCKMTHGKTRWTQPQLICTG EMETSQFPGEEKPQASPEGRPESETSCLVTTTD FQIQTEMAATMETSIFTTEYQVAVAGCVFLLIS VLLLSGLTWQRRQRKSRRTI |

The CD25 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 200 amino acids to about 251 amino acids of the human CD25 amino acid sequence depicted in Table 3.

A "CD25 antigen" or "CD25 polypeptide" can comprises an amino acid sequence having at least about 75%, at least about 80%, at least about 90%, at least about 95%, at least about 98%, at least about 99%, or 100%, amino acid sequence identity to a contiguous stretch of from about 200 amino acids to about 251 amino acids of the human CD25 amino acid sequence depicted in Table 3.

In some cases, a suitable anti-CD25 antibody exhibits high affinity binding to CD25. For example, in some cases, a suitable anti-CD25 antibody binds to CD25 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. In some cases, a suitable anti-CD25 antibody binds to an epitope present on CD25 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

In some cases, a suitable anti-CD25 antibody competes for binding to an epitope within CD25 with a second anti-CD25 antibody (e.g., basiliximab or daclizumab) and/or binds to the same epitope within CD25, as a second anti-CD25 antibody (e.g., basiliximab or daclizumab). In some cases, an anti-CD25 antibody that competes for binding to an epitope within CD25 with a second anti-CD25 antibody also binds to the same epitope as the second anti-CD25 antibody (e.g., basiliximab or daclizumab). In some cases, an anti-CD25 antibody that competes for binding to an epitope within CD25 with a second anti-CD25 antibody binds to an epitope that is overlapping with the epitope bound by the second anti-CD25 antibody (e.g., basiliximab or daclizumab). In some cases, the anti-CD25 antibody is humanized.

In some embodiments, the anti-CD25 antibody is an IgG1 antibody. For example, in certain aspects, the anti-CD25 antibody is an IgG1 kappa antibody.

In certain aspects, the anti-CD25 antibody competes with interleukin-2 (IL-2) for binding to CD25.

In some embodiments, the anti-CD25 antibody comprises one, two, three, four, five, or all six complementarity determining regions (CDRs) of the anti-CD25 antibody basiliximab. In certain aspects, the anti-CD25 antibody comprises one, two, three, four, five, or all six complementarity determining regions (CDRs) of the anti-CD25 antibody daclizumab.

In certain aspects, the anti-CD25 antibody is a FGly'-containing antibody based on basiliximab or daclizumab. For example, in some embodiments, the antibody is a derivative of daclizumab, where the difference between daclizumab and the derivative is the presence of one or more FGly' residues (and optionally, the associated FGE recognition sequence amino acids) in the derivative. Provided in Table 4 are nucleic acid and amino acid sequences for an example daclizumab-based antibody according to one embodiment. In the amino acid sequences in Table 4, variable regions are underlined and CDRs are shown in bold. In this example daclizumab-based antibody, the italicized residues at the C-terminus of the heavy chain replace a lysine residue at the C-terminus of a standard IgG1 heavy chain. The underlined residues (LCTPSR) (SEQ ID NO: 16) among the italicized residues constitute the aldehyde tag, where the C is converted to an FGly residue by FGE upon expression of the heavy chain. The non-underlined residues among the italicized residues are additional residues that are different from a standard IgG1 heavy chain sequence.

TABLE 4

| Example daclizumab-based antibody | |
|---|---|
| Light chain amino acid sequence (SEQ ID NO: 2) | DIQMTQSPSTLSASVGDRVTITCSASSSISYMHWYQQKPGKAP KLLIYTTSNLASGVPARFSGSGSGTEFTLTISSLQPDDFATYYC HQRSTYPLTFGQGTKVEVKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC |
| Heavy chain amino acid sequence (SEQ ID NO: 3) | QVQLVQSGAEVKKPGSSVKVSCKASGYTFTSYRMHWVRQAP GQGLEWIGYINPSTGYTEYNQKFKDKATITADESTNTAYMEL SSLRSEDTAVYYCARGGGVFDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCS VMHEALHNHYTQKSLSLSPG*SLCTPSRGS* |
| Light chain-encoding DNA sequence (SEQ ID NO: 4) | GACATCCAGATGACCCAGTCTCCTTCCACCCTGTCTGCATCT GTAGGAGACAGAGTCACCATCACTTGCAGCGCCAGCAGCA GTATTAGTTACATGCACTGGTATCAGCAGAAACCAGGGAAA GCCCCTAAGCTCCTGATCTATACCACCTCCAACTTGGCCAGT GGGGTCCCAGCCAGGTTCAGCGGCAGTGGATCTGGGACAG AATTCACTCTCACCATCAGCAGCCTGCAGCCTGATGATTTTG CAACTTATTACTGCCACCAGAGGAGCACCTATCCCCTGACT TTCGGCCAGGGGACCAAGGTGGAGGTGAAACGTACTGTGG CTGCACCATCTGTCTTCATCTTCCCGCCATCTGATGAGCAGT TGAAATCTGGAACTGCCTCTGTTGTGTGCCTGCTGAATAACT TCTATCCCAGAGAGGCCAAAGTACAGTGGAAGGTGGATAA CGCCCTCCAATCGGGTAACTCCCAGGAGAGTGTCACAGAGC AGGACAGCAAGGACAGCACCTACAGCCTCAGCAGCACCCT GACGCTGAGCAAAGCAGACTACGAGAAACACAAAGTCTAC GCCTGCGAAGTCACCCATCAGGGCCTGAGCTCGCCCGTCAC AAAGAGCTTCAACAGGGGAGAGTGTTAGTGA |
| Heavy chain-encoding DNA sequence (SEQ ID NO: 5) | CAGGTGCAGCTGGTGCAGTCTGGGGCTGAGGTGAAGAAGC CTGGGAGCTCAGTGAAGGTTTCCTGCAAGGCATCTGGATAC ACCTTCACCAGCTACAGGATGCACTGGGTGCGACAGGCCCC TGGACAAGGGCTTGAGTGGATCGGATACATCAACCCTAGTA CCGGTTACAGAGTACAACCAGAAGTTCAAGGACAAGGC CACCATCACCGCCGACGAGTCCACGAACACAGCCTACATGG AGCTGAGCAGCCTGAGATCTGAGGACACGGCCGTGTATTAC TGTGCGAGAGGCGGAGGAGTGTTCGACTACTGGGGCCAGG GAACCCTGGTGACCGTCTCCTCAGCTAGCACCAAGGGCCCA TCGGTCTTCCCCCTGGCACCCTCCTCCAAGAGCACCTCTGGG GGCACAGCGGCCCTGGGCTGCCTGGTCAAGGACTACTTCCC CGAACCGGTGACGGTGTCGTGGAACTCAGGCGCCCTGACCA GCGGCGTGCACACCTTCCCGGCTGTCCTACAGTCCTCAGGA CTCTACTCCCTCAGCAGCGTGGTGACCGTGCCCTCCAGCAG CTTGGGCACCCAGACCTACATCTGCAACGTGAATCACAAGC CCAGCAACACCAAGGTGGACAAGAGAGTTGAGCCCAAATC TTGTGACAAAACTCACACATGCCCACCGTGCCCAGCACCTG |

TABLE 4-continued

Example daclizumab-based antibody

```
AACTCCTGGGGGACCGTCAGTCTTCCTCTTCCCCCCAAAA
CCCAAGGACACCCTCATGATCTCCCGGACCCCTGAGGTCAC
ATGCGTGGTGGTGGACGTGAGCCACGAAGACCCTGAGGTCA
AGTTCAACTGGTACGTGGACGGCGTGGAGGTGCATAATGCC
AAGACAAAGCCAAGAGAGGAGCAGTACAACAGCACGTACC
GTGTGGTCAGCGTCCTCACCGTCCTGCACCAGGACTGGCTG
AATGGCAAGGAGTACAAGTGCAAGGTCTCCAACAAAGCCC
TCCCAGCCCCCATCGAGAAAACCATCTCCAAAGCCAAAGGG
CAGCCCCGAGAACCACAGGTGTACACCCTGCCCCCATCCCG
GGAGGAGATGACCAAGAACCAGGTCAGCCTGACCTGCCTG
GTCAAAGGCTTCTATCCCAGCGACATCGCCGTGGAGTGGGA
GAGCAATGGGCAGCCGGAGAACAACTACAAGACCACGCCT
CCCGTGCTGGACTCCGACGGCTCCTTCTTCCTCTACAGCAAG
CTCACCGTGGACAAGAGCAGGTGGCAGCAGGGGAACGTCT
TCTCATGCTCCGTGATGCATGAGGCTCTGCACAACCACTAC
ACGCAGAAGAGCCTCTCCCTGTCTCCCGGGTCCTTATGTACC
CCTTCTAGAGGATCCTGATGA
```

In some embodiments, a suitable anti-CD25 antibody can induce apoptosis in a cell that expresses CD25 on its cell surface.

An anti-CD25 antibody suitable for use in a subject conjugate will in some cases inhibit the proliferation of human tumor cells that express on their surface (e.g., overexpress) CD25, where the inhibition occurs in vitro, in vivo, or both in vitro and in vivo. For example, in some cases, an anti-CD25 antibody suitable for use in a subject conjugate inhibits proliferation of human tumor cells that express on their surface (e.g., overexpress) CD25 by at least about 15%, at least about 20%, at least about 25%, at least about 30%, at least about 40%, at least about 50%, at least about 60%, at least about 70%, at least about 80%, or more than 80%, e.g., by at least about 85%, at least about 90%, at least about 95%, at least about 98%, at least about 99%, or 100%.

In some embodiments, the anti-CD25 antibody competes for binding to CD25 (e.g., an epitope of CD25 comprising amino acid residues within a CD25 antigen (e.g., an epitope within amino acids 101-137, an epitope within amino acids 106-132, an epitope within amino acids 111-127, an epitope comprising amino acids 116-122, or an epitope consisting of amino acids 116-122, of a CD25 amino acid sequence depicted in Table 3)) with an antibody comprising a heavy chain complementarity determining region (CDR) selected from SYRMH (daclizumab VH CDR1; SEQ ID NO:6), YINPSTGYTEYNQKFKD (daclizumab VH CDR2; SEQ ID NO:7), GGGVFDY (daclizumab VH CDR3; SEQ ID NO:8), and any combination thereof. In some cases, the anti-CD25 antibody is humanized.

In certain aspects, the anti-CD25 antibody competes for binding to CD25 (e.g., an epitope of CD25 comprising amino acid residues within a CD25 antigen (e.g., an epitope within amino acids 101-137, an epitope within amino acids 106-132, an epitope within amino acids 111-127, an epitope comprising amino acids 116-122, or an epitope consisting of amino acids 116-122, of a CD25 amino acid sequence depicted in Table 3)) with an antibody comprising a light-chain CDR selected from SASSSISYMH (daclizumab VL CDR1; SEQ ID NO:9), YTSILHS (daclizumab VL CDR2; SEQ ID NO:10), and QQGNTLPWT (daclizumab VL CDR3; SEQ ID NO:11), and any combination thereof. In some cases, the anti-CD25 antibody is humanized.

In some embodiments, the anti-CD25 antibody competes for binding to CD25 (e.g., an epitope of CD25 comprising amino acid residues within a CD25 antigen (e.g., an epitope within amino acids 101-137, an epitope within amino acids 106-132, an epitope within amino acids 111-127, an epitope comprising amino acids 116-122, or an epitope consisting of amino acids 116-122, of a CD25 amino acid sequence depicted in Table 3)) with an antibody comprising the following six CDRs: SYRMH (daclizumab VH CDR1; SEQ ID NO:6), YINPSTGYTEYNQKFKD (daclizumab VH CDR2; SEQ ID NO:7), GGGVFDY (daclizumab VH CDR3; SEQ ID NO:8), SASSSISYMH (daclizumab VL CDR1; SEQ ID NO:9), YTSILHS (daclizumab VL CDR2; SEQ ID NO:10), and QQGNTLPWT (daclizumab VL CDR3; SEQ ID NO:11). In some cases, the anti-CD25 antibody is humanized.

In some embodiments, the anti-CD25 antibody comprises the following six CDRs: SYRMH (daclizumab VH CDR1; SEQ ID NO:6), YINPSTGYTEYNQKFKD (daclizumab VH CDR2; SEQ ID NO:7), GGGVFDY (daclizumab VH CDR3; SEQ ID NO:8//), SASSSISYMH (daclizumab VL CDR1; SEQ ID NO:9), YTSILHS (daclizumab VL CDR2; SEQ ID NO:10), and QQGNTLPWT (daclizumab VL CDR3; SEQ ID NO:11). In some cases, the anti-CD25 antibody is humanized.

In certain aspects, the anti-CD25 antibody comprises VH CDRs present in an anti-CD25 VH region comprising the following amino acid sequence:

(daclizumab VH, SEQ ID NO: 12)
QVQLVQSGAEVKKPGSSVKVSCKASGYTFTSYRMHWVRQAPGQGLEWIGYI

NPSTGYTEYNQKFKDKATITADESTNTAYMELSSLRSEDTAVYYCARGGGV

FDYWGQGTLVTVSS.

In some embodiments, the anti-CD25 antibody comprises VL CDRs present in an anti-CD25 VL region comprising the following amino acid sequence:

(daclizumab VL, SEQ ID NO: 13/
DIQMTQSPSTLSASVGDRVTITCSASSSISYMHWYQQKPGKAPKLLIYTTS

NLASGVPARFSGSGSGTEFTLTISSLQPDDFATYYCHQRSTYPLTFGQGTK

VEVK.

In certain aspects, the anti-CD25 antibody comprises VH CDRs present in (daclizumab VH, SEQ ID NO: 12)
QVQLVQSGAEVKKPGSSVKVSCKASGYTFTSYRMHWVRQAPGQGLEWIGYI

NPSTGYTEYNQKFKDKATITADESTNTAYMELSSLRSEDTAVYYCARGGGV

FDYWGQGTLVTVSS and VL CDRs present in DIQMTQSPSTL-SASVGDRVTITCSASSSI-SYMHWYQQKPGKAPKLLIYTTSNLASGVPAR FSGSGSGTEFTLTISSLQPDDFATYYCHQRSTY-PLTFGQGTKVEVK (daclizumab VL, SEQ ID NO:13).

Modified Constant Region Sequences

As noted above, the amino acid sequence of an anti-CD25 antibody is modified to include a sulfatase motif that contains a serine or cysteine residue that is capable of being converted (oxidized) to a 2-formylglycine (FGly) residue by action of a formylglycine generating enzyme (FGE) either in vivo (e.g., at the time of translation of an aldehyde tag-containing protein in a cell) or in vitro (e.g., by contacting an aldehyde tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., anti-CD25 antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target anti-CD25 polypeptide is minimized, so as to minimize the number of amino acid residues that are inserted, deleted, substituted (replaced), or added (e.g., to the N- or C-terminus). Minimizing the extent of amino acid sequence modification of the target anti-CD25 polypeptide may minimize the impact such modifications may have upon anti-CD25 function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a $CH_2$ domain of an Ig heavy chain. An aldehyde tag can be present within a $CH_3$ domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \qquad (I')$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an anti-CD25 heavy and/or light chain can be modified to provide a sequence of at least 5 amino acids of the formula $X^1Z^{10}X^2Z^{20}X^3Z^{30}$, where $Z^{10}$ is cysteine or serine;

$Z^{20}$ is a proline or alanine residue;

$Z^{30}$ is an aliphatic amino acid or a basic amino acid;

$X^1$ is present or absent and, when present, is any amino acid, with the proviso that when the heterologous sulfatase motif is at an N-terminus of the polypeptide, $X^1$ is present;

$X^2$ and $X^3$ are each independently any amino acid, where the sequence is within or adjacent a solvent-accessible loop region of the Ig constant region, and wherein the sequence is not at the C-terminus of the Ig heavy chain.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

$$X^1CX^2PX^3Z^{30} \tag{I''}$$

where
- $X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, $X^1$ is present;
- $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and
- $Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO:16), MCTPSR (SEQ ID NO:17), VCTPSR (SEQ ID NO:18), LCSPSR (SEQ ID NO:19), LCAPSR (SEQ ID NO:20), LCVPSR (SEQ ID NO:21), LCGPSR (SEQ ID NO:22), ICTPAR (SEQ ID NO:23), LCTPSK (SEQ ID NO:24), MCTPSK (SEQ ID NO:25), VCTPSK (SEQ ID NO:26), LCSPSK (SEQ ID NO:27), LCAPSK (SEQ ID NO:28), LCVPSK (SEQ ID NO:29), LCGPSK (SEQ ID NO:30), LCTPSA (SEQ ID NO:31), ICTPAA (SEQ ID NO:32), MCTPSA (SEQ ID NO:33), VCTPSA (SEQ ID NO:34), LCSPSA (SEQ ID NO:35), LCAPSA (SEQ ID NO:36), LCVPSA (SEQ ID NO:37), and LCGPSA (SEQ ID NO:38).

FGly-Containing Sequences

Upon action of FGE on the modified anti-CD25 heavy and/or light chain, the serine or the cysteine in the sulfatase motif is modified to FGly. Thus, the FGly-containing sulfatase motif can be of the formula:

$$X^1(FGly)X^2Z^{20}X^3Z^{30} \tag{I'''}$$

where
FGly is the formylglycine residue;
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, the modified polypeptide containing the FGly residue may be conjugated to a drug (e.g., a maytansinoid) by reaction of the FGly with the drug (e.g., a drug containing a hydrazinyl-indolyl or a hydrazinyl-pyrrolo-pyridinyl coupling moiety, as described above) to produce an FGly'-containing sulfatase motif. As used herein, the term FGly' refers to the modified amino acid residue of the sulfatase motif that is coupled to the drug, such as a maytansinoid (e.g., the modified amino acid residue of formula (I)). Thus, the FGly'-containing sulfatase motif can be of the formula:

$$X^1(FGly')X^2Z^{20}X^3Z^{30} \tag{II}$$

where
FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

In certain embodiments, the modified amino acid residue of formula (I) is positioned at a C-terminus of a heavy chain constant region of the anti-CD25 antibody. In some instances, the heavy chain constant region comprises a sequence of the formula (II):

$$X^1(FGly')X^2Z^{20}X^3Z^{30} \tag{II}$$

wherein
FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, XV is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence QKSLSLSPGK (SEQ ID NO: 158), and where the sequence may include 1, 2, 3, 4, 5, or from 5 to 10, amino acids not present in a native, wild-type heavy Ig chain constant region.

In certain embodiments, the heavy chain constant region comprises the sequence SLSLSPGSL(FGly')TPSRGS (SEQ ID NO: 39) at the C-terminus of the Ig heavy chain, e.g., in place of a native SLSLSPGK (SEQ ID NO:40) sequence.

In certain embodiments, the modified amino acid residue of formula (I) is positioned in a light chain constant region of the anti-CD25 antibody. In certain embodiments, the light chain constant region comprises a sequence of the formula (II):

wherein

FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence KVDNAL (SEQ ID NO:42) and/or is N-terminal to the amino acid sequence QSGNSQ (SEQ ID NO:43).

In certain embodiments, the light chain constant region comprises the sequence KVDNAL(FGly')TPSRQSGNSQ (SEQ ID NO:44).

In certain embodiments, the modified amino acid residue of formula (I) is positioned in a heavy chain CH1 region of the anti-CD25 antibody. In certain embodiments, the heavy chain CH1 region comprises a sequence of the formula (II):

wherein

FGly' is the modified amino acid residue of formula (I);
$Z^{20}$ is either a proline or alanine residue (which can also be represented by (P/A));
$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;
$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present;
$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G; and wherein the sequence is C-terminal to the amino acid sequence SWNSGA (SEQ ID NO:46) and/or is N-terminal to the amino acid sequence GVHTFP (SEQ ID NO:47).

In certain embodiments, the heavy chain CH1 region comprises the sequence SWNSGAL(FGly')TPSRGVHTFP (SEQ ID NO:48).

Site of Modification

As noted above, the amino acid sequence of an anti-CD25 antibody is modified to include a sulfatase motif that contains a serine or cysteine residue that is capable of being converted (oxidized) to an FGly residue by action of an FGE either in vivo (e.g., at the time of translation of an aldehyde tag-containing protein in a cell) or in vitro (e.g., by contacting an aldehyde tag-containing protein with an FGE in a cell-free system). The anti-CD25 polypeptides used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target anti-CD25 antibodies" or "target anti-CD25 Ig polypeptides."

The site in an anti-CD25 antibody into which a sulfatase motif is introduced can be any convenient site. As noted above, in some instances, the extent of modification of the native amino acid sequence of the target anti-CD25 polypeptide is minimized, so as to minimize the number of amino acid residues that are inserted, deleted, substituted (replaced), and/or added (e.g., to the N- or C-terminus). Minimizing the extent of amino acid sequence modification of the target anti-CD25 polypeptide may minimize the impact such modifications may have upon anti-CD25 function and/or structure.

An anti-CD25 antibody heavy chain constant region can include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region. An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged anti-CD25 antibody comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FGly-modified Ig polypeptide. Allotypic variants of Ig heavy chains are known in the art. See, e.g., Jefferis and Lefranc (2009) MAbs 1:4.

In some cases, an aldehyde-tagged anti-CD25 antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FGly-modified anti-CD25 antibody polypeptide. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged anti-CD25 polypeptide can comprise a heavy chain constant region modified to include a sulfatase motif as described above, where the sulfatase motif is in or adjacent a surface-accessible loop region of the anti-CD25 polypeptide heavy chain constant region.

In some instances, a target anti-CD25 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21) amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG. 12B.

In some instances, a target anti-CD25 immunoglobulin is modified to include a sulfatase motif as described above, where the modification includes one or more amino acid residue insertions, deletions, and/or substitutions. In certain embodiments, the sulfatase motif is within, or adjacent to, a region of an IgG1 heavy chain constant region corresponding to one or more of: 1) amino acids 1-6; 2) amino acids 16-22; 3) amino acids 34-47; 4) amino acids 42-49; 5) amino acids 42-62; 6) amino acids 34-37; 7) amino acids 69-71; 8) amino acids 79-81; 9) amino acids 78-81; 10) amino acids 87-91; 11) amino acids 100-121; 12) amino acids 127-131; 13) amino acids 137-141; 14) amino acid 149-157; 15) amino acids 151-157; 16) amino acids 164-165; 17) amino acids 164-172; 18) amino acids 169-171; 19) amino acids 179-183; 20) amino acids 189-193; 21) amino acids 200-202; 22) amino acids 209-215; 23) amino acids 221-229; 24) amino acids 22-228; 25) amino acids 236-245; 26) amino acids 217-261; 27) amino acids 268-274; 28) amino acids 278-287; 29) amino acids 313-331; and 30) amino acids 324-331; wherein the amino acid numbering is based on the amino acid numbering of human IgG1 as set out in SEQ ID NO:164// (human IgG1 constant region; sequence depicted in FIG. 12B).

Exemplary surface-accessible loop regions of an IgG1 heavy chain include: 1) ASTKGP (SEQ ID NO:49); 2) KSTSGGT (SEQ ID NO:50); 3) PEPV (SEQ ID NO:51); 4) NSGALTSG (SEQ ID NO:52); 5) NSGALT-SGVHTFPAVLQSSGL (SEQ ID NO:53); 6) QSSGL (SEQ ID NO:54); 7) VTV; 8) QTY; 9) TQTY (SEQ ID NO:55); 10) HKPSN (SEQ ID NO:56); 11) EPKSCDKTH-TCPPCPAPELLGG (SEQ ID NO:57); 12) FPPKP (SEQ ID NO:58); 13) ISRTP (SEQ ID NO:59); 14) DVSHEDPEV (SEQ ID NO:60); 15) SHEDPEV (SEQ ID NO:61); 16) DG; 17) DGVEVHNAK (SEQ ID NO:62); 18) HNA; 19) QYNST (SEQ ID NO:63); 20) VLTVL (SEQ ID NO:64); 21) GKE; 22) NKALPAP (SEQ ID NO:65); 23) SKAKGQPRE (SEQ ID NO:66); 24) KAKGQPR (SEQ ID NO:67); 25) PPSRKELTKN (SEQ ID NO:68); 26) YPSDI (SEQ ID NO:69); 27) NGQPENN (SEQ ID NO:70); 28) TPPVLDSDGS (SEQ ID NO:71); 29) HEALHN-HYTQKSLSLSPGK (SEQ ID NO:72); and 30) SLSPGK (SEQ ID NO:73), as shown in FIGS. 12A and 12B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG2 heavy chain constant region corresponding to one or more of: 1) amino acids 1-6; 2) amino acids 13-24; 3) amino acids 33-37; 4) amino acids 43-54; 5) amino acids 58-63; 6) amino acids 69-71; 7) amino acids 78-80; 8) 87-89; 9) amino acids 95-96; 10) 114-118; 11) 122-126; 12) 134-136; 13) 144-152; 14) 159-167; 15) 175-176; 16) 184-188; 17) 195-197; 18) 204-210; 19) 216-224; 20) 231-233; 21) 237-241; 22) 252-256; 23) 263-269; 24) 273-282; 25) amino acids 299-302; where the amino acid numbering is based on the numbering of the amino acid sequence set forth in SEQ ID NO: 165// (human IgG2; also depicted in FIG. 12B).

Exemplary surface-accessible loop regions of an IgG2 heavy chain include 1) ASTKGP (SEQ ID NO:49); 2) PCSRSTSESTAA (SEQ ID NO:74); 3) FPEPV (SEQ ID NO:75); 4) SGALTSGVHTFP (SEQ ID NO:76); 5) QSSGLY (SEQ ID NO:77); 6) VTV; 7) TQT; 8) HKP; 9) DK; 10) VAGPS (SEQ ID NO:78); 11) FPPKP (SEQ ID NO:58); 12) RTP; 13) DVSHEDPEV (SEQ ID NO:60); 14) DGVEVHNAK (SEQ ID NO:62); 15) FN; 16) VLTVV (SEQ ID NO:79); 17) GKE; 18) NKGLPAP (SEQ ID NO:80); 19) SKTKGQPRE (SEQ ID NO:81); 20) PPS; 21) MTKNQ (SEQ ID NO:82); 22) YPSDI (SEQ ID NO:69); 23) NGQPENN (SEQ ID NO:70); 24) TPPMLDSDGS (SEQ ID NO:84); 25) GNVF (SEQ ID NO:85); and 26) HEALHNHYTQKSLSLSPGK (SEQ ID NO:72), as shown in FIG. 12B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG3 heavy chain constant region corresponding to one or more of: 1) amino acids 1-6; 2) amino acids 13-22; 3) amino acids 33-37; 4) amino acids 43-61; 5) amino acid 71; 6) amino acids 78-80; 7) 87-91; 8) amino acids 97-106;

9) 111-115; 10) 147-167; 11) 173-177; 16) 185-187; 13) 195-203; 14) 210-218; 15) 226-227; 16) 238-239; 17) 246-248; 18) 255-261; 19) 267-275; 20) 282-291; 21) amino acids 303-307; 22) amino acids 313-320; 23) amino acids 324-333; 24) amino acids 350-352; 25) amino acids 359-365; and 26) amino acids 372-377; where the amino acid numbering is based on the numbering of the amino acid sequence set forth in SEQ ID NO: 166// (human IgG3; also depicted in FIG. 12B).

Exemplary surface-accessible loop regions of an IgG3 heavy chain include 1) ASTKGP (SEQ ID NO:49); 2) PCSRSTSGGT (SEQ ID NO:87); 3) FPEPV (SEQ ID NO:75); 4) SGALTSGVHTFPAVLQSSG (SEQ ID NO:88); 5) V; 6) TQT; 7) HKPSN (SEQ ID NO:56); 8) RVELKTPLGD (SEQ ID NO:89); 9) CPRCPKP (SEQ ID NO:90); 10) PKSCDTPPPCPRCPAPELLGG (SEQ ID NO:91); 11) FPPKP (SEQ ID NO:58); 12) RTP; 13) DVSHEDPEV (SEQ ID NO:60); 14) DGVEVHNAK (SEQ ID NO:62); 15) YN; 16) VL; 17) GKE; 18) NKALPAP (SEQ ID NO:65); 19) SKTKGQPRE (SEQ ID NO:81); 20) PPSREEMTKN (SEQ ID NO:92); 21) YPSDI (SEQ ID NO:69); 22) SSGQPENN (SEQ ID NO:93); 23) TPPMLDSDGS (SEQ ID NO:84); 24) GNI; 25) HEALHNR (SEQ ID NO:95); and 26) SLSPGK (SEQ ID NO:40), as shown in FIG. 12B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgG4 heavy chain constant region corresponding to one or more of: 1) amino acids 1-5; 2) amino acids 12-23; 3) amino acids 32-36; 4) amino acids 42-53; 5) amino acids 57-62; 6) amino acids 68-70; 7) amino acids 77-79; 8) amino acids 86-88; 9) amino acids 94-95; 10) amino acids 101-102; 11) amino acids 108-118; 12) amino acids 122-126; 13) amino acids 134-136; 14) amino acids 144-152; 15) amino acids 159-167; 16) amino acids 175-176; 17) amino acids 185-186; 18) amino acids 196-198; 19) amino acids 205-211; 20) amino acids 217-226; 21) amino acids 232-241; 22) amino acids 253-257; 23) amino acids 264-265; 24) 269-270; 25) amino acids 274-283; 26) amino acids 300-303; 27) amino acids 399-417; where the amino acid numbering is based on the numbering of the amino acid sequence set forth in SEQ ID NO: 167// (human IgG4; also depicted in FIG. 12B).

Exemplary surface-accessible loop regions of an IgG4 heavy chain include 1) STKGP (SEQ ID NO:96); 2) PCSRSTSESTAA (SEQ ID NO:74); 3) FPEPV (SEQ ID NO:75); 4) SGALTSGVHTFP (SEQ ID NO:76); 5) QSSGLY (SEQ ID NO:77); 6) VTV; 7) TKT; 8) HKP; 9) DK; 10) YG; 11) CPAPEFLGGPS (SEQ ID NO:97); 12) FPPKP (SEQ ID NO:58); 13) RTP; 14) DVSQEDPEV (SEQ ID NO:98); 15) DGVEVHNAK (SEQ ID NO:62); 16) FN; 17) VL; 18) GKE; 19) NKGLPSS (SEQ ID NO:99); 20) SKAKGQPREP (SEQ ID NO:100); 21) PPSQEEMTKN (SEQ ID NO:101); 22) YPSDI (SEQ ID NO:69); 23) NG; 24) NN; 25) TPPVLDSDGS (SEQ ID NO:71); 26) GNVF (SEQ ID NO:85); and 27) HEALHNHYTQKSLSLSLGK (SEQ ID NO:102), as shown in FIG. 12B.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an IgA heavy chain constant region corresponding to one or more of: 1) amino acids 1-13; 2) amino acids 17-21; 3) amino acids 28-32; 4) amino acids 44-54; 5) amino acids 60-66; 6) amino acids 73-76; 7) amino acids 80-82; 8) amino acids 90-91; 9) amino acids 123-125; 10) amino acids 130-133; 11) amino acids 138-142; 12) amino acids 151-158; 13) amino acids 165-174; 14) amino acids 181-184; 15) amino acids 192-195; 16) amino acid 199; 17) amino acids 209-210; 18) amino acids 222-245; 19) amino acids 252-256; 20) amino acids 266-276; 21) amino acids 293-294; 22) amino acids 301-304; 23) amino acids 317-320; 24) amino acids 329-353; where the amino acid numbering is based on the numbering of the amino acid sequence set forth in SEQ ID NO: 168 (human IgA; also depicted in FIG. 12B).

Exemplary surface-accessible loop regions of an IgA heavy chain include 1) ASPTSPKVFPLSL (SEQ ID NO:103); 2) QPDGN (SEQ ID NO:104); 3) VQGFFPQEPL (SEQ ID NO:105); 4) SGQGVTARNFP (SEQ ID NO:106); 5) SGDLYTT (SEQ ID NO:107); 6) PATQ (SEQ ID NO:108); 7) GKS; 8) YT; 9) CHP; 10) HRPA (SEQ ID NO:109); 11) LLGSE (SEQ ID NO:110); 12) GLRDASGV (SEQ ID NO:111); 13) SSGKSAVQGP (SEQ ID NO:112); 14) GCYS (SEQ ID NO:113); 15) CAEP (SEQ ID NO:114); 16) PE; 17) SGNTFRPEVHLLPPPSEELALNEL (SEQ ID NO:115); 18) ARGFS (SEQ ID NO:116); 19) QGSQEL-PREKY (SEQ ID NO:117); 20) AV; 21) AAED (SEQ ID NO:118); 22) HEAL (SEQ ID NO:119); and 23) IDR-LAGKPTHVNVSVVMAEVDGTCY (SEQ ID NO:120), as shown in FIG. 12B.

A sulfatase motif can be provided within or adjacent one or more of these amino acid sequences of such modification sites of an Ig heavy chain. For example, an Ig heavy chain polypeptide can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

The amino acid sequence of a surface-accessible loop region can thus be modified to provide a sulfatase motif, where the modifications can include insertions, deletions, and/or substitutions. For example, where the modification is in a CH1 domain, the surface-accessible loop region can have the amino acid sequence NSGALTSG (SEQ ID NO:52), and the aldehyde-tagged sequence can be, e.g., NSGALCTPSRG (SEQ ID NO:122), e.g., where the "TS" residues of the NSGALTSG (SEQ ID NO:52) sequence are replaced with "CTPSR," (SEQ ID NO:123) such that the sulfatase motif has the sequence LCTPSR (SEQ ID NO:16). As another example, where the modification is in a CH2 domain, the surface-accessible loop region can have the amino acid sequence NKALPAP (SEQ ID NO:65), and the aldehyde-tagged sequence can be, e.g., NLCTPSRAP (SEQ ID NO:125), e.g., where the "KAL" residues of the NKA-LPAP (SEQ ID NO:65) sequence are replaced with "LCTPSR," (SEQ ID NO:16) such that the sulfatase motif has the sequence LCTPSR (SEQ ID NO:16). As another example, where the modification is in a CH2/CH3 domain, the surface-accessible loop region can have the amino acid sequence KAKGQPR (SEQ ID NO:67), and the aldehyde-tagged sequence can be, e.g., KAKGLCTPSR (SEQ ID NO:126), e.g., where the "GQP" residues of the KAKGQPR (SEQ ID NO:100) sequence are replaced with "LCTPS," (SEQ ID NO:31) such that the sulfatase motif has the sequence LCTPSR (SEQ ID NO:16).

As noted above, an isolated aldehyde-tagged anti-CD25 Ig polypeptide can comprise a light chain constant region modified to include a sulfatase motif as described above, where the sulfatase motif is in or adjacent a surface-accessible loop region of the Ig polypeptide light chain constant region. Illustrative examples of surface-accessible loop regions of a light chain constant region are presented in FIGS. 12A and 12C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 130-135; 2) amino acids 141-143; 3) amino acid 150; 4) amino acids 162-166; 5) amino acids 163-166; 6) amino acids 173-180; 7) amino acids 186-194; 8) amino acids 211-212; 9) amino acids 220-225; 10) amino acids 233-236; wherein the amino acid numbering is based on the amino acid numbering of human kappa light chain as depicted in FIG. 12C. In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of an Ig light chain constant region corresponding to one or more of: 1) amino acids 1-6; 2) amino acids 12-14; 3) amino acid 21; 4) amino acids 33-37; 5) amino acids 34-37; 6) amino acids 44-51; 7) amino acids 57-65; 8) amino acids 83-83; 9) amino acids 91-96; 10) amino acids 104-107; where the amino acid numbering is based on SEQ ID NO:162 and 170 (human kappa light chain; amino acid sequence depicted in FIG. 12C).

Exemplary surface-accessible loop regions of an Ig light chain (e.g., a human kappa light chain) include: 1) RTVAAP (SEQ ID NO:127); 2) PPS; 3) Gly (see, e.g., Gly at position 150 of the human kappa light chain sequence depicted in FIG. 12C); 4) YPREA (SEQ ID NO:128); 5) PREA (SEQ ID NO:129); 6) DNALQSGN (SEQ ID NO:130); 7) TEQD-SKDST (SEQ ID NO:131); 8) HK; 9) HQGLSS (SEQ ID NO:132); and 10) RGEC (SEQ ID NO:133), as shown in FIGS. 12A and 12C.

Exemplary surface-accessible loop regions of an Ig lambda light chain include QPKAAP (SEQ ID NO:134), PPS, NK, DFYPGAV (SEQ ID NO:135), DSSPVKAG (SEQ ID NO:136), TTP, SN, HKS, EG, and APTECS (SEQ ID NO:137), as shown in FIG. 12C.

In some instances, a target immunoglobulin is modified to include a sulfatase motif as described above, where the modification includes one or more amino acid residue insertions, deletions, and/or substitutions. In certain embodiments, the sulfatase motif is within, or adjacent to, a region of a rat Ig light chain constant region corresponding to one or more of: 1) amino acids 1-6; 2) amino acids 12-14; 3) amino acids 121-22; 4) amino acids 31-37; 5) amino acids 44-51; 6) amino acids 55-57; 7) amino acids 61-62; 8) amino acids 81-83; 9) amino acids 91-92; 10) amino acids 102-105; wherein the amino acid numbering is based on the amino acid numbering of rat light chain as set forth in SEQ ID NO: 173 (sequence depicted in FIG. 12C).

In some cases, a sulfatase motif is introduced into the CH1 region of an anti-CD25 heavy chain constant region. In some cases, a sulfatase motif is introduced at or near (e.g., within 1 to 10 amino acids of) the C-terminus of an anti-CD25 heavy chain. In some cases, a sulfatase motif is introduced in the light-chain constant region.

In some cases, a sulfatase motif is introduced into the CH1 region of an anti-CD25 heavy chain constant region, e.g., within amino acids 121-219 of the IgG1 heavy chain amino acid sequence depicted in FIG. 12A. For example, in some cases, a sulfatase motif is introduced into the amino acid sequence: ASTKGPSVFPLAPSSKSTSGGTAAL-GCLVKDYFPEPVTVSWNSGALTSGVHTFPAVLQSS GLYS-LSSVVTVPSSSLGTQTYICNVNHKPSNTKVDKKVE (SEQ ID NO:138). For example, in some of these embodiments, the amino acid sequence GALTSGVH (SEQ ID NO:139) is modified to GALCTPSRGVH (SEQ ID NO:140), where the sulfatase motif is LCTPSR (SEQ ID NO:16).

In some cases, a sulfatase motif is introduced at or near the C-terminus of an anti-CD25 heavy chain, e.g., the sulfatase motifs introduced within 1 amino acid, 2 amino acids (aa), 3 aa, 4 aa, 5 aa, 6 aa, 7 aa, 8 aa, 9 aa, or 10 aa the C-terminus of an anti-CD25 heavy chain. As one non-limiting example, the C-terminal lysine reside of an anti-CD25 heavy chain can be replaced with the amino acid sequence SLCTPSRGS (SEQ ID NO:141).

In some cases, a sulfatase motif is introduced into the constant region of a light chain of an anti-CD25 antibody. As one non-limiting example, in some cases, a sulfatase motif is introduced into the constant region of a light chain of an anti-CD25 antibody, where the sulfatase motif is C-terminal to KVDNAL (SEQ ID NO:42), and/or is N-terminal to QSGNSQ (SEQ ID NO:43). For example, in some cases, the sulfatase motif is LCTPSR (SEQ ID NO:16), and the anti-CD25 light chain comprises the amino acid sequence KVDNALLCTPSRQSGNSQ (SEQ ID NO:142).

Drugs for Conjugation to a Polypeptide

The present disclosure provides drug-polypeptide conjugates. Examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent, such as a microtubule affecting agents. In certain embodiments, the drug is a microtubule affecting agent that has antiproliferative activity, such as a maytansinoid. In certain embodiments, the drug is a maytansinoid, which as the following structure:

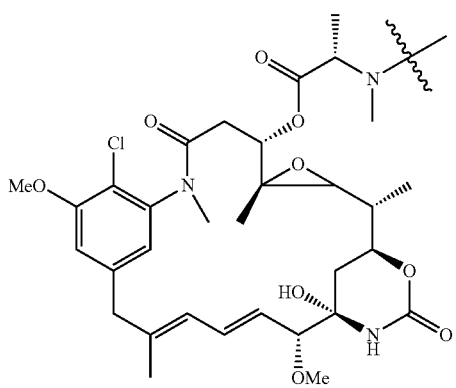

where ⁓ indicates the point of attachment between the maytansinoid and the linker, L, in formula (I). By "point of attachment" is meant that the ⁓ symbol indicates the bond between the N of the maytansinoid and the linker, L, in formula (I). For example, in formula (I), $W^1$ is a maytansinoid, such as a maytansinoid of the structure above, where ⁓ indicates the point of attachment between the maytansinoid and the linker, L.

As described above, in certain embodiments, L is a linker described by the formula -$(L^1)_a$-$(L^2)_b$-$(L^3)_c$-$(L^4)_d$-, wherein $L^1$, $L^2$, $L^3$ and $L^4$ are each independently a linker unit. In certain embodiments, $L^1$ is attached to the coupling moiety, such as a hydrazinyl-indolyl or a hydrazinyl-pyrrolo-pyridinyl coupling moiety (e.g., as shown in formula (I) above). In certain embodiments, $L^2$, if present, is attached to $W^1$ (the maytansinoid). In certain embodiments, $L^3$, if present, is attached to $W^1$ (the maytansinoid). In certain embodiments, $L^4$, if present, is attached to $W^1$ (the maytansinoid).

As described above, in certain embodiments, the linker -$(L^1)_a$-$(L^2)_b$-$(L^3)_c$-$(L^4)_d$- is described by the formula -$(T^1$-$V^1)_a$-$(T^2$-$V^2)_b$-$(T^3$-$V^3)_c$-$(T^4$-$V^4)_d$-, wherein a, b, c and d are each independently 0 or 1, where the sum of a, b, c and d is 1 to 4. In certain embodiments, as described above, $L^1$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to $W^1$ (the maytansinoid). In certain embodiments, as described above, $L^2$, if present, is attached to $W^1$ (the maytansinoid). As such, in certain embodiments, $T^2$, if present, is attached to $W^1$ (the maytansinoid), or $V^2$, if present, is attached to $W^1$ (the maytansinoid). In certain embodiments, as described above, $L^3$, if present, is attached to $W^1$ (the maytansinoid). As such, in certain embodiments, $T^3$, if present, is attached to $W^1$ (the maytansinoid), or $V^3$, if present, is attached to $W^1$ (the maytansinoid). In certain embodiments, as described above, $L^4$, if present, is attached to $W^1$ (the maytansinoid). As such, in certain embodiments, $T^4$, if present, is attached to $W^1$ (the maytansinoid), or $V^4$, if present, is attached to $W^1$ (the maytansinoid).

Embodiments of the present disclosure include conjugates where a polypeptide (e.g., anti-CD25 antibody) is conjugated to one or more drug moieties (e.g., maytansinoid), such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the polypeptide at one or more sites in the polypeptide, as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 2, such as 1, 1.1, 1.2, 1.3, 1.4, 1.5, 1.6, 1.7, 1.8, 1.9 or 2. In certain embodiments, the conjugates have an average DAR of 1.5 to 2. In certain embodiments, the conjugates have an average DAR of 1.75 to 1.85. In certain embodiments, the conjugates have an average DAR of 1.8. By average is meant the arithmetic mean.

Formulations

The conjugates of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

In some embodiments, provided is a pharmaceutical composition that includes any of the conjugates of the present disclosure and a pharmaceutically-acceptable excipient.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide).

In some embodiments, provided are methods that include administering to a subject an effective amount of any of the conjugates of the present disclosure.

In certain aspects, provided are methods of delivering a drug to a target site in a subject, the method including administering to the subject a pharmaceutical composition including any of the conjugates of the present disclosure, where the administering is effective to release a therapeutically effective amount of the drug from the conjugate at the target site in the subject.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

Methods of Treating Cancer

The present disclosure provides methods that include delivering a conjugate of the present disclosure to an individual having a cancer. The methods are useful for treating a wide variety of cancers, including carcinomas, sarcomas, leukemias, and lymphomas. In the context of cancer, the term "treating" includes one or more (e.g., each) of: reducing growth of a solid tumor, inhibiting replication of cancer cells, reducing overall tumor burden, and ameliorating one or more symptoms associated with a cancer.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

In certain aspects, provided are methods of treating cancer in a subject, such methods including administering to the subject a therapeutically effective amount of a pharmaceutical composition including any of the conjugates of the present disclosure, where the administering is effective to treat cancer in the subject. In some embodiments, the cancer is a hematologic malignancy. Hematologic malignancies of interest include, but are not limited to, leukemias, e.g., acute myeloid leukemia (AML). CD25 is up-regulated in refractory AML. In certain aspects, the methods are for treating relapsed and/or refractory AML. In some embodiments, the hematologic malignancy is lymphoma. CD25 is expressed on Hodgkin lymphoma (HL) cells and various T and B cell non-Hodgkin lymphoma (NHL) cells. When the hematologic malignancy is lymphoma, in certain aspects, the lymphoma is Hodgkin lymphoma (HL). When the lymphoma is Hodgkin lymphoma, in certain aspects, the Hodgkin lymphoma is relapsed and/or refractory Hodgkin lymphoma. When the hematologic malignancy is lymphoma, in certain aspects, the lymphoma is Non-Hodgkin lymphoma (NHL). When the lymphoma is Non-Hodgkin lymphoma, in certain aspects, the Non-Hodgkin lymphoma is relapsed and/or refractory Non-Hodgkin lymphoma.

Methods of Reducing Inhibitory Signals Derived from T Regulatory Cells in a Subject CD25 is expressed on regulatory T cells. As such, in certain aspects, provided are methods of reducing inhibitory signals derived from T regulatory cells in a subject, such methods including administering to the subject a therapeutically effective amount of any of the conjugates of the present disclosure, where the administering is effective to reduce inhibitory signals derived from T regulatory cells in the subject.

The methods of reducing inhibitory signals derived from T regulatory cells find use in a variety of contexts, including but not limited to, as part of an immunomodulatory combination therapy approach by reducing the inhibitory signals derived from the Treg populations and allowing for a productive anti-tumor immune response in a subject having cancer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

A linker containing a 4-amino-piperidine (4AP) group was synthesized according to Scheme 1, shown below.

Scheme 1

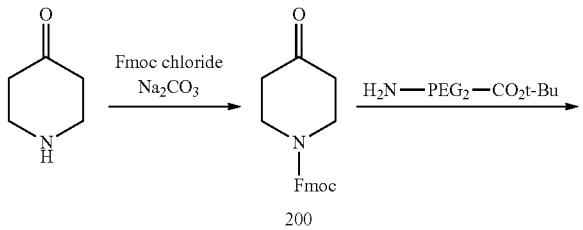

200

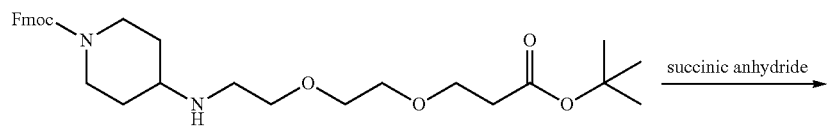

201

-continued
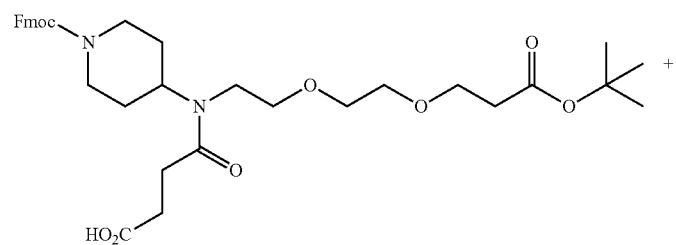
202
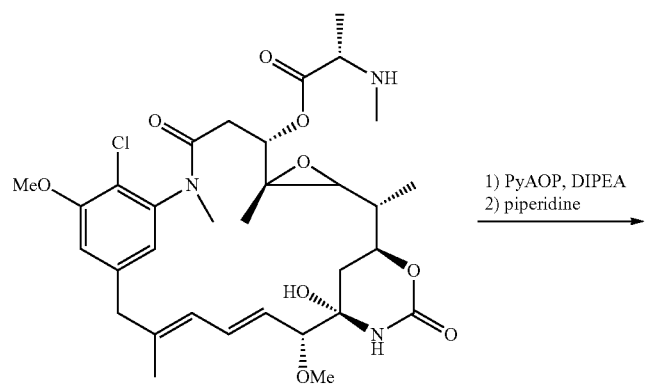
124
1) PyAOP, DIPEA
2) piperidine →
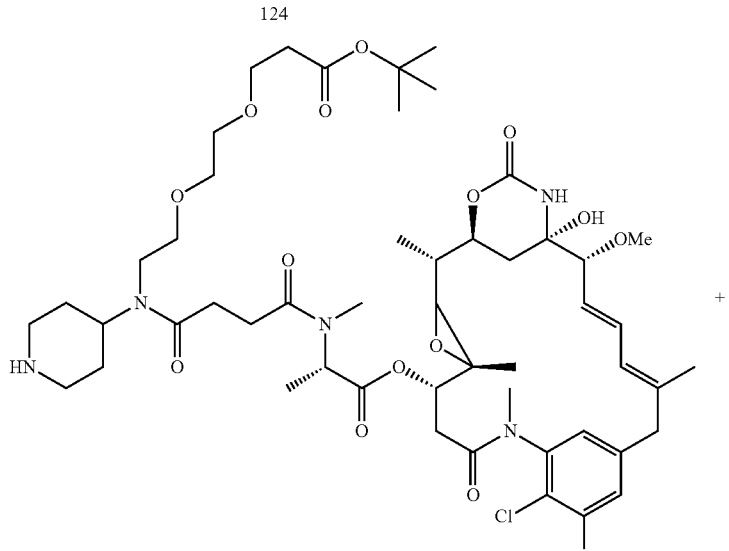
203
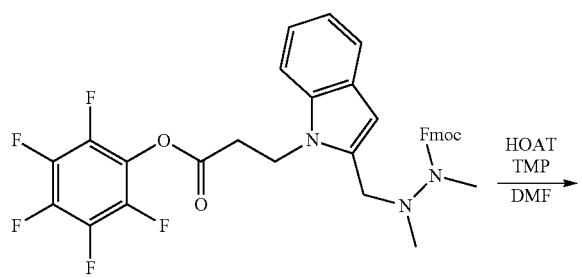
12
HOAT
TMP
DMF →

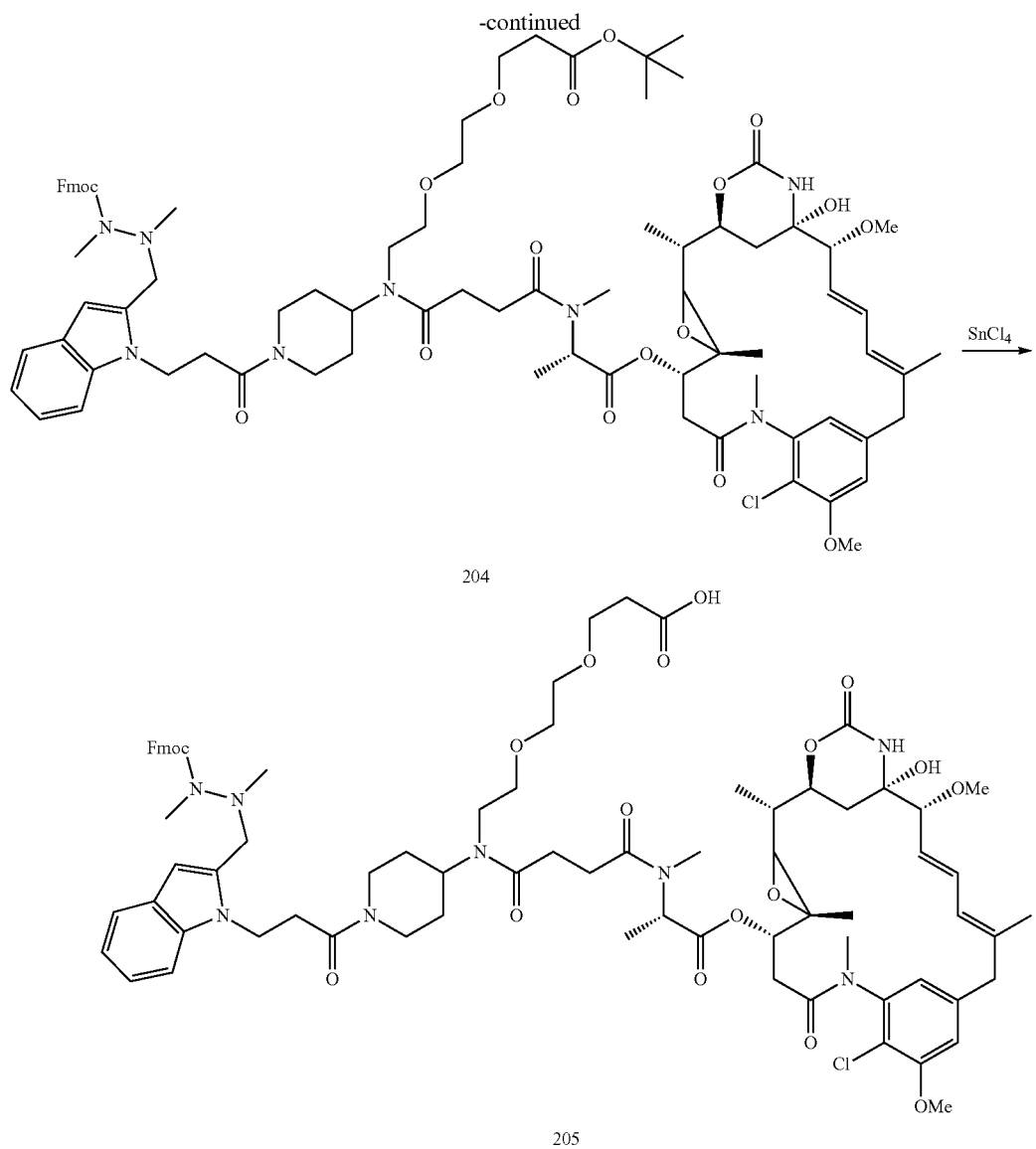

204

205

Synthesis of (9H-fluoren-9-yl)methyl 4-oxopiperidine-1-carboxylate (200)

To a 100 mL round-bottom flask containing a magnetic stir bar was added piperidin-4-one hydrochloride monohydrate (1.53 g, 10 mmol), Fmoc chloride (2.58 g, 10 mmol), sodium carbonate (3.18 g, 30 mmol), dioxane (20 mL), and water (2 mL). The reaction mixture was stirred at room temperature for 1 h. The mixture was diluted with EtOAc (100 mL) and extracted with water (1×100 mL). The organic layer was dried over $Na_2SO_4$, filtered, and concentrated under reduced pressure. The resulting material was dried in vacuo to yield compound 200 as a white solid (3.05 g, 95% yield).

$^1$H NMR (CDCl$_3$) δ 7.78 (d, 2H, J=7.6), 7.59 (d, 2H, J=7.2), 7.43 (t, 2H, J=7.2), 7.37 (t, 2H, J=7.2), 4.60 (d, 2H, J=6.0), 4.28 (t, 2H, J=6.0), 3.72 (br, 2H), 3.63 (br, 2H), 2.39 (br, 2H), 2.28 (br, 2H).

MS (ESI) m/z: [M+H]$^+$ Calcd for $C_{20}H_{20}NO_3$ 322.4; Found 322.2.

Synthesis of (9H-fluoren-9-yl)methyl 4-((2-(2-(3-(tert-butoxy)-3-oxopropoxy)ethoxy)ethyl)amino) piperidine-1-carboxylate (201)

To a dried scintillation vial containing a magnetic stir bar was added piperidinone 200 (642 mg, 2.0 mmol), $H_2N$-PEG$_2$-CO$_2$t-Bu (560 mg, 2.4 mmol), 4 Å molecular sieves (activated powder, 500 mg), and 1,2-dichloroethane (5 mL). The mixture was stirred for 1 h at room temperature. To the reaction mixture was added sodium triacetoxyborohydride (845 mg, 4.0 mmol). The mixture was stirred for 5 days at room temperature. The resulting mixture was diluted with EtOAc. The organic layer was washed with saturated NaHCO$_3$ (1×50 mL), and brine (1×50 mL), dried over $Na_2SO_4$, filtered, and concentrated under reduced pressure to yield compound 201 as an oil, which was carried forward without further purification. Synthesis of 13-(1-(((9H-fluoren-9-yl)methoxy)carbonyl)piperidin-4-yl)-2,2-dimethyl-4,14-dioxo-3,7,10-trioxa-13-azaheptadecan-17-oic acid (202)

To a dried scintillation vial containing a magnetic stir bar was added N-Fmoc-piperidine-4-amino-PEG$_2$-CO$_2$t-Bu (201) from the previous step, succinic anhydride (270 mg, 2.7 mmol), and dichloromethane (5 mL). The mixture was stirred for 18 hours at room temperature. The reaction mixture was partitioned between EtOAc and saturated NaHCO$_3$. The aqueous layer was extracted with EtOAc (3×). The aqueous layer was acidified with HCl (1 M) until the pH ~3. The aqueous layer was extracted (3×) with DCM. The combined organic layers were dried over Na$_2$SO$_4$, filtered, and concentrated under reduced pressure. The reaction mixture was purified by C18 flash chromatography (elute 10-100% MeCN/water with 0.1% acetic acid). Product-containing fractions were concentrated under reduced pressure and then azeotroped with toluene (3×50 mL) to remove residual acetic acid to afford 534 mg (42%, 2 steps) of compound 202 as a white solid.

$^1$H NMR (DMSO-d$_6$) δ 11.96 (br, 1H), 7.89 (d, 2H, J=7.2), 7.63 (d, 2H, J=7.2), 7.42 (t, 2H, J=7.2), 7.34 (t, 2H, J=7.2), 4.25-4.55 (m, 3H), 3.70-4.35 (m, 3H), 3.59 (t, 2H, J=6.0), 3.39 (m, 5H), 3.35 (m, 3H), 3.21 (br, 1H), 2.79 (br, 2H), 2.57 (m, 2H), 2.42 (q, 4H, J=6.0), 1.49 (br, 3H), 1.37 (s, 9H).

MS (ESI) m/z: [M+H]$^+$ Calcd for C$_{35}$H$_{47}$N$_2$O$_9$ 639.3; Found 639.2.

Synthesis of (2S)-1-(((1$^4$S,1$^6$S,3$^3$S,2R,4S,10E,12E, 14R)-8$^6$-chloro-1$^4$-hydroxy-8$^5$,14-dimethoxy-3$^3$,2,7, 10-tetramethyl-1$^2$,6-dioxo-7-aza-1 (6,4)-oxazinana-3 (2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (203)

To a solution of ester 202 (227 mg, 0.356 mmol), diisopropylethylamine (174 µL, 1.065 mmol), N-deacetyl maytansine 124 (231 mg, 0.355 mmol) in 2 mL of DMF was added PyAOP (185 mg, 0.355 mmol). The solution was stirred for 30 min. Piperidine (0.5 mL) was added to the reaction mixture and stirred for an additional 20 min. The crude reaction mixture was purified by C18 reverse phase chromatography using a gradient of 0-100% acetonitrile:water affording 203.2 mg (55%, 2 steps) of compound 203.

Synthesis of 17-(tert-butyl) 1-((1$^4$S,1$^6$S,3$^3$S,2R,4S, 10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(3-(2- ((2-(((9H-fluoren-9-yl)methoxy)carbonyl)-1,2-dimethylhydrazinyl)methyl)-1H-indol-1-yl)propanoyl)piperidin-4-yl)-2,3-dimethyl-4,7-dioxo-11,14-dioxa-3,8-diazaheptadecanedioate (204)

A solution of piperidine 203 (203.2 mg, 0.194 mmol), ester 12 (126.5 mg, 0.194 mmol), 2,4,6-trimethylpyridine (77 µL, 0.582 mmol), HOAT (26.4 mg, 0.194 mmol) in 1 mL DMF was stirred 30 min. The crude reaction was purified by C18 reverse phase chromatography using a gradient of 0-100% acetonitrile:water with 0.1% formic acid affording 280.5 mg (97% yield) of compound 204.

MS (ESI) m/z: [M+H]$^+$ Calcd for C$_{81}$H$_{106}$ClN$_8$O$_{18}$ 1513.7; Found 1514.0.

Synthesis of (2S)-8-(1-(3-(2-((2-(((9H-fluoren-9-yl) methoxy)carbonyl)-1,2-dimethylhydrazinyl)methyl)-1H-indol-1-yl)propanoyl)piperidin-4-yl)-1-(((1$^4$S, 1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2, 3-dimethyl-1,4,7-trioxo-11,14-dioxa-3,8-diazaheptadecan-17-oic acid (205)

To a solution of compound 204 (108 mg, 0.0714 mmol) in 500 µL anhydrous DCM was added 357 µL of a 1M solution of SnCl$_4$ in DCM. The heterogeneous mixture was stirred for 1 h and then purified by C18 reverse phase chromatography using a gradient of 0-100% acetonitrile: water with 0.1% formic acid affording 78.4 mg (75% yield) of compound 205.

MS (ESI) m/z: [M-H]$^-$ Calcd for C$_{77}$H$_{96}$ClN$_8$O$_{18}$ 1455.7; Found 1455.9.

Example 2

A linker containing a 4-amino-piperidine (4AP) group was synthesized according to Scheme 2, shown below.

Scheme 2

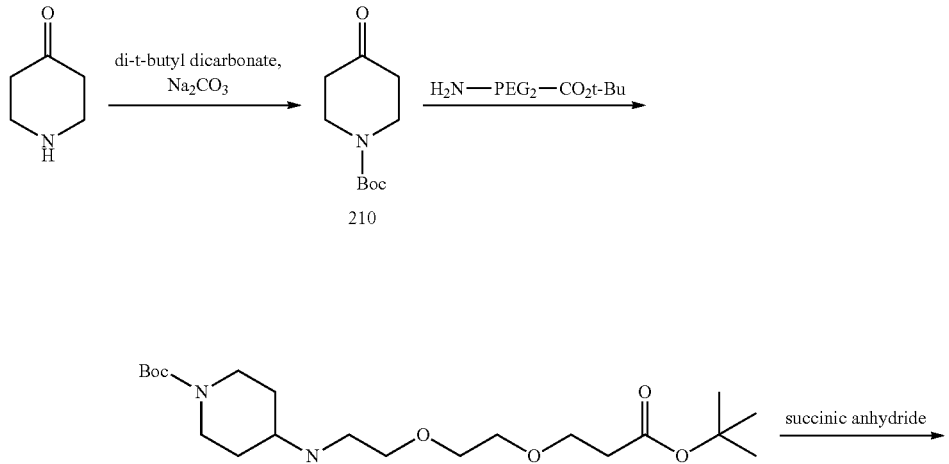

-continued
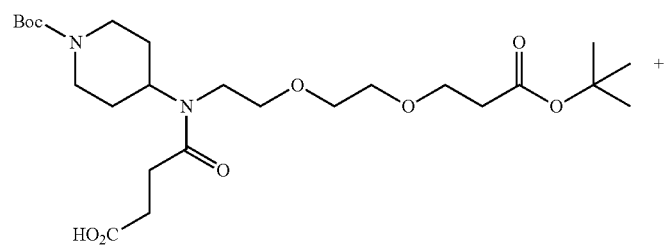
212
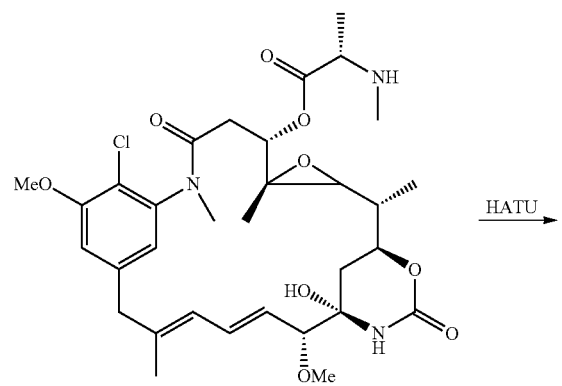
124
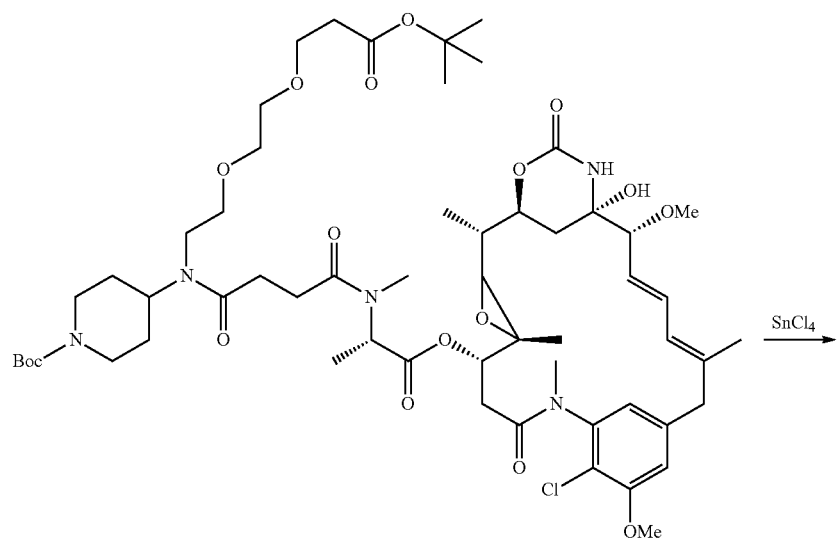
213

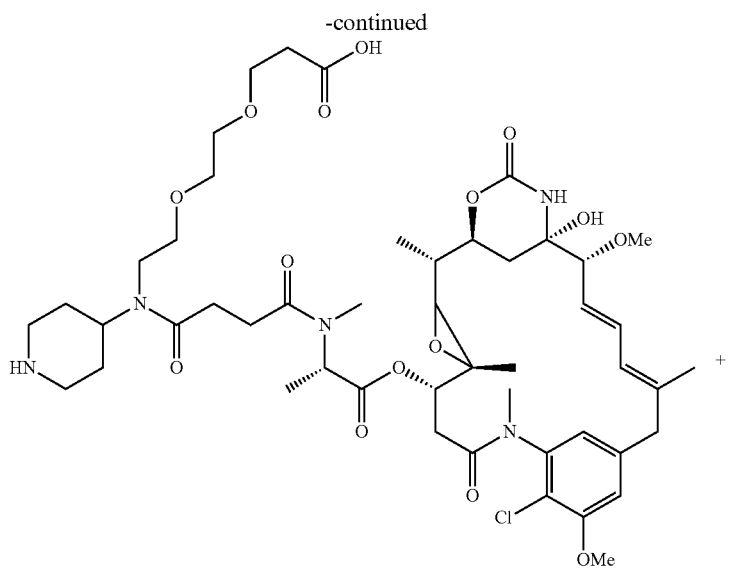
214
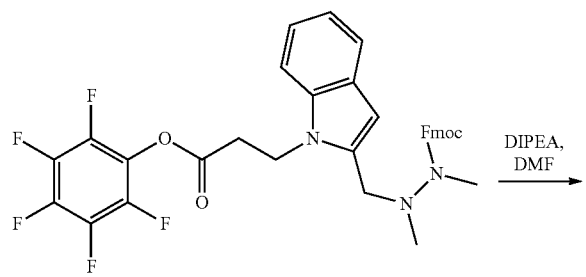
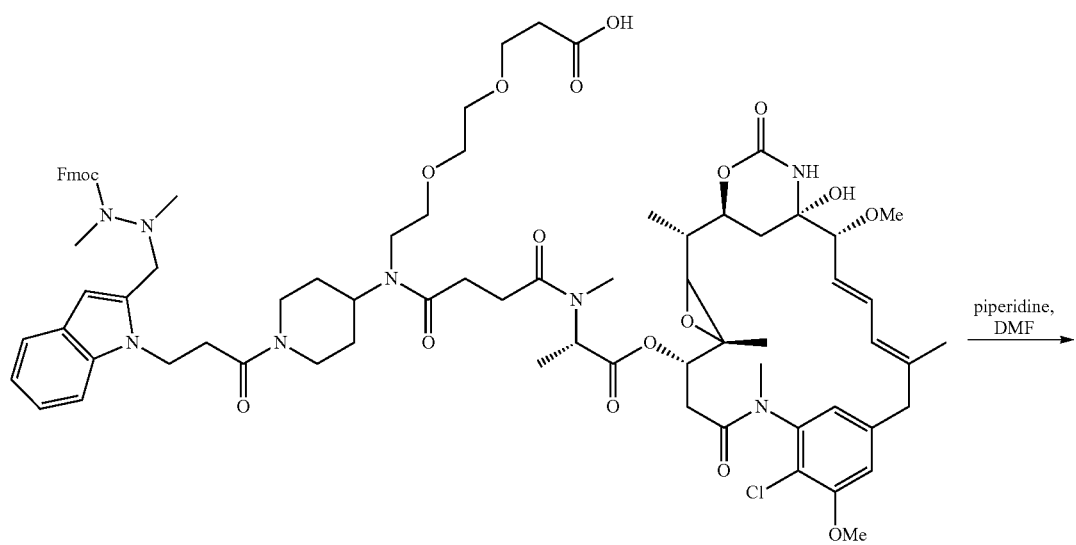
215

-continued

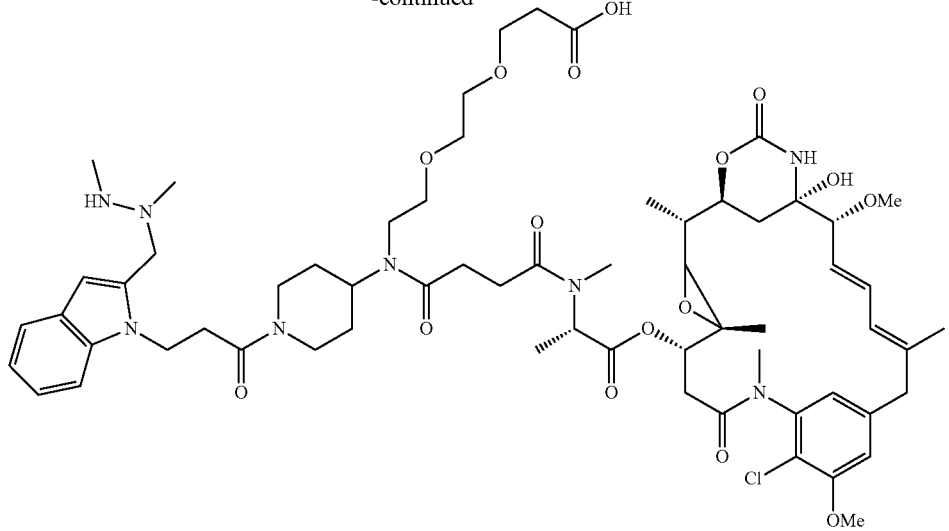

216

Synthesis of tert-butyl 4-oxopiperidine-1-carboxylate (210)

To a 100 mL round-bottom flask containing a magnetic stir bar was added piperidin-4-one hydrochloride monohydrate (1.53 g, 10 mmol), di-tert-butyl dicarbonate (2.39 g, 11 mmol), sodium carbonate (1.22 g, 11.5 mmol), dioxane (10 mL), and water (1 mL). The reaction mixture was stirred at room temperature for 1 h. The mixture was diluted with water (100 mL) and extracted with EtOAc (3×100 mL). The combined organic layers were washed with brine, dried over $Na_2SO_4$, filtered, and concentrated under reduced pressure. The resulting material was dried in vacuo to yield 1.74 g (87%) of compound 210 as a white solid.

$^1$H NMR (CDCl$_3$) δ 3.73 (t, 4H, J=6.0), 2.46 (t, 4H, J=6.0), 1.51 (s, 9H).

MS (ESI) m/z: [M+H]$^+$ Calcd for $C_{10}H_{18}NO_3$ 200.3; Found 200.2.

Synthesis of tert-butyl 4-((2-(2-(3-(tert-butoxy)-3-oxopropoxy)ethoxy)ethyl)amino)piperidine-1-carboxylate (211)

To a dried scintillation vial containing a magnetic stir bar was added tert-butyl 4-oxopiperidine-1-carboxylate (399 mg, 2 mmol), $H_2N$-PEG$_2$-COOt-Bu (550 mg, 2.4 mmol), 4 Å molecular sieves (activated powder, 200 mg), and 1,2-dichloroethane (5 mL). The mixture was stirred for 1 h at room temperature. To the reaction mixture was added sodium triacetoxyborohydride (845 mg, 4 mmol). The mixture was stirred for 3 days at room temperature. The resulting mixture was partitioned between EtOAc and saturated aqueous NaHCO$_3$. The organic layer was washed with brine, dried over $Na_2SO_4$, filtered, and concentrated under reduced pressure to afford 850 mg of compound 211 as a viscous oil.

MS (ESI) m/z: [M+H]$^+$ Calcd for $C_{21}H_{41}N_2O_6$ 417.3; Found 417.2.

Synthesis of 13-(1-(tert-butoxycarbonyl)piperidin-4-yl)-2,2-dimethyl-4,14-dioxo-3,7,10-trioxa-13-azaheptadecan-17-oic acid (212)

To a dried scintillation vial containing a magnetic stir bar was added tert-butyl 4-((2-(2-(3-(tert-butoxy)-3-oxopropoxy)ethoxy)ethyl)amino)piperidine-1-carboxylate 211 (220 mg, 0.5 mmol), succinic anhydride (55 mg, 0.55 mmol), 4-(dimethylamino)pyridine (5 mg, 0.04 mmol), and dichloromethane (3 mL). The mixture was stirred for 24 h at room temperature. The reaction mixture was partially purified by flash chromatography (elute 50-100% EtOAc/hexanes) to yield 117 mg of compound 212 as a clear oil, which was carried forward without further characterization.

MS (ESI) m/z: [M+H]$^+$ Calcd for $C_{25}H_{45}N_2O_9$ 517.6; Found 517.5.

Synthesis of 17-(tert-butyl) 1-((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(tert-butoxycarbonyl)piperidin-4-yl)-2,3-dimethyl-4,7-dioxo-11,14-dioxa-3,8-diazaheptadecanedioate (213)

To a dried scintillation vial containing a magnetic stir bar was added 13-(1-(tert-butoxycarbonyl)piperidin-4-yl)-2,2-dimethyl-4,14-dioxo-3,7,10-trioxa-13-azaheptadecan-17-oic acid 212 (55 mg, 0.1 mmol), N-deacyl maytansine 124 (65 mg, 0.1 mmol), HATU (43 mg, 0.11 mmol), DMF (1 mL), and dichloromethane (0.5 mL). The mixture was stirred for 8 h at room temperature. The reaction mixture was directly purified by C18 flash chromatography (elute 5-100% MeCN/water) to give 18 mg (16%) of compound 213 as a white film.

MS (ESI) m/z: [M+H]$^+$ Calcd for $C_{57}H_{87}ClN_5O_7$ 1148.6; Found 1148.7.

Synthesis of (2S)-1-(((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (214)

To a dried scintillation vial containing a magnetic stir bar was added maytansinoid 213 (31 mg, 0.027 mmol) and dichloromethane (1 mL). The solution was cooled to 0° C. and tin(IV) tetrachloride (1.0 M solution in dichloromethane, 0.3 mL, 0.3 mmol) was added. The reaction mixture was stirred for 1 h at 0° C. The reaction mixture was directly purified by C18 flash chromatography (elute 5-100% MeCN/water) to yield 16 mg (60%) of compound 214 as a white solid (16 mg, 60% yield).

MS (ESI) m/z: [M+H]$^+$ Calcd for $C_{48}H_{71}ClN_5O_5$ 992.5; Found 992.6.

Synthesis of (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-(((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (215)

To a dried scintillation vial containing a magnetic stir bar was added maytansinoid 214 (16 mg, 0.016 mmol), (9H-fluoren-9-yl)methyl 1,2-dimethyl-2-((1-(3-oxo-3-(perfluorophenoxy)propyl)-1H-indol-2-yl)methyl)hydrazine-1-carboxylate (5) (13 mg, 0.02 mmol), DIPEA (8 μL, 0.05 mmol), and DMF (1 mL). The solution was stirred for 18 h at room temperature. The reaction mixture was directly purified by C18 flash chromatography (elute 5-100% MeCN/water) to yield 18 mg (77%) of compound 215 as a white solid.

MS (ESI) m/z: [M+H]$^+$ Calcd for $C_{77}H_{98}ClN_8O_8$ 1457.7; Found 1457.9.

Synthesis of (2S)-1-(((1$^4$S,1$^6$S,3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl)methyl)-1H-indol-1-yl)propanoyl)piperidin-4-yl)-2,3-dimethyl-1,4,7-trioxo-11,14-dioxa-3,8-diazaheptadecan-17-oic acid (216)

To a dried scintillation vial containing a magnetic stir bar was added maytansinoid 215 (18 mg, 0.012 mmol), piperidine (20 μL, 0.02 mmol), and DMF (1 mL). The solution was stirred for 20 minutes at room temperature. The reaction mixture was directly purified by C18 flash chromatography (elute 1-60% MeCN/water) to yield 15 mg (98%) of compound 216 (also referred to herein as HIPS-4AP-maytansine or HIPS-4-amino-piperidin-maytansine) as a white solid.

MS (ESI) m/z: [M+H]$^+$ Calcd for $C_{62}H_{88}ClN_8O_{16}$ 1235.6; Found 1236.0.

Example 3

Experimental Procedures
General

Experiments were performed to create site-specifically conjugated antibody-drug conjugates (ADCs). Site-specific ADC production included the incorporation of formylglycine (FGly), a non-natural amino acid, into the protein sequence. To install FGly (FIG. 1), a short consensus sequence, CXPXR, (SEQ ID NO: 174) where X is serine, threonine, alanine, or glycine, was inserted at the desired location in the conserved regions of antibody heavy or light chains using standard molecular biology cloning techniques. This "tagged" construct was produced recombinantly in cells that coexpress the formylglycine-generating enzyme (FGE), which cotranslationally converted the cysteine within the tag into an FGly residue, generating an aldehyde functional group (also referred to herein as an aldehyde tag). The aldehyde functional group served as a chemical handle for bioorthogonal conjugation. A hydrazino-iso-Pictet-Spengler (HIPS) ligation was used to connect the payload (e.g., a drug, such as a cytotoxin (e.g., maytansine)) to FGly, resulting in the formation of a stable, covalent C═C bond between the cytotoxin payload and the antibody. This C═C bond was expected to be stable to physiologically-relevant conditions encountered by the ADC during circulation and FcRn recycling, e.g., proteases, low pH, and reducing reagents. Antibodies bearing the aldehyde tag may be produced at a variety of locations. Experiments were performed to test the effects of inserting the aldehyde tag at the heavy chain C-terminus (CT). Biophysical and functional characteriziaton was performed on the resulting ADCs made by conjugation to maytansine payloads via a HIPS linker.

Cloning, Expression, and Purification of Tagged Antibodies

The aldehyde tag sequence was inserted at the heavy chain C-terminus (CT) of the anti-CD25 antibody daclizumab using standard molecular biology techniques. For small-scale production, CHO—S cells were transfected with human FGE expression constructs and pools of FGE-over-expressing cells were used for the transient production of antibodies. For larger-scale production, GPEx technology (Catalent, Inc., Somerset, NJ) was used to generate a clonal cell line overexpressing human FGE (GPEx). Then, the FGE clone was used to generate bulk stable pools of antibody-expressing cells. Antibodies were purified from the conditioned medium using a Protein A chromatography (MabSelect, GE Healthcare Life Sciences, Pittsburgh, PA). Purified antibodies were flash frozen and stored at −80° C. until further use.

Bioconjugation, Purification, and HPLC Analytics

C-terminally aldehyde-tagged aCD25 antibody (daclizumab, 15 mg/mL) was conjugated to a maytansine payload attached to a HIPS-4AP linker (8 mol. equivalents drug:antibody) for 48-72 h at 37° C. in 20 mM sodium citrate, 50 mM NaCl pH 5.0 containing 0.85% DMA. After conjugation, free drug was removed by tangential flow filtration and the ADC was buffer exchanged into 20 mM sodium citrate, 50 mM NaCl pH 5.5.

To determine the drug-to-antibody ratio (DAR) of the final product, ADCs were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0. To determine aggregation, samples were analyzed using analytical size exclusion chromatography (SEC; Tosoh #08541) with a mobile phase of 300 mM NaCl, 25 mM sodium phosphate pH 6.8.

Results

The anti-CD25 antibody modified to contain the aldehyde tag at the heavy chain C-terminus (CT) was conjugated to a maytansine payload attached to a HIPS-4AP linker. Upon completion, remaining free drug was removed during buffer exchange by tangential flow filtration. These reactions were high yielding, with >90% conjugation efficiency and >80% total yield. The resulting ADCs had drug-to-antibody ratios (DARs) of 1.75-1.84 and were predominately monomeric. FIGS. 2-5 document DARs from representative reactions as determined by HIC and reversed phase PLRP chromatography, and show the monomeric integrity as determined by SEC.

Figure 2:
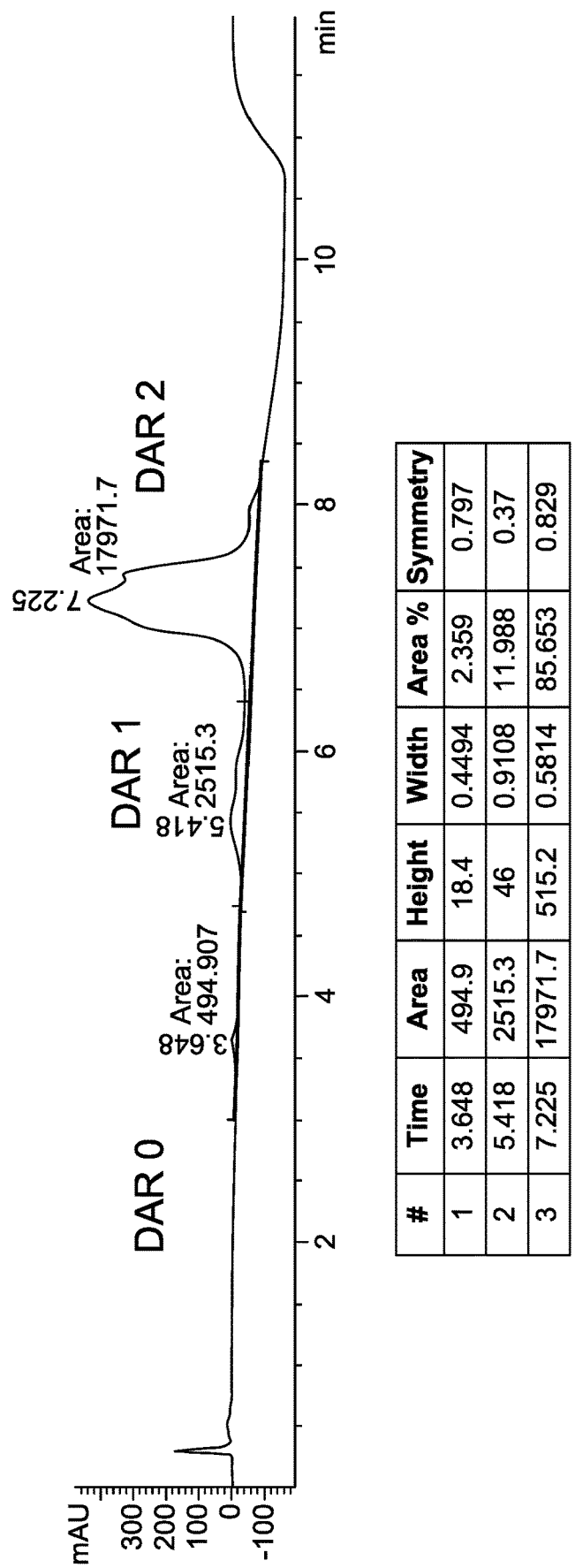
FIG. 2 shows a hydrophobic interaction column (HIC) trace of an aldehyde-tagged anti-CD25 antibody conjugated at the heavy chain C-terminus to a maytansine payload attached to a HIPS-4AP linker, according to embodiments of the present disclosure.

FIG. 2 shows a hydrophobic interaction column (HIC) trace of an aldehyde-tagged anti-CD25 antibody conjugated at the heavy chain C-terminus (CT) to a maytansine payload attached to a HIPS-4AP linker. FIG. 2 indicates that the DAR was 1.83 as determined by HIC.

Figure 3:
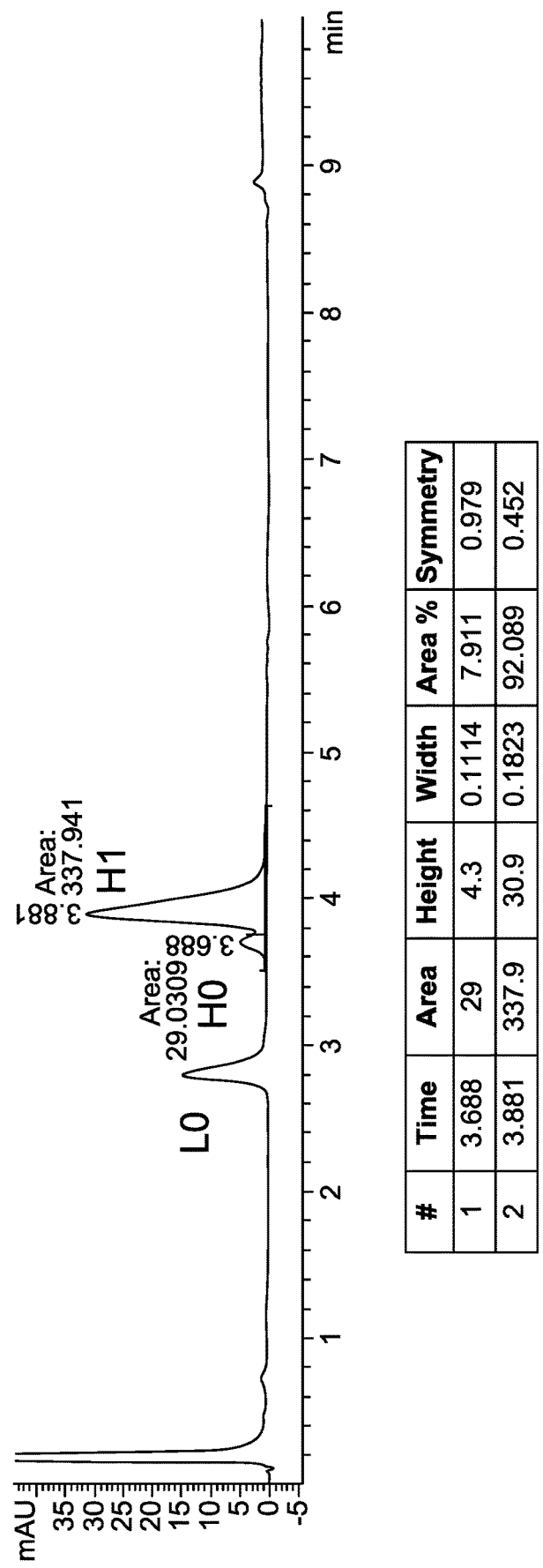
FIG. 3 shows a reversed phase chromatography (PLRP) trace of an aldehyde-tagged anti-CD25 antibody conjugated at the heavy chain C-terminus to a maytansine payload attached to a HIPS-4AP linker, according to embodiments of the present disclosure.

FIG. 3 shows a reversed phase chromatography (PLRP) trace of an aldehyde-tagged anti-CD25 antibody conjugated at the heavy chain C-terminus (CT) to a maytansine payload attached to a HIPS-4AP linker. FIG. 3 indicates that the DAR was 1.81 as determined by PLRP.

Figure 4:
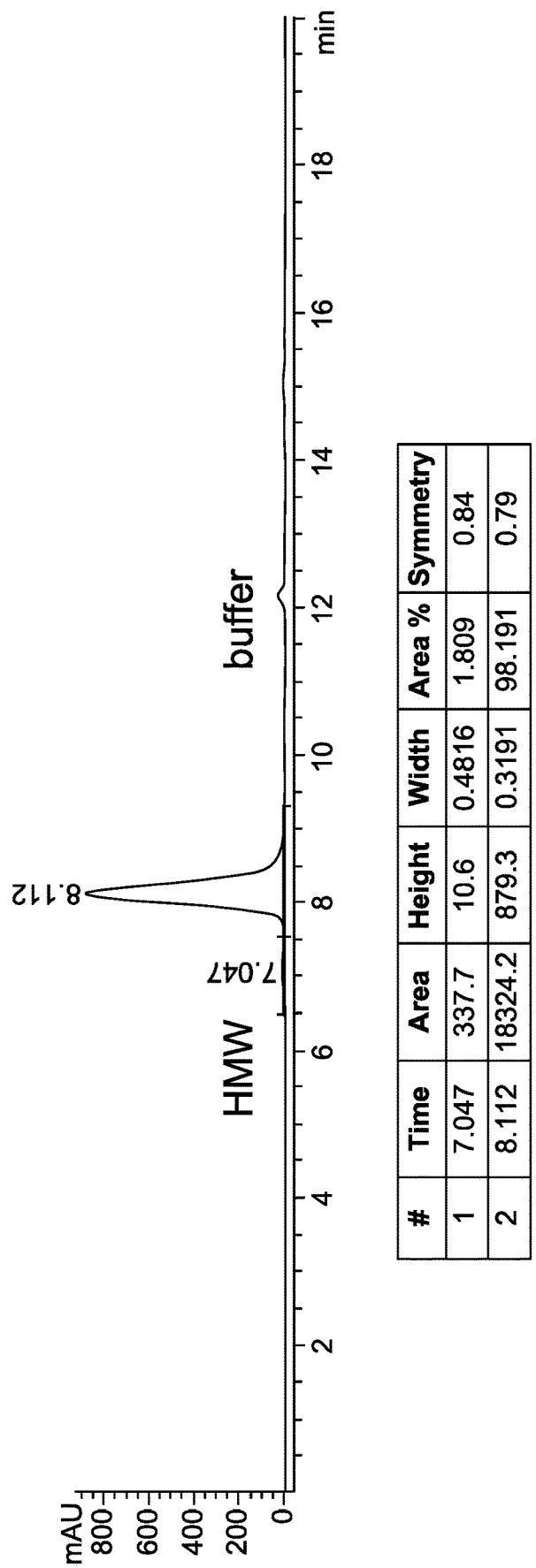
FIG. 4 shows a graph of analytical size exclusion chromatography (SEC) analysis of an aldehyde-tagged anti-CD25 antibody conjugated at the heavy chain C-terminus (CT) to a maytansine payload attached to a HIPS-4AP linker, according to embodiments of the present disclosure.

FIG. 4 shows a graph of analytical size exclusion chromatography (SEC) analysis of an aldehyde-tagged anti-CD25 antibody conjugated at the heavy chain C-terminus (CT) to a maytansine payload attached to a HIPS-4AP linker. As shown in FIG. 4, analytical SEC indicated 98.2% monomer for the final product.

Figure 5:
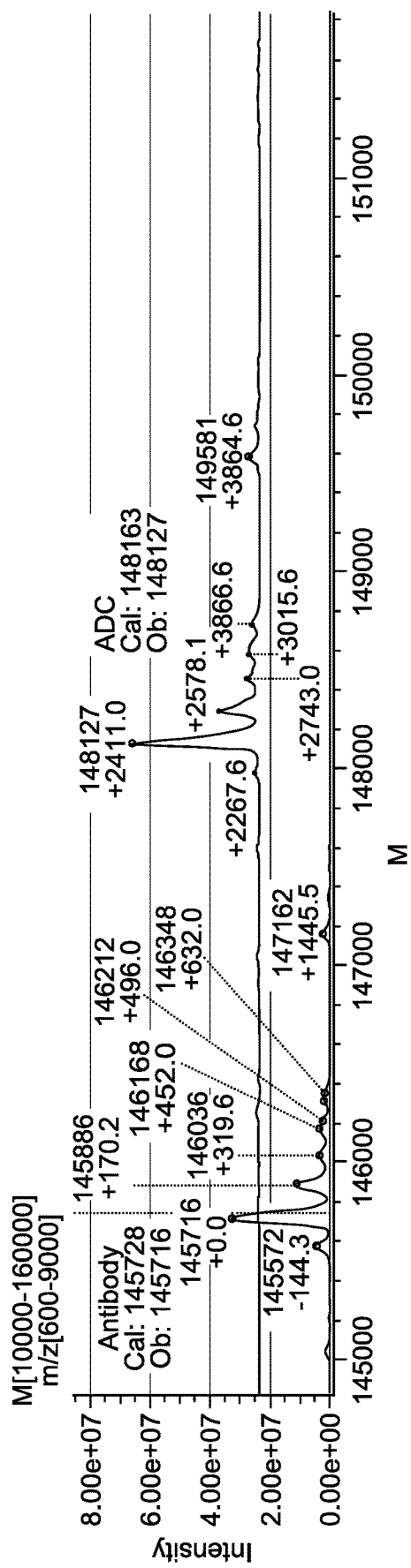
FIG. 5 shows a graph of intact mass analysis of an aldehyde-tagged anti-CD25 antibody conjugated at the heavy chain C-terminus to a maytansine payload attached to a HIPS-4AP linker, according to embodiments of the present disclosure.
Figure 6:
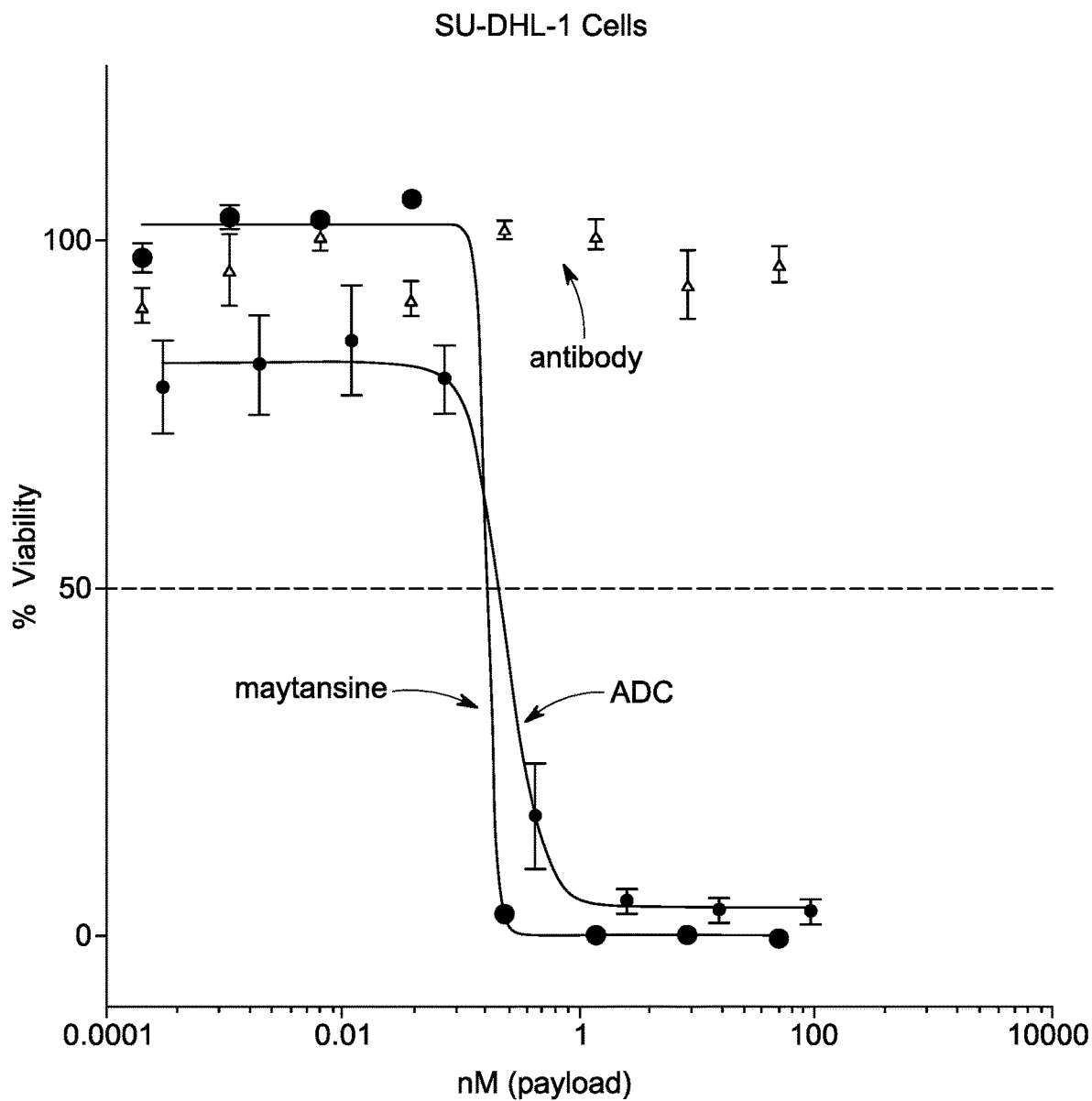
FIG. 6 shows in vitro cytotoxicity data for an aldehyde-tagged anti-CD25 antibody conjugated at the heavy chain C-terminus to a maytansine payload attached to a HIPS-4AP linker in SU-DHL-1 cells, according to embodiments of the present disclosure.
Figure 7:
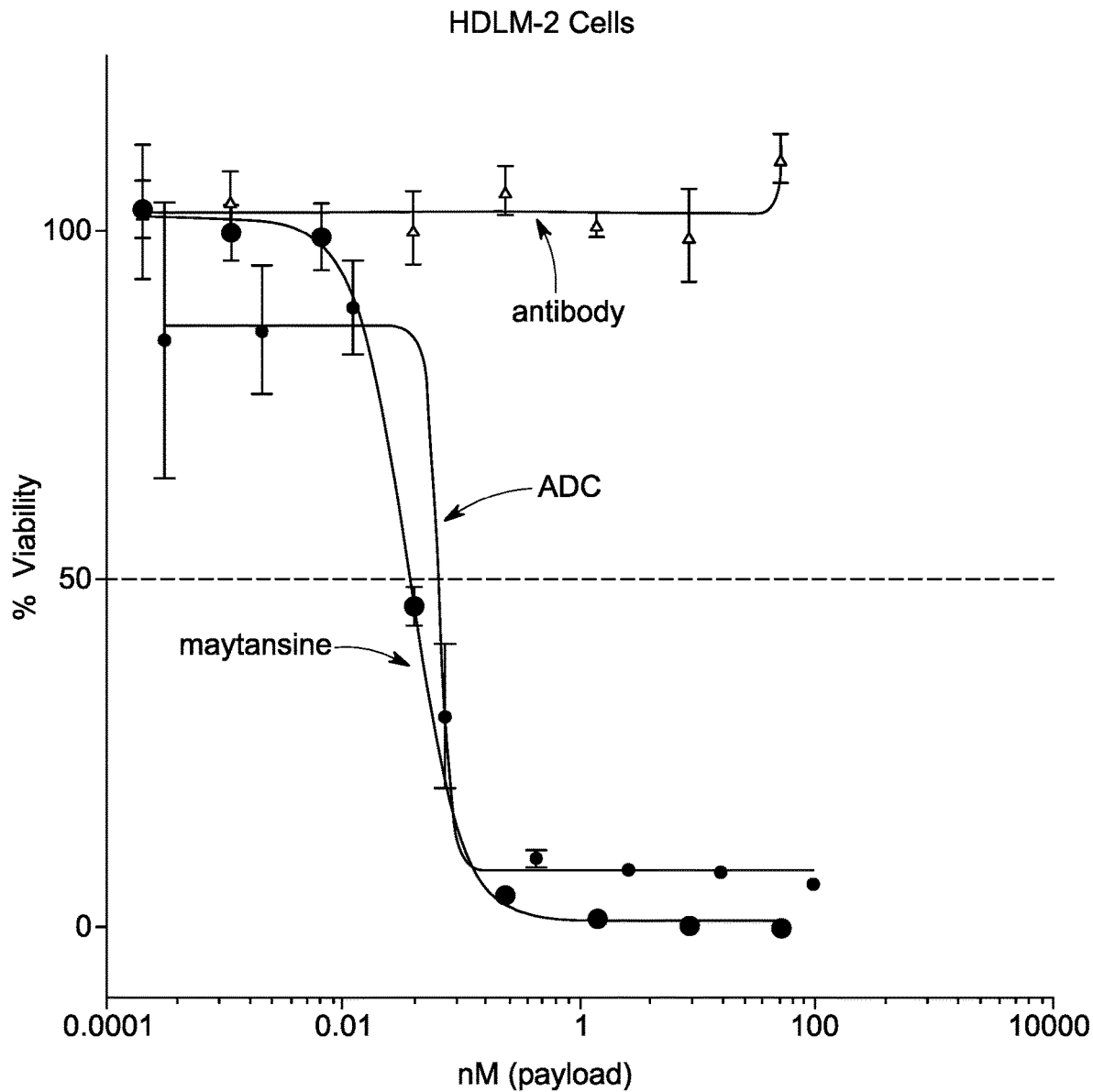
FIG. 7 shows in vitro cytotoxicity data for an aldehyde-tagged anti-CD25 antibody conjugated at the heavy chain C-terminus to a maytansine payload attached to a HIPS-4AP linker in HDLM-2 cells, according to embodiments of the present disclosure.
Figure 8:
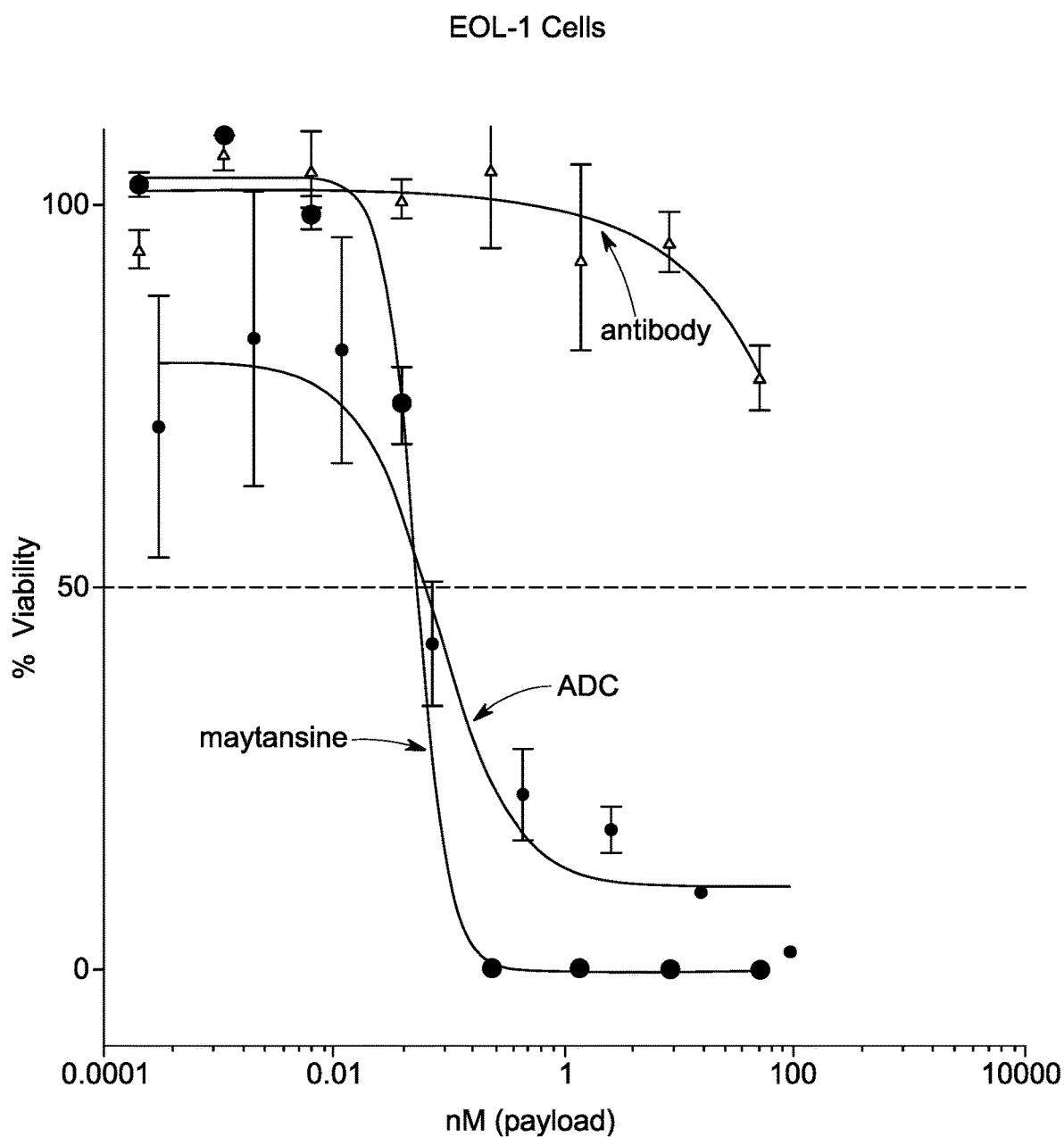
FIG. 8 shows in vitro cytotoxicity data for an aldehyde-tagged anti-CD25 antibody conjugated at the heavy chain C-terminus to a maytansine payload attached to a HIPS-4AP linker in EoL-1 cells, according to embodiments of the present disclosure.
Figure 9:
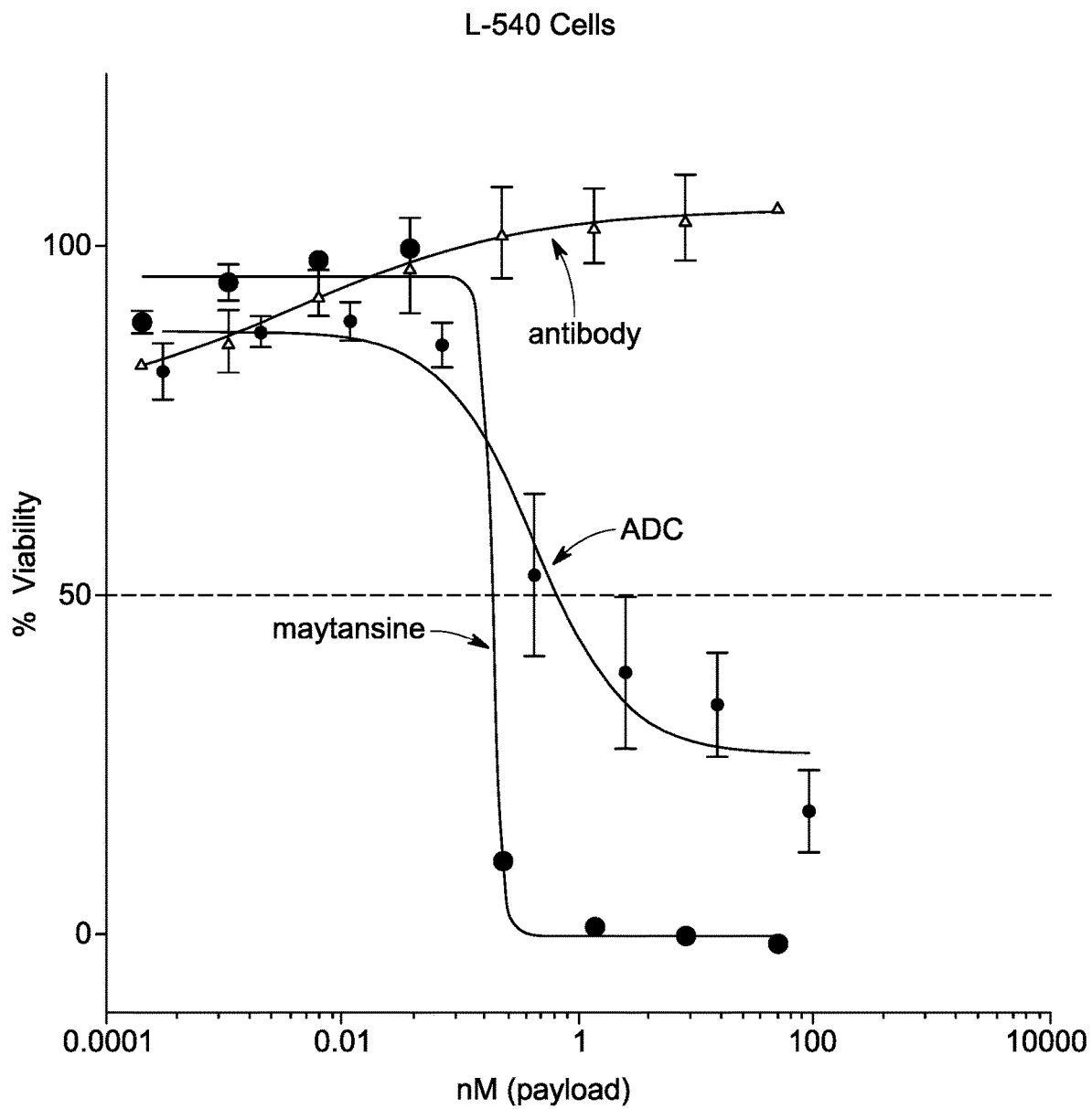
FIG. 9 shows in vitro cytotoxicity data for an aldehyde-tagged anti-CD25 antibody conjugated at the heavy chain C-terminus to a maytansine payload attached to a HIPS-4AP linker in L-540 cells, according to embodiments of the present disclosure.
Figure 10:
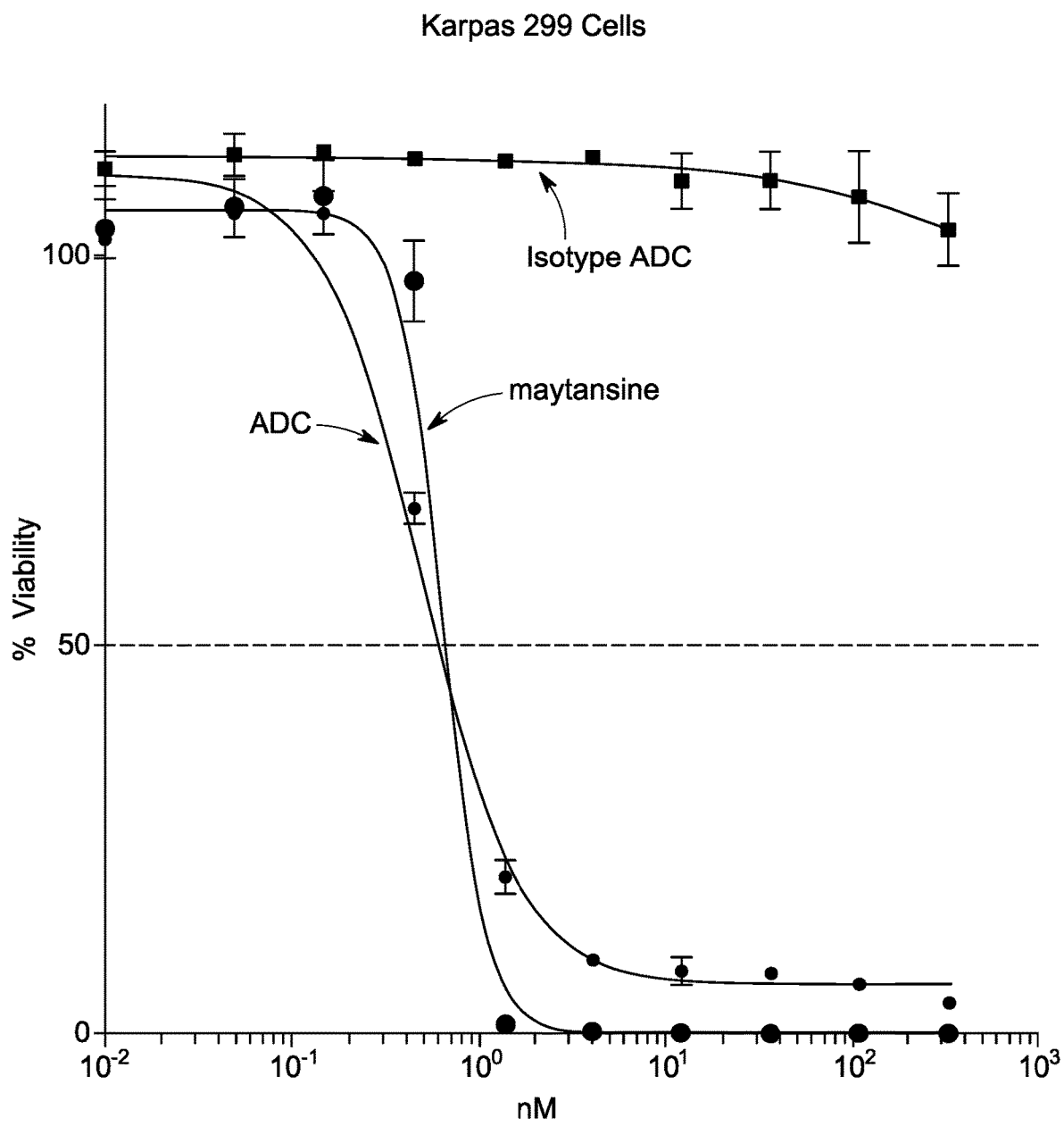
FIG. 10 shows in vitro cytotoxicity data for an aldehyde-tagged anti-CD25 antibody conjugated at the heavy chain C-terminus to a maytansine payload attached to a HIPS-4AP linker in Karpas 299 cells, according to embodiments of the present disclosure.

FIG. 5 shows a graph of intact mass analysis of an aldehyde-tagged anti-CD25 antibody conjugated at the heavy chain C-terminus (CT) to a maytansine payload attached to a HIPS-4AP linker. As shown in FIG. 5, a linker/payload-related increase in mass for a DAR2 conjugated species was observed.

In Vitro Cytotoxicity

The CD25-positive leukemia and lymphoma cell lines, SU-DHL-1, HDLM-2, EoL-1, L-540, and Karpas 299, were obtained from the ATCC and DSMZ cell banks, or were tested at Crown Bioscience, Inc. The cells were maintained in RPMI-1640 medium (Cellgro) supplemented with 10 or 20% fetal bovine serum (Invitrogen) and Glutamax (Invitrogen). 24 h prior to plating, cells were passaged to ensure log-phase growth. On the day of plating, 5000 cells/well were seeded onto 96-well plates in 100 µL normal growth medium supplemented with 10 IU penicillin and 10 µg/mL streptomycin (Cellgro). Cells were treated at various concentrations with 20 µL of diluted analytes, and the plates were incubated at 37° C. in an atmosphere of 5% $CO_2$. After 5 d, 100 µL/well of Cell Titer-Glo reagent (Promega) was added, and luminescence was measured using a Molecular Devices SpectraMax M5 plate reader. GraphPad Prism software was used for data analysis.

Results

The anti-CD25 HIPS-4AP-maytansine conjugate exhibited very potent activity against all five tested cell lines, comparable to free maytansine. FIGS. 6-10 show the results for the SU-DHL-1 ($IC_{50}$: 0.24 nM), HDLM-2 ($IC_{50}$: 0.06 nM), EoL-1 ($IC_{50}$: 0.07 nM), L-540 ($IC_{50}$: 0.43 nM), and Karpas 299 ($IC_{50}$: 0.49 nM) cell lines, respectively. The ADC $IC_{50}$ concentrations ranged from 0.06 to 0.49 nM in these assays, while the free maytansine $IC_{50}$ concentrations ranged from 0.03 to 0.19 nM.

Xenograft Studies

Female CB17.SCID mice (6/group) were inoculated subcutaneously with $5\times10^6$ Karpas 299 cells. Treatment began when the tumors reached an average of 205 mm³, at which time the animals were dosed intravenously with vehicle alone or the anti-CD25 HIPS-4AP-maytansine conjugate (10 mg/kg). One group received a single dose of the anti-CD25 HIPS-4AP-maytansine conjugate, while another group was dosed once per week for a total of four doses (qwk×4). The animals were monitored twice weekly for body weight and tumor size. Animals were euthanized when tumors reached 2000 mm³.

Results

Figure 11:
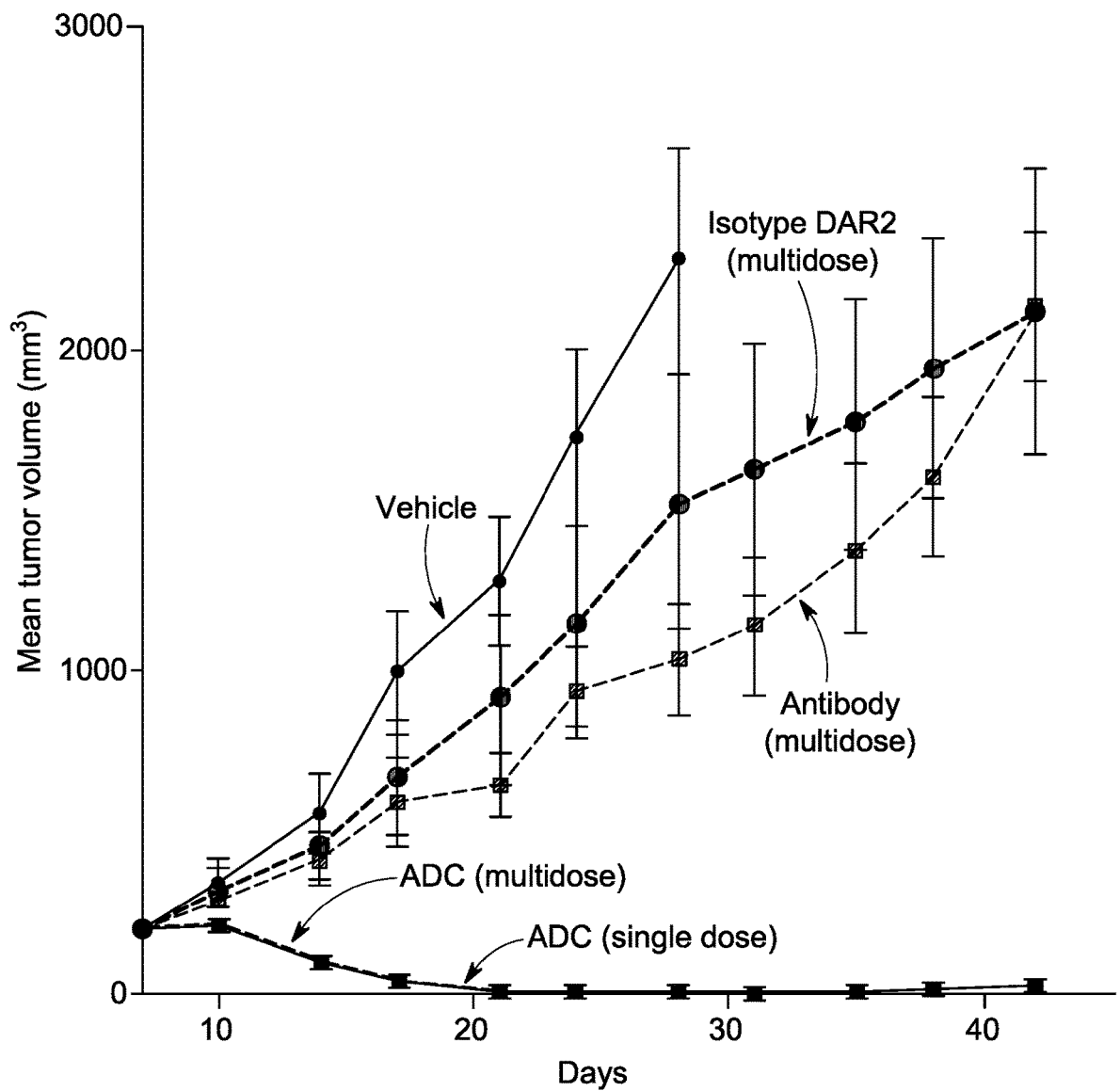
FIG. 11 shows data demonstrating the in vivo efficacy of the aldehyde-tagged anti-CD25 antibody conjugated at the heavy chain C-terminus to a maytansine payload attached to a HIPS-4AP linker in a Karpas 299 xenograft model, according to embodiments of the present disclosure.

The median time to endpoint for animals in the vehicle control groups was 28 days. At that point, none of the animals that had been dosed with the anti-CD25 HIPS-4AP-maytansine conjugate had detectable tumors. Data is shown in FIG. 11.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate of formula (I):

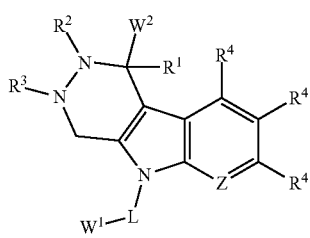

(I)

wherein
- Z is $CR^4$ or N;
- $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
- $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
- each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
- L is a linker comprising $(T^1-V^1)_a-(T^2-V^2)_b-(T^3-V^3)_c$, wherein a, b, and c are 1;
- $T^1$, is selected from $(C_1-C_{12})$alkyl and substituted $(C_1-C_{12})$alkyl;
- $T^2$ is 4-amino-piperidine (4AP) having the structure:

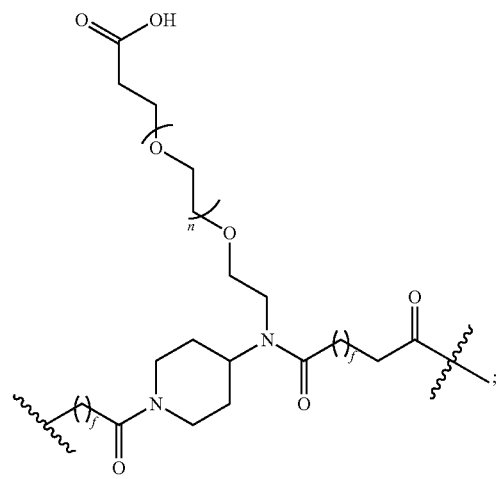

- $T^3$ is selected from $(C_1-C_{12})$alkyl and substituted $(C_1-C_{12})$alkyl;
- $V^1$, $V^2$, and $V^3$ are each —CO—;
- each f is independently an integer from 0 to 12;
- each n is independently an integer from 0 to 30;
- $W^1$ is a maytansinoid;
- $W^2$ is an anti-CD25 antibody comprising a heavy chain comprising complementarity determining regions (CDRs) of SYRMH (SEQ ID NO: 6), YINP- STGYTEYNQKFKD (SEQ ID NO: 7) and GGGVFDY (SEQ ID NO: 8); and a light chain comprising the CDRs of SASSSISYMH (SEQ ID NO: 9), YTSILHS (SEQ ID NO: 10), and QQGNTLPWT (SEQ ID NO: 11);

and wherein the anti-CD25 antibody comprises at the C-terminus of the heavy chain constant region a sequence of formula (II):

$$X^1(FGly')X^2Z^{20}X^3Z^{30} \quad (II)$$

wherein FGly' is the amino acid residue coupled to the linker;

$Z^{20}$ is either a proline or alanine residue;

$Z^{30}$ is a basic amino acid or an aliphatic amino acid;

X may be present or absent and, when present, can be any amino acid;

$X^2$ and $X^3$ are each independently any amino acid.

2. The conjugate of claim 1, wherein the maytansinoid is of the formula:

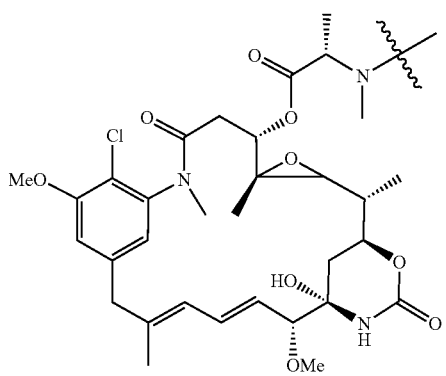

where ∼ indicates the point of attachment between the maytansinoid and L.

3. The conjugate of claim 1, wherein
$T^1$ is $(C_1-C_{12})$alkyl, and $T^3$ is $(C_1-C_{12})$alkyl.

4. The conjugate of claim 1,
wherein each f is independently and integer from 1 to 12; and
N is an integer from 1 to 30.

5. The conjugate of claim 1, wherein the anti-CD25 antibody is an IgG1 antibody.

6. The conjugate of claim 4, wherein the anti-CD25 antibody is an IgG1 kappa antibody.

7. The conjugate of claim 1, wherein the sequence of formula (II) is L(FGly')TPSR (SEQ ID NO: 144).

8. The conjugate of claim 1, wherein
Z30 is selected from R, K, H, A, G, L, V, I and P;
X1 is selected from L, M, S and V; and
X2 and X3 are each independently selected from S, T, A, V, G and C.

9. The conjugate of claim 1, wherein
the formula (II) sequence is C-terminal to the amino acid sequence SLSLSPG (SEQ ID NO: 145).

10. The conjugate of claim 9, wherein the heavy chain constant region comprises the sequence SPGSL(FGly')TPSRGS (SEQ ID NO: 149).

11. The conjugate of claim 9, wherein
$Z^{30}$ is selected from R, K, H, A, G, L, V, I, and P;
$X^1$ is selected from L, M, S, and V; and
$X^2$ and $X^3$ are each independently selected from S, T, A, V, G, and C.

12. The conjugate of claim 1, wherein the anti-CD25 antibody is daclizumab.

13. A pharmaceutical composition comprising:
a conjugate of claim 1; and
a pharmaceutically-acceptable excipient.

14. A method of treating a subject for a hematological cancer, wherein the hematological cancer comprises cells expressing CD25, the method comprising:
administering to the subject a therapeutically effective amount of a pharmaceutical composition comprising a conjugate of claim 1, wherein the administering is effective to treat the subject for the hematological cancer.

15. The method according to claim 14, wherein the hematologic cancer is leukemia.

16. The method according to claim 15, wherein the leukemia is acute myeloid leukemia (AML).

17. The method according to claim 16, wherein the AML is refractory AML.

18. The method according to claim 14, wherein the hematologic cancer is lymphoma.

19. The method according to claim 18, wherein the lymphoma is Hodgkin lymphoma (HL).

20. The method according to claim 18, wherein the lymphoma is Non-Hodgkin lymphoma (NHL).

21. The method of claim 14, wherein the anti-CD25 antibody of the conjugate is daclizumab.

22. A method of reducing inhibitory signals derived from T regulatory cells in a subject, the method comprising:
administering to the subject a therapeutically effective amount of a pharmaceutical composition comprising a conjugate of claim 1, wherein the administering is effective to reduce inhibitory signals derived from T regulatory cells in the subject.

* * * * *

SEQUENCE LISTING

<160> NUMBER OF SEQ ID NOS: 174

<210> SEQ ID NO 1
<211> LENGTH: 251
<212> TYPE: PRT
<213> ORGANISM: Homo sapiens

<400> SEQUENCE: 1

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

```
Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 2
<211> LENGTH: 213
<212> TYPE: PRT
<213> ORGANISM: Artificial sequence
<220> FEATURE:
<223> OTHER INFORMATION: synthetic sequence

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 3
<211> LENGTH: 454
<212> TYPE: PRT
<213> ORGANISM: Artificial sequence
<220> FEATURE:
<223> OTHER INFORMATION: synthetic sequence

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Ser Leu Cys
        435                 440                 445

Thr Pro Ser Arg Gly Ser
    450

<210> SEQ ID NO 4
<211> LENGTH: 645
<212> TYPE: DNA
<213> ORGANISM: Artificial sequence
<220> FEATURE:
<223> OTHER INFORMATION: synthetic sequence

<400> SEQUENCE: 4
gacatccaga tgacccagtc tccttccacc ctgtctgcat ctgtaggaga cagagtcacc      60
atcacttgca gcgccagcag cagtattagt tacatgcact ggtatcagca gaaaccaggg    120
aaagccccta agctcctgat ctataccacc tccaacttgg ccagtggggt cccagccagg    180
ttcagcggca gtggatctgg gacagaattc actctcacca tcagcagcct gcagcctgat    240
gattttgcaa cttattactg ccaccagagg agcacctatc cctgactttt cggccagggg    300
accaaggtgg aggtgaaacg tactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt agtga                   645

<210> SEQ ID NO 5
<211> LENGTH: 1368
<212> TYPE: DNA
<213> ORGANISM: Artificial sequence
<220> FEATURE:
<223> OTHER INFORMATION: synthetic sequence

<400> SEQUENCE: 5
caggtgcagc tggtgcagtc tggggctgag gtgaagaagc ctgggagctc agtgaaggtt      60
tcctgcaagg catctggata caccttcacc agctacagga tgcactgggt gcgacaggcc    120
cctggacaag gcttgagtg gatcggatac atcaaccctca gtaccggtta cacagagtac    180
aaccagaagt tcaaggacaa ggccaccatc accgccgacg agtccacgaa cacagcctac    240
atggagctga gcagcctgag atctgaggac acggccgtgt attactgtgc gagaggcgga    300
ggagtgttcg actactgggg ccagggaacc ctggtgaccg tctcctcagc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600

-continued

```
gtgaatcaca agcccagcaa caccaaggtg gacaagagag ttgagcccaa atcttgtgac    660
aaaactcaca catgcccacc gtgcccagca cctgaactcc tggggggacc gtcagtcttc    720
ctcttccccc caaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagcca gagaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaagggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc ccgggtcctt atgtaccct tctagaggat cctgatga              1368
```

<210> SEQ ID NO 6
<211> LENGTH: 5
<212> TYPE: PRT
<213> ORGANISM: Artificial sequence
<220> FEATURE:
<223> OTHER INFORMATION: synthetic sequence

<400> SEQUENCE: 6

Ser Tyr Arg Met His
1               5

<210> SEQ ID NO 7
<211> LENGTH: 17
<212> TYPE: PRT
<213> ORGANISM: Artificial sequence
<220> FEATURE:
<223> OTHER INFORMATION: synthetic sequence

<400> SEQUENCE: 7

Tyr Ile Asn Pro Ser Thr Gly Tyr Thr Glu Tyr Asn Gln Lys Phe Lys
1               5                   10                  15
Asp

<210> SEQ ID NO 8
<211> LENGTH: 7
<212> TYPE: PRT
<213> ORGANISM: Artificial sequence
<220> FEATURE:
<223> OTHER INFORMATION: synthetic sequence

<400> SEQUENCE: 8

Gly Gly Gly Val Phe Asp Tyr
1               5

<210> SEQ ID NO 9
<211> LENGTH: 10
<212> TYPE: PRT
<213> ORGANISM: Artificial sequence
<220> FEATURE:
<223> OTHER INFORMATION: synthetic sequence

<400> SEQUENCE: 9

Ser Ala Ser Ser Ser Ile Ser Tyr Met His

```
<210> SEQ ID NO 10
<211> LENGTH: 7
<212> TYPE: PRT
<213> ORGANISM: Artificial sequence
<220> FEATURE:
<223> OTHER INFORMATION: synthetic sequence

<400> SEQUENCE: 10

Tyr Thr Ser Ile Leu His Ser
1               5

<210> SEQ ID NO 11
<211> LENGTH: 9
<212> TYPE: PRT
<213> ORGANISM: Artificial sequence
<220> FEATURE:
<223> OTHER INFORMATION: synthetic sequence

<400> SEQUENCE: 11

Gln Gln Gly Asn Thr Leu Pro Trp Thr
1               5

<210> SEQ ID NO 12
<211> LENGTH: 116
<212> TYPE: PRT
<213> ORGANISM: Artificial sequence
<220> FEATURE:
<223> OTHER INFORMATION: synthetic sequence

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Ile
            35                  40                  45

Gly Tyr Ile Asn Pro Ser Thr Gly Tyr Thr Glu Tyr Asn Gln Lys Phe
        50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 13
<211> LENGTH: 106
<212> TYPE: PRT
<213> ORGANISM: Artificial sequence
<220> FEATURE:
<223> OTHER INFORMATION: synthetic sequence

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
```

```
                35                  40                  45
Thr Thr Ser Asn Leu Ala Ser Gly Val Pro Ala Arg Phe Ser Gly Ser
            50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys His Gln Arg Ser Thr Tyr Pro Leu Thr
                85                  90                  95
Phe Gly Gln Gly Thr Lys Val Glu Val Lys
            100                 105
```

<210> SEQ ID NO 14

<400> SEQUENCE: 14

000

<210> SEQ ID NO 15

<400> SEQUENCE: 15

000

<210> SEQ ID NO 16
<211> LENGTH: 6
<212> TYPE: PRT
<213> ORGANISM: Artificial sequence
<220> FEATURE:
<223> OTHER INFORMATION: synthetic sequence

<400> SEQUENCE: 16

```
Leu Cys Thr Pro Ser Arg
1               5
```

<210> SEQ ID NO 17
<211> LENGTH: 6
<212> TYPE: PRT
<213> ORGANISM: Artificial sequence
<220> FEATURE:
<223> OTHER INFORMATION: synthetic sequence

<400> SEQUENCE: 17

```
Met Cys Thr Pro Ser Arg
1               5
```

<210> SEQ ID NO 18
<211> LENGTH: 6
<212> TYPE: PRT
<213> ORGANISM: Artificial sequence
<220> FEATURE:
<223> OTHER INFORMATION: synthetic sequence

<400> SEQUENCE: 18

```
Val Cys Thr Pro Ser Arg
1               5
```

<210> SEQ ID NO 19
<211> LENGTH: 6
<212> TYPE: PRT
<213> ORGANISM: Artificial sequence
<220> FEATURE:
<223> OTHER INFORMATION: synthetic sequence

<400> SEQUENCE: 19

```
Leu Cys Ser Pro Ser Arg
1               5
```

```
<210> SEQ ID NO 20
<211> LENGTH: 6
<212> TYPE: PRT
<213> ORGANISM: Artificial sequence
<220> FEATURE:
<223> OTHER INFORMATION: synthetic sequence

<400> SEQUENCE: 20

Leu Cys Ala Pro Ser Arg
1               5

<210> SEQ ID NO 21
<211> LENGTH: 6
<212> TYPE: PRT
<213> ORGANISM: Artificial sequence
<220> FEATURE:
<223> OTHER INFORMATION: synthetic sequence

<400> SEQUENCE: 21

Leu Cys Val Pro Ser Arg
1               5

<210> SEQ ID NO 22
<211> LENGTH: 6
<212> TYPE: PRT
<213> ORGANISM: Artificial sequence
<220> FEATURE:
<223> OTHER INFORMATION: synthetic sequence

<400> SEQUENCE: 22

Leu Cys Gly Pro Ser Arg
1               5

<210> SEQ ID NO 23
<211> LENGTH: 6
<212> TYPE: PRT
<213> ORGANISM: Artificial sequence
<220> FEATURE:
<223> OTHER INFORMATION: synthetic sequence

<400> SEQUENCE: 23

Ile Cys Thr Pro Ala Arg
1               5

<210> SEQ ID NO 24
<211> LENGTH: 6
<212> TYPE: PRT
<213> ORGANISM: Artificial sequence
<220> FEATURE:
<223> OTHER INFORMATION: synthetic sequence

<400> SEQUENCE: 24

Leu Cys Thr Pro Ser Lys
1               5

<210> SEQ ID NO 25
<211> LENGTH: 6
<212> TYPE: PRT
<213> ORGANISM: Artificial sequence
<220> FEATURE:
<223> OTHER INFORMATION: synthetic sequence

<400> SEQUENCE: 25

Met Cys Thr Pro Ser Lys
1               5
```

```
<210> SEQ ID NO 26
<211> LENGTH: 6
<212> TYPE: PRT
<213> ORGANISM: Artificial sequence
<220> FEATURE:
<223> OTHER INFORMATION: synthetic sequence

<400> SEQUENCE: 26

Val Cys Thr Pro Ser Lys
1               5

<210> SEQ ID NO 27
<211> LENGTH: 6
<212> TYPE: PRT
<213> ORGANISM: Artificial sequence
<220> FEATURE:
<223> OTHER INFORMATION: synthetic sequence

<400> SEQUENCE: 27

Leu Cys Ser Pro Ser Lys
1               5

<210> SEQ ID NO 28
<211> LENGTH: 6
<212> TYPE: PRT
<213> ORGANISM: Artificial sequence
<220> FEATURE:
<223> OTHER INFORMATION: synthetic sequence

<400> SEQUENCE: 28

Leu Cys Ala Pro Ser Lys
1               5

<210> SEQ ID NO 29
<211> LENGTH: 6
<212> TYPE: PRT
<213> ORGANISM: Artificial sequence
<220> FEATURE:
<223> OTHER INFORMATION: synthetic sequence

<400> SEQUENCE: 29

Leu Cys Val Pro Ser Lys
1               5

<210> SEQ ID NO 30
<211> LENGTH: 6
<212> TYPE: PRT
<213> ORGANISM: Artificial sequence
<220> FEATURE:
<223> OTHER INFORMATION: synthetic sequence

<400> SEQUENCE: 30

Leu Cys Gly Pro Ser Lys
1               5

<210> SEQ ID NO 31
<211> LENGTH: 6
<212> TYPE: PRT
<213> ORGANISM: Artificial sequence
<220> FEATURE:
<223> OTHER INFORMATION: synthetic sequence

<400> SEQUENCE: 31

Leu Cys Thr Pro Ser Ala
1               5
```

```
<210> SEQ ID NO 32
<211> LENGTH: 6
<212> TYPE: PRT
<213> ORGANISM: Artificial sequence
<220> FEATURE:
<223> OTHER INFORMATION: synthetic sequence

<400> SEQUENCE: 32

Ile Cys Thr Pro Ala Ala
1               5

<210> SEQ ID NO 33
<211> LENGTH: 6
<212> TYPE: PRT
<213> ORGANISM: Artificial sequence
<220> FEATURE:
<223> OTHER INFORMATION: synthetic sequence

<400> SEQUENCE: 33

Met Cys Thr Pro Ser Ala
1               5

<210> SEQ ID NO 34
<211> LENGTH: 6
<212> TYPE: PRT
<213> ORGANISM: Artificial sequence
<220> FEATURE:
<223> OTHER INFORMATION: synthetic sequence

<400> SEQUENCE: 34

Val Cys Thr Pro Ser Ala
1               5

<210> SEQ ID NO 35
<211> LENGTH: 6
<212> TYPE: PRT
<213> ORGANISM: Artificial sequence
<220> FEATURE:
<223> OTHER INFORMATION: synthetic sequence

<400> SEQUENCE: 35

Leu Cys Ser Pro Ser Ala
1               5

<210> SEQ ID NO 36
<211> LENGTH: 6
<212> TYPE: PRT
<213> ORGANISM: Artificial sequence
<220> FEATURE:
<223> OTHER INFORMATION: synthetic sequence

<400> SEQUENCE: 36

Leu Cys Ala Pro Ser Ala
1               5

<210> SEQ ID NO 37
<211> LENGTH: 6
<212> TYPE: PRT
<213> ORGANISM: Artificial sequence
<220> FEATURE:
<223> OTHER INFORMATION: synthetic sequence

<400> SEQUENCE: 37

Leu Cys Val Pro Ser Ala
1               5

<210> SEQ ID NO 38
```

```
<211> LENGTH: 6
<212> TYPE: PRT
<213> ORGANISM: Artificial sequence
<220> FEATURE:
<223> OTHER INFORMATION: synthetic sequence

<400> SEQUENCE: 38

Leu Cys Gly Pro Ser Ala
1               5

<210> SEQ ID NO 39
<211> LENGTH: 12
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (6)..(6)
<223> OTHER INFORMATION: FORMYLATION

<400> SEQUENCE: 39

Ser Pro Gly Ser Leu Gly Thr Pro Ser Arg Gly Ser
1               5                   10

<210> SEQ ID NO 40
<211> LENGTH: 8
<212> TYPE: PRT
<213> ORGANISM: Artificial sequence
<220> FEATURE:
<223> OTHER INFORMATION: synthetic sequence

<400> SEQUENCE: 40

Ser Leu Ser Leu Ser Pro Gly Lys
1               5

<210> SEQ ID NO 41

<400> SEQUENCE: 41

000

<210> SEQ ID NO 42
<211> LENGTH: 6
<212> TYPE: PRT
<213> ORGANISM: Artificial sequence
<220> FEATURE:
<223> OTHER INFORMATION: synthetic sequence

<400> SEQUENCE: 42

Lys Val Asp Asn Ala Leu
1               5

<210> SEQ ID NO 43
<211> LENGTH: 6
<212> TYPE: PRT
<213> ORGANISM: Artificial sequence
<220> FEATURE:
<223> OTHER INFORMATION: synthetic sequence

<400> SEQUENCE: 43

Gln Ser Gly Asn Ser Gln
1               5

<210> SEQ ID NO 44
<211> LENGTH: 17
<212> TYPE: PRT
<213> ORGANISM: Artificial sequence
```

```
<220> FEATURE:
<223> OTHER INFORMATION: synthetic sequence
<220> FEATURE:
<221> NAME/KEY: MOD_RES
<222> LOCATION: (7)..(7)
<223> OTHER INFORMATION: FORMYLATION

<400> SEQUENCE: 44

Lys Val Asp Asn Ala Leu Gly Thr Pro Ser Arg Gln Ser Gly Asn Ser
1               5                   10                  15

Gln

<210> SEQ ID NO 45

<400> SEQUENCE: 45

000

<210> SEQ ID NO 46
<211> LENGTH: 6
<212> TYPE: PRT
<213> ORGANISM: Artificial sequence
<220> FEATURE:
<223> OTHER INFORMATION: synthetic sequence

<400> SEQUENCE: 46

Ser Trp Asn Ser Gly Ala
1               5

<210> SEQ ID NO 47
<211> LENGTH: 6
<212> TYPE: PRT
<213> ORGANISM: Artificial sequence
<220> FEATURE:
<223> OTHER INFORMATION: synthetic sequence

<400> SEQUENCE: 47

Gly Val His Thr Phe Pro
1               5

<210> SEQ ID NO 48
<211> LENGTH: 18
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (8)..(8)
<223> OTHER INFORMATION: FORMYLATION

<400> SEQUENCE: 48

Ser Trp Asn Ser Gly Ala Leu Gly Thr Pro Ser Arg Gly Val His Thr
1               5                   10                  15

Phe Pro

<210> SEQ ID NO 49
<211> LENGTH: 6
<212> TYPE: PRT
<213> ORGANISM: Homo sapiens

<400> SEQUENCE: 49

Ala Ser Thr Lys Gly Pro
1               5

<210> SEQ ID NO 50
```

```
<211> LENGTH: 7
<212> TYPE: PRT
<213> ORGANISM: Homo sapiens

<400> SEQUENCE: 50

Lys Ser Thr Ser Gly Gly Thr
1               5

<210> SEQ ID NO 51
<211> LENGTH: 4
<212> TYPE: PRT
<213> ORGANISM: Homo sapiens

<400> SEQUENCE: 51

Pro Glu Pro Val
1

<210> SEQ ID NO 52
<211> LENGTH: 8
<212> TYPE: PRT
<213> ORGANISM: Homo sapiens

<400> SEQUENCE: 52

Asn Ser Gly Ala Leu Thr Ser Gly
1               5

<210> SEQ ID NO 53
<211> LENGTH: 21
<212> TYPE: PRT
<213> ORGANISM: Homo sapiens

<400> SEQUENCE: 53

Asn Ser Gly Ala Leu Thr Ser Gly Val His Thr Phe Pro Ala Val Leu
1               5                   10                  15

Gln Ser Ser Gly Leu
            20

<210> SEQ ID NO 54
<211> LENGTH: 5
<212> TYPE: PRT
<213> ORGANISM: Homo sapiens

<400> SEQUENCE: 54

Gln Ser Ser Gly Leu
1               5

<210> SEQ ID NO 55
<211> LENGTH: 4
<212> TYPE: PRT
<213> ORGANISM: Homo sapiens

<400> SEQUENCE: 55

Thr Gln Thr Tyr
1

<210> SEQ ID NO 56
<211> LENGTH: 5
<212> TYPE: PRT
<213> ORGANISM: Homo sapiens

<400> SEQUENCE: 56

His Lys Pro Ser Asn
1               5
```

```
<210> SEQ ID NO 57
<211> LENGTH: 22
<212> TYPE: PRT
<213> ORGANISM: Homo sapiens

<400> SEQUENCE: 57

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 58
<211> LENGTH: 5
<212> TYPE: PRT
<213> ORGANISM: Homo sapiens

<400> SEQUENCE: 58

Phe Pro Pro Lys Pro
1               5

<210> SEQ ID NO 59
<211> LENGTH: 5
<212> TYPE: PRT
<213> ORGANISM: Homo sapiens

<400> SEQUENCE: 59

Ile Ser Arg Thr Pro
1               5

<210> SEQ ID NO 60
<211> LENGTH: 9
<212> TYPE: PRT
<213> ORGANISM: Homo sapiens

<400> SEQUENCE: 60

Asp Val Ser His Glu Asp Pro Glu Val
1               5

<210> SEQ ID NO 61
<211> LENGTH: 7
<212> TYPE: PRT
<213> ORGANISM: Homo sapiens

<400> SEQUENCE: 61

Ser His Glu Asp Pro Glu Val
1               5

<210> SEQ ID NO 62
<211> LENGTH: 9
<212> TYPE: PRT
<213> ORGANISM: Homo sapiens

<400> SEQUENCE: 62

Asp Gly Val Glu Val His Asn Ala Lys
1               5

<210> SEQ ID NO 63
<211> LENGTH: 5
<212> TYPE: PRT
<213> ORGANISM: Homo sapiens

<400> SEQUENCE: 63

Gln Tyr Asn Ser Thr
1               5
```

```
<210> SEQ ID NO 64
<211> LENGTH: 5
<212> TYPE: PRT
<213> ORGANISM: Homo sapiens

<400> SEQUENCE: 64

Val Leu Thr Val Leu
1               5

<210> SEQ ID NO 65
<211> LENGTH: 7
<212> TYPE: PRT
<213> ORGANISM: Homo sapiens

<400> SEQUENCE: 65

Asn Lys Ala Leu Pro Ala Pro
1               5

<210> SEQ ID NO 66
<211> LENGTH: 9
<212> TYPE: PRT
<213> ORGANISM: Homo sapiens

<400> SEQUENCE: 66

Ser Lys Ala Lys Gly Gln Pro Arg Glu
1               5

<210> SEQ ID NO 67
<211> LENGTH: 7
<212> TYPE: PRT
<213> ORGANISM: Homo sapiens

<400> SEQUENCE: 67

Lys Ala Lys Gly Gln Pro Arg
1               5

<210> SEQ ID NO 68
<211> LENGTH: 10
<212> TYPE: PRT
<213> ORGANISM: Homo sapiens

<400> SEQUENCE: 68

Pro Pro Ser Arg Lys Glu Leu Thr Lys Asn
1               5                   10

<210> SEQ ID NO 69
<211> LENGTH: 5
<212> TYPE: PRT
<213> ORGANISM: Homo sapiens

<400> SEQUENCE: 69

Tyr Pro Ser Asp Ile
1               5

<210> SEQ ID NO 70
<211> LENGTH: 7
<212> TYPE: PRT
<213> ORGANISM: Homo sapiens

<400> SEQUENCE: 70

Asn Gly Gln Pro Glu Asn Asn
1               5

<210> SEQ ID NO 71
```

```
<211> LENGTH: 10
<212> TYPE: PRT
<213> ORGANISM: Homo sapiens

<400> SEQUENCE: 71

Thr Pro Pro Val Leu Asp Ser Asp Gly Ser
1               5                   10

<210> SEQ ID NO 72
<211> LENGTH: 19
<212> TYPE: PRT
<213> ORGANISM: Homo sapiens

<400> SEQUENCE: 72

His Glu Ala Leu His Asn His Tyr Thr Gln Lys Ser Leu Ser Leu Ser
1               5                   10                  15

Pro Gly Lys

<210> SEQ ID NO 73
<211> LENGTH: 6
<212> TYPE: PRT
<213> ORGANISM: Homo sapiens

<400> SEQUENCE: 73

Ser Leu Ser Pro Gly Lys
1               5

<210> SEQ ID NO 74
<211> LENGTH: 12
<212> TYPE: PRT
<213> ORGANISM: Homo sapiens

<400> SEQUENCE: 74

Pro Cys Ser Arg Ser Thr Ser Glu Ser Thr Ala Ala
1               5                   10

<210> SEQ ID NO 75
<211> LENGTH: 5
<212> TYPE: PRT
<213> ORGANISM: Homo sapiens

<400> SEQUENCE: 75

Phe Pro Glu Pro Val
1               5

<210> SEQ ID NO 76
<211> LENGTH: 12
<212> TYPE: PRT
<213> ORGANISM: Homo sapiens

<400> SEQUENCE: 76

Ser Gly Ala Leu Thr Ser Gly Val His Thr Phe Pro
1               5                   10

<210> SEQ ID NO 77
<211> LENGTH: 6
<212> TYPE: PRT
<213> ORGANISM: Homo sapiens

<400> SEQUENCE: 77

Gln Ser Ser Gly Leu Tyr
1               5

<210> SEQ ID NO 78
```

```
<211> LENGTH: 5
<212> TYPE: PRT
<213> ORGANISM: Homo sapiens

<400> SEQUENCE: 78

Val Ala Gly Pro Ser
1               5

<210> SEQ ID NO 79
<211> LENGTH: 5
<212> TYPE: PRT
<213> ORGANISM: Homo sapiens

<400> SEQUENCE: 79

Val Leu Thr Val Val
1               5

<210> SEQ ID NO 80
<211> LENGTH: 7
<212> TYPE: PRT
<213> ORGANISM: Homo sapiens

<400> SEQUENCE: 80

Asn Lys Gly Leu Pro Ala Pro
1               5

<210> SEQ ID NO 81
<211> LENGTH: 9
<212> TYPE: PRT
<213> ORGANISM: Homo sapiens

<400> SEQUENCE: 81

Ser Lys Thr Lys Gly Gln Pro Arg Glu
1               5

<210> SEQ ID NO 82
<211> LENGTH: 5
<212> TYPE: PRT
<213> ORGANISM: Homo sapiens

<400> SEQUENCE: 82

Met Thr Lys Asn Gln
1               5

<210> SEQ ID NO 83

<400> SEQUENCE: 83

000

<210> SEQ ID NO 84
<211> LENGTH: 10
<212> TYPE: PRT
<213> ORGANISM: Homo sapiens

<400> SEQUENCE: 84

Thr Pro Pro Met Leu Asp Ser Asp Gly Ser
1               5                   10

<210> SEQ ID NO 85
<211> LENGTH: 4
<212> TYPE: PRT
<213> ORGANISM: Homo sapiens

<400> SEQUENCE: 85
```

```
Gly Asn Val Phe
1

<210> SEQ ID NO 86

<400> SEQUENCE: 86

000

<210> SEQ ID NO 87
<211> LENGTH: 10
<212> TYPE: PRT
<213> ORGANISM: Homo sapiens

<400> SEQUENCE: 87

Pro Cys Ser Arg Ser Thr Ser Gly Gly Thr
1               5                   10

<210> SEQ ID NO 88
<211> LENGTH: 19
<212> TYPE: PRT
<213> ORGANISM: Homo sapiens

<400> SEQUENCE: 88

Ser Gly Ala Leu Thr Ser Gly Val His Thr Phe Pro Ala Val Leu Gln
1               5                   10                  15

Ser Ser Gly

<210> SEQ ID NO 89
<211> LENGTH: 10
<212> TYPE: PRT
<213> ORGANISM: Homo sapiens

<400> SEQUENCE: 89

Arg Val Glu Leu Lys Thr Pro Leu Gly Asp
1               5                   10

<210> SEQ ID NO 90
<211> LENGTH: 7
<212> TYPE: PRT
<213> ORGANISM: Homo sapiens

<400> SEQUENCE: 90

Cys Pro Arg Cys Pro Lys Pro
1               5

<210> SEQ ID NO 91
<211> LENGTH: 21
<212> TYPE: PRT
<213> ORGANISM: Homo sapiens

<400> SEQUENCE: 91

Pro Lys Ser Cys Asp Thr Pro Pro Pro Cys Pro Arg Cys Pro Ala Pro
1               5                   10                  15

Glu Leu Leu Gly Gly
            20

<210> SEQ ID NO 92
<211> LENGTH: 10
<212> TYPE: PRT
<213> ORGANISM: Homo sapiens

<400> SEQUENCE: 92

Pro Pro Ser Arg Glu Glu Met Thr Lys Asn
```

<210> SEQ ID NO 93
<211> LENGTH: 8
<212> TYPE: PRT
<213> ORGANISM: Homo sapiens

<400> SEQUENCE: 93

Ser Ser Gly Gln Pro Glu Asn Asn
1               5

<210> SEQ ID NO 94

<400> SEQUENCE: 94

000

<210> SEQ ID NO 95
<211> LENGTH: 7
<212> TYPE: PRT
<213> ORGANISM: Homo sapiens

<400> SEQUENCE: 95

His Glu Ala Leu His Asn Arg
1               5

<210> SEQ ID NO 96
<211> LENGTH: 5
<212> TYPE: PRT
<213> ORGANISM: Homo sapiens

<400> SEQUENCE: 96

Ser Thr Lys Gly Pro
1               5

<210> SEQ ID NO 97
<211> LENGTH: 11
<212> TYPE: PRT
<213> ORGANISM: Homo sapiens

<400> SEQUENCE: 97

Cys Pro Ala Pro Glu Phe Leu Gly Gly Pro Ser
1               5                   10

<210> SEQ ID NO 98
<211> LENGTH: 9
<212> TYPE: PRT
<213> ORGANISM: Homo sapiens

<400> SEQUENCE: 98

Asp Val Ser Gln Glu Asp Pro Glu Val
1               5

<210> SEQ ID NO 99
<211> LENGTH: 7
<212> TYPE: PRT
<213> ORGANISM: Homo sapiens

<400> SEQUENCE: 99

Asn Lys Gly Leu Pro Ser Ser
1               5

<210> SEQ ID NO 100
<211> LENGTH: 10
<212> TYPE: PRT

```
<213> ORGANISM: Homo sapiens

<400> SEQUENCE: 100

Ser Lys Ala Lys Gly Gln Pro Arg Glu Pro
1               5                   10

<210> SEQ ID NO 101
<211> LENGTH: 10
<212> TYPE: PRT
<213> ORGANISM: Homo sapiens

<400> SEQUENCE: 101

Pro Pro Ser Gln Glu Glu Met Thr Lys Asn
1               5                   10

<210> SEQ ID NO 102
<211> LENGTH: 19
<212> TYPE: PRT
<213> ORGANISM: Homo sapiens

<400> SEQUENCE: 102

His Glu Ala Leu His Asn His Tyr Thr Gln Lys Ser Leu Ser Leu Ser
1               5                   10                  15

Leu Gly Lys

<210> SEQ ID NO 103
<211> LENGTH: 13
<212> TYPE: PRT
<213> ORGANISM: Homo sapiens

<400> SEQUENCE: 103

Ala Ser Pro Thr Ser Pro Lys Val Phe Pro Leu Ser Leu
1               5                   10

<210> SEQ ID NO 104
<211> LENGTH: 5
<212> TYPE: PRT
<213> ORGANISM: Homo sapiens

<400> SEQUENCE: 104

Gln Pro Asp Gly Asn
1               5

<210> SEQ ID NO 105
<211> LENGTH: 10
<212> TYPE: PRT
<213> ORGANISM: Homo sapiens

<400> SEQUENCE: 105

Val Gln Gly Phe Phe Pro Gln Glu Pro Leu
1               5                   10

<210> SEQ ID NO 106
<211> LENGTH: 11
<212> TYPE: PRT
<213> ORGANISM: Homo sapiens

<400> SEQUENCE: 106

Ser Gly Gln Gly Val Thr Ala Arg Asn Phe Pro
1               5                   10

<210> SEQ ID NO 107
<211> LENGTH: 7
<212> TYPE: PRT
```

<213> ORGANISM: Homo sapiens

<400> SEQUENCE: 107

Ser Gly Asp Leu Tyr Thr Thr
1               5

<210> SEQ ID NO 108
<211> LENGTH: 4
<212> TYPE: PRT
<213> ORGANISM: Homo sapiens

<400> SEQUENCE: 108

Pro Ala Thr Gln
1

<210> SEQ ID NO 109
<211> LENGTH: 4
<212> TYPE: PRT
<213> ORGANISM: Homo sapiens

<400> SEQUENCE: 109

His Arg Pro Ala
1

<210> SEQ ID NO 110
<211> LENGTH: 5
<212> TYPE: PRT
<213> ORGANISM: Homo sapiens

<400> SEQUENCE: 110

Leu Leu Gly Ser Glu
1               5

<210> SEQ ID NO 111
<211> LENGTH: 8
<212> TYPE: PRT
<213> ORGANISM: Homo sapiens

<400> SEQUENCE: 111

Gly Leu Arg Asp Ala Ser Gly Val
1               5

<210> SEQ ID NO 112
<211> LENGTH: 10
<212> TYPE: PRT
<213> ORGANISM: Homo sapiens

<400> SEQUENCE: 112

Ser Ser Gly Lys Ser Ala Val Gln Gly Pro
1               5                   10

<210> SEQ ID NO 113
<211> LENGTH: 4
<212> TYPE: PRT
<213> ORGANISM: Homo sapiens

<400> SEQUENCE: 113

Gly Cys Tyr Ser
1

<210> SEQ ID NO 114
<211> LENGTH: 4
<212> TYPE: PRT
<213> ORGANISM: Homo sapiens

<400> SEQUENCE: 114

Cys Ala Glu Pro
1

<210> SEQ ID NO 115
<211> LENGTH: 24
<212> TYPE: PRT
<213> ORGANISM: Homo sapiens

<400> SEQUENCE: 115

Ser Gly Asn Thr Phe Arg Pro Glu Val His Leu Leu Pro Pro Pro Ser
1               5                   10                  15

Glu Glu Leu Ala Leu Asn Glu Leu
            20

<210> SEQ ID NO 116
<211> LENGTH: 5
<212> TYPE: PRT
<213> ORGANISM: Homo sapiens

<400> SEQUENCE: 116

Ala Arg Gly Phe Ser
1               5

<210> SEQ ID NO 117
<211> LENGTH: 11
<212> TYPE: PRT
<213> ORGANISM: Homo sapiens

<400> SEQUENCE: 117

Gln Gly Ser Gln Glu Leu Pro Arg Glu Lys Tyr
1               5                   10

<210> SEQ ID NO 118
<211> LENGTH: 4
<212> TYPE: PRT
<213> ORGANISM: Homo sapiens

<400> SEQUENCE: 118

Ala Ala Glu Asp
1

<210> SEQ ID NO 119
<211> LENGTH: 4
<212> TYPE: PRT
<213> ORGANISM: Homo sapiens

<400> SEQUENCE: 119

His Glu Ala Leu
1

<210> SEQ ID NO 120
<211> LENGTH: 25
<212> TYPE: PRT
<213> ORGANISM: Homo sapiens

<400> SEQUENCE: 120

Ile Asp Arg Leu Ala Gly Lys Pro Thr His Val Asn Val Ser Val Val
1               5                   10                  15

Met Ala Glu Val Asp Gly Thr Cys Tyr
            20                  25

<210> SEQ ID NO 121

<400> SEQUENCE: 121

000

<210> SEQ ID NO 122
<211> LENGTH: 11
<212> TYPE: PRT
<213> ORGANISM: Artificial sequence
<220> FEATURE:
<223> OTHER INFORMATION: synthetic sequence

<400> SEQUENCE: 122

Asn Ser Gly Ala Leu Cys Thr Pro Ser Arg Gly
1               5                   10

<210> SEQ ID NO 123
<211> LENGTH: 5
<212> TYPE: PRT
<213> ORGANISM: Artificial sequence
<220> FEATURE:
<223> OTHER INFORMATION: synthetic sequence

<400> SEQUENCE: 123

Cys Thr Pro Ser Arg
1               5

<210> SEQ ID NO 124

<400> SEQUENCE: 124

000

<210> SEQ ID NO 125
<211> LENGTH: 9
<212> TYPE: PRT
<213> ORGANISM: Artificial sequence
<220> FEATURE:
<223> OTHER INFORMATION: synthetic sequence

<400> SEQUENCE: 125

Asn Leu Cys Thr Pro Ser Arg Ala Pro
1               5

<210> SEQ ID NO 126
<211> LENGTH: 10
<212> TYPE: PRT
<213> ORGANISM: Artificial sequence
<220> FEATURE:
<223> OTHER INFORMATION: synthetic sequence

<400> SEQUENCE: 126

Lys Ala Lys Gly Leu Cys Thr Pro Ser Arg
1               5                   10

<210> SEQ ID NO 127
<211> LENGTH: 6
<212> TYPE: PRT
<213> ORGANISM: Homo sapiens

<400> SEQUENCE: 127

Arg Thr Val Ala Ala Pro
1               5

<210> SEQ ID NO 128
<211> LENGTH: 5
<212> TYPE: PRT

<213> ORGANISM: Homo sapiens

<400> SEQUENCE: 128

Tyr Pro Arg Glu Ala
1               5

<210> SEQ ID NO 129
<211> LENGTH: 4
<212> TYPE: PRT
<213> ORGANISM: Homo sapiens

<400> SEQUENCE: 129

Pro Arg Glu Ala
1

<210> SEQ ID NO 130
<211> LENGTH: 8
<212> TYPE: PRT
<213> ORGANISM: Homo sapiens

<400> SEQUENCE: 130

Asp Asn Ala Leu Gln Ser Gly Asn
1               5

<210> SEQ ID NO 131
<211> LENGTH: 9
<212> TYPE: PRT
<213> ORGANISM: Homo sapiens

<400> SEQUENCE: 131

Thr Glu Gln Asp Ser Lys Asp Ser Thr
1               5

<210> SEQ ID NO 132
<211> LENGTH: 6
<212> TYPE: PRT
<213> ORGANISM: Homo sapiens

<400> SEQUENCE: 132

His Gln Gly Leu Ser Ser
1               5

<210> SEQ ID NO 133
<211> LENGTH: 4
<212> TYPE: PRT
<213> ORGANISM: Homo sapiens

<400> SEQUENCE: 133

Arg Gly Glu Cys
1

<210> SEQ ID NO 134
<211> LENGTH: 6
<212> TYPE: PRT
<213> ORGANISM: Homo sapiens

<400> SEQUENCE: 134

Gln Pro Lys Ala Ala Pro
1               5

<210> SEQ ID NO 135
<211> LENGTH: 7
<212> TYPE: PRT
<213> ORGANISM: Homo sapiens

<400> SEQUENCE: 135

Asp Phe Tyr Pro Gly Ala Val
1               5

<210> SEQ ID NO 136
<211> LENGTH: 8
<212> TYPE: PRT
<213> ORGANISM: Homo sapiens

<400> SEQUENCE: 136

Asp Ser Ser Pro Val Lys Ala Gly
1               5

<210> SEQ ID NO 137
<211> LENGTH: 6
<212> TYPE: PRT
<213> ORGANISM: Homo sapiens

<400> SEQUENCE: 137

Ala Pro Thr Glu Cys Ser
1               5

<210> SEQ ID NO 138
<211> LENGTH: 99
<212> TYPE: PRT
<213> ORGANISM: Artificial sequence
<220> FEATURE:
<223> OTHER INFORMATION: synthetic sequence

<400> SEQUENCE: 138

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu

<210> SEQ ID NO 139
<211> LENGTH: 8
<212> TYPE: PRT
<213> ORGANISM: Artificial sequence
<220> FEATURE:
<223> OTHER INFORMATION: synthetic sequence

<400> SEQUENCE: 139

Gly Ala Leu Thr Ser Gly Val His
1               5

<210> SEQ ID NO 140
<211> LENGTH: 11
<212> TYPE: PRT
<213> ORGANISM: Artificial sequence
<220> FEATURE:
<223> OTHER INFORMATION: synthetic sequence

<400> SEQUENCE: 140

```
Gly Ala Leu Cys Thr Pro Ser Arg Gly Val His
1               5                   10
```

<210> SEQ ID NO 141
<211> LENGTH: 9
<212> TYPE: PRT
<213> ORGANISM: Artificial sequence
<220> FEATURE:
<223> OTHER INFORMATION: synthetic sequence

<400> SEQUENCE: 141

```
Ser Leu Cys Thr Pro Ser Arg Gly Ser
1               5
```

<210> SEQ ID NO 142
<211> LENGTH: 18
<212> TYPE: PRT
<213> ORGANISM: Artificial sequence
<220> FEATURE:
<223> OTHER INFORMATION: synthetic sequence

<400> SEQUENCE: 142

```
Lys Val Asp Asn Ala Leu Leu Cys Thr Pro Ser Arg Gln Ser Gly Asn
1               5                   10                  15

Ser Gln
```

<210> SEQ ID NO 143

<400> SEQUENCE: 143

000

<210> SEQ ID NO 144
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (2)..(2)
<223> OTHER INFORMATION: FORMYLATION

<400> SEQUENCE: 144

```
Leu Gly Thr Pro Ser Arg
1               5
```

<210> SEQ ID NO 145
<211> LENGTH: 7
<212> TYPE: PRT
<213> ORGANISM: Artificial sequence
<220> FEATURE:
<223> OTHER INFORMATION: synthetic sequence

<400> SEQUENCE: 145

```
Ser Leu Ser Leu Ser Pro Gly
1               5
```

<210> SEQ ID NO 146

<400> SEQUENCE: 146

000

<210> SEQ ID NO 147

```
<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (7)..(7)
<223> OTHER INFORMATION: FORMYLATION

<400> SEQUENCE: 151

Lys Val Asp Asn Ala Leu Thr Pro Ser Arg Gln Ser Gly Asn Ser Gln
1               5                   10                  15

<210> SEQ ID NO 152

<400> SEQUENCE: 152

000

<210> SEQ ID NO 153

<400> SEQUENCE: 153

000

<210> SEQ ID NO 154
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: Wherein X can be C or S

<400> SEQUENCE: 154

Leu Xaa Thr Pro Ser Arg
1               5

<210> SEQ ID NO 155

<400> SEQUENCE: 155

000
```

<210> SEQ ID NO 156

<400> SEQUENCE: 156

000

<210> SEQ ID NO 157

<400> SEQUENCE: 157

000

<210> SEQ ID NO 158
<211> LENGTH: 10
<212> TYPE: PRT
<213> ORGANISM: Artificial sequence
<220> FEATURE:
<223> OTHER INFORMATION: synthetic sequence

<400> SEQUENCE: 158

```
Gln Lys Ser Leu Ser Leu Ser Pro Gly Lys
1               5                   10
```

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162
<211> LENGTH: 107
<212> TYPE: PRT
<213> ORGANISM: Homo sapiens

<400> SEQUENCE: 162

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

-continued

```
<210> SEQ ID NO 163
<211> LENGTH: 330
<212> TYPE: PRT
<213> ORGANISM: Homo sapiens

<400> SEQUENCE: 163
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 164
<211> LENGTH: 330
<212> TYPE: PRT
<213> ORGANISM: Homo sapiens

<400> SEQUENCE: 164
```

Ala Ser Thr Lys Gly Pro Ser Val Phe Pro Leu Ala Pro Ser Ser Lys

```
                1               5                  10                 15
            Ser Thr Ser Gly Gly Thr Ala Ala Leu Gly Cys Leu Val Lys Asp Tyr
                            20                  25                 30

Phe Pro Glu Pro Val Thr Val Ser Trp Asn Ser Gly Ala Leu Thr Ser
                            35                  40                 45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Gln Thr
             65                  70                  75                 80

Tyr Ile Cys Asn Val Asn His Lys Pro Ser Asn Thr Lys Val Asp Lys
                            85                  90                 95

Lys Val Glu Pro Lys Ser Cys Asp Lys Thr His Thr Cys Pro Pro Cys
                        100                 105                 110

Pro Ala Pro Glu Leu Leu Gly Gly Pro Ser Val Phe Leu Phe Pro Pro
                        115                 120                 125

Lys Pro Lys Asp Thr Leu Met Ile Ser Arg Thr Pro Glu Val Thr Cys
             130                 135                 140

Val Val Val Asp Val Ser His Glu Asp Pro Glu Val Lys Phe Asn Trp
             145                 150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
            225                 230                 235                 240

Leu Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
            305                 310                 315                 320

Gln Lys Ser Leu Ser Leu Ser Pro Gly Lys
                            325                 330

<210> SEQ ID NO 165
<211> LENGTH: 377
<212> TYPE: PRT
<213> ORGANISM: Homo sapiens

<400> SEQUENCE: 165

Ala Ser Thr Lys Gly Pro Ser Val Phe Pro Leu Ala Pro Cys Ser Arg
             1               5                  10                 15

Ser Thr Ser Gly Gly Thr Ala Ala Leu Gly Cys Leu Val Lys Asp Tyr
                            20                  25                 30

Phe Pro Glu Pro Val Thr Val Ser Trp Asn Ser Gly Ala Leu Thr Ser
                            35                  40                 45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 166
<211> LENGTH: 326
<212> TYPE: PRT
<213> ORGANISM: Homo sapiens

<400> SEQUENCE: 166

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                      55                      60

Leu Ser Ser Val Val Thr Val Pro Ser Ser Asn Phe Gly Thr Gln Thr
65                      70                      75                      80

Tyr Thr Cys Asn Val Asp His Lys Pro Ser Asn Thr Lys Val Asp Lys
                        85                      90                      95

Thr Val Glu Arg Lys Cys Cys Val Glu Cys Pro Pro Cys Pro Ala Pro
                        100                     105                     110

Pro Val Ala Gly Pro Ser Val Phe Leu Phe Pro Pro Lys Pro Lys Asp
                        115                     120                     125

Thr Leu Met Ile Ser Arg Thr Pro Glu Val Thr Cys Val Val Val Asp
            130                     135                     140

Val Ser His Glu Asp Pro Glu Val Gln Phe Asn Trp Tyr Val Asp Gly
145                     150                     155                     160

Val Glu Val His Asn Ala Lys Thr Lys Pro Arg Glu Glu Gln Phe Asn
                        165                     170                     175

Ser Thr Phe Arg Val Val Ser Val Leu Thr Val Val His Gln Asp Trp
                        180                     185                     190

Leu Asn Gly Lys Glu Tyr Lys Cys Lys Val Ser Asn Lys Gly Leu Pro
            195                     200                     205

Ala Pro Ile Glu Lys Thr Ile Ser Lys Thr Lys Gly Gln Pro Arg Glu
            210                     215                     220

Pro Gln Val Tyr Thr Leu Pro Pro Ser Arg Glu Glu Met Thr Lys Asn
225                     230                     235                     240

Gln Val Ser Leu Thr Cys Leu Val Lys Gly Phe Tyr Pro Ser Asp Ile
                        245                     250                     255

Ser Val Glu Trp Glu Ser Asn Gly Gln Pro Glu Asn Asn Tyr Lys Thr
                        260                     265                     270

Thr Pro Pro Met Leu Asp Ser Asp Gly Ser Phe Phe Leu Tyr Ser Lys
            275                     280                     285

Leu Thr Val Asp Lys Ser Arg Trp Gln Gln Gly Asn Val Phe Ser Cys
            290                     295                     300

Ser Val Met His Glu Ala Leu His Asn His Tyr Thr Gln Lys Ser Leu
305                     310                     315                     320

Ser Leu Ser Pro Gly Lys
                325

<210> SEQ ID NO 167
<211> LENGTH: 326
<212> TYPE: PRT
<213> ORGANISM: Homo sapiens

<400> SEQUENCE: 167

Ser Thr Lys Gly Pro Ser Val Phe Pro Leu Ala Pro Cys Ser Arg Ser
1               5                       10                      15

Thr Ser Glu Ser Thr Ala Ala Leu Gly Cys Leu Val Lys Asp Tyr Phe
            20                      25                      30

Pro Glu Pro Val Thr Val Ser Trp Asn Ser Gly Ala Leu Thr Ser Gly
            35                      40                      45

Val His Thr Phe Pro Ala Val Leu Gln Ser Ser Gly Leu Tyr Ser Leu
            50                      55                      60

Ser Ser Val Val Thr Val Pro Ser Ser Leu Gly Thr Lys Thr Tyr
65                      70                      75                      80

Thr Cys Asn Val Asp His Lys Pro Ser Asn Thr Lys Val Asp Lys Arg

```
                85                  90                  95
Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 168
<211> LENGTH: 353
<212> TYPE: PRT
<213> ORGANISM: Homo sapiens

<400> SEQUENCE: 168

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125
```

```
Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Ser Gly Cys
                180                 185                 190

Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 169

<400> SEQUENCE: 169

000

<210> SEQ ID NO 170
<211> LENGTH: 107
<212> TYPE: PRT
<213> ORGANISM: Homo sapiens

<400> SEQUENCE: 170

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 171
<211> LENGTH: 107
<212> TYPE: PRT
<213> ORGANISM: Homo sapiens

<400> SEQUENCE: 171

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105
```

<210> SEQ ID NO 172
<211> LENGTH: 107
<212> TYPE: PRT
<213> ORGANISM: Mus musculus

<400> SEQUENCE: 172

```
Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 173
<211> LENGTH: 105
<212> TYPE: PRT
<213> ORGANISM: Rattus norvegicus

<400> SEQUENCE: 173

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60
```

```
Tyr Ala Ala Ser Ser Tyr Leu Ser Leu Thr Pro Glu Gln Trp Lys Ser
 65                  70                  75                  80

His Lys Ser Tyr Ser Cys Gln Val Thr His Glu Gly Ser Thr Val Glu
             85                   90                  95

Lys Thr Val Ala Pro Thr Glu Cys Ser
            100                 105

<210> SEQ ID NO 174
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: Wherein X can be S, T or A
<220> FEATURE:
<221> NAME/KEY: VARIANT
<222> LOCATION: (4)..(4)
<223> OTHER INFORMATION: Wherein X can be S, T or A

<400> SEQUENCE: 174

Cys Xaa Pro Xaa Arg
 1               5
```